US012760085B1

(12) United States Patent
Rui et al.

(10) Patent No.: US 12,760,085 B1
(45) Date of Patent: Oct. 13, 2026

(54) ENHANCED T-CELL RECEPTOR STAR AND APPLICATION THEREOF

(71) Applicant: CHINA IMMUNOTECH (BEIJING) BIOTECHNOLOGY CO., LTD., Beijing (CN)

(72) Inventors: Wei Rui, Beijing (CN); Chunyan Wu, Beijing (CN); Fang Liu, Beijing (CN)

(73) Assignee: CHINA IMMUNOTECH (BEIJING) BIOTECHNOLOGY CO., LTD., Beijing (CN)

( * ) Notice: Subject to any disclaimer, the term of this patent is extended or adjusted under 35 U.S.C. 154(b) by 1056 days.

(21) Appl. No.: 17/790,237

(22) PCT Filed: Jul. 23, 2020

(86) PCT No.: PCT/CN2020/103687
§ 371 (c)(1),
(2) Date: Mar. 28, 2023

(87) PCT Pub. No.: WO2021/135178
PCT Pub. Date: Jul. 8, 2021

(30) Foreign Application Priority Data

Dec. 30, 2019 (CN) ........................ 201911389706.0

(51) Int. Cl.

| | |
|---|---|
| ***A61K 40/32*** | (2025.01) |
| ***C07K 14/705*** | (2006.01) |
| ***C07K 16/28*** | (2006.01) |

(52) U.S. Cl.
CPC ...... *C07K 14/7051* (2013.01); *C07K 16/2827* (2013.01); *C07K 16/2863* (2013.01); *C07K 16/2887* (2013.01); *C07K 16/2896* (2013.01); *C07K 2317/565* (2013.01); *C07K 2317/622* (2013.01); *C07K 2319/03* (2013.01)

(58) Field of Classification Search
CPC ............................ C07K 14/7051; A61K 40/32
See application file for complete search history.

(56) References Cited

U.S. PATENT DOCUMENTS

2014/0255398 A1 9/2014 Igawa et al.

FOREIGN PATENT DOCUMENTS

| | | |
|---|---|---|
| CN | 104822705 | 8/2015 |
| CN | 109790211 | 5/2019 |
| CN | 110016074 | 7/2019 |
| CN | 110352068 | 10/2019 |
| JP | 2019527555 | 10/2019 |
| WO | WO 2014/065961 | 5/2014 |
| WO | WO 2015/143382 | 5/2015 |

(Continued)

OTHER PUBLICATIONS

Neunkircher et al., Human TCR transgenic Bet v 1-specific Th1 cells suppress the effector function of Bet v 1-specific Th2 cells (J Immuno, 2011, 187:4077-4087). (Year: 2011).*

(Continued)

*Primary Examiner* — Arthur S Leonard
(74) *Attorney, Agent, or Firm* — Robin L. Teskin; Baker, Donelson, Bearman, Caldwell & Berkowitz PC

(57) ABSTRACT

The present invention relates to the field of biomedicine, and particularly relates to an enhanced T-cell receptor STAR and an application thereof. Specifically, disclosed are an improved Synthetic T-cell receptor and Antigen Receptor (STAR), T cells containing the STAR and uses thereof.

25 Claims, 14 Drawing Sheets

Specification includes a Sequence Listing.

(56) References Cited

FOREIGN PATENT DOCUMENTS

| | | | | |
|---|---|---|---|---|
| WO | WO 2015/157252 | | 10/2015 | |
| WO | WO 2015/184228 | | 12/2015 | |
| WO | WO 2016/022400 | | 2/2016 | |
| WO | WO-2016179006 | A1 * | 11/2016 | ......... A61K 38/1703 |
| WO | 2017070608 | | 4/2017 | |
| WO | 2018026691 | | 2/2018 | |
| WO | 2018102795 | A3 | 6/2018 | |
| WO | WO-2018102795 | A2 * | 6/2018 | ................ A61P 3/10 |
| WO | 2018148454 | | 8/2018 | |
| WO | 2019057122 | | 3/2019 | |
| WO | 2021223707 | | 11/2021 | |

OTHER PUBLICATIONS

GenBank: ADD84718.1. Betula verrucosa antigen 1 specific T cell receptor alpha chain [*Homo sapiens*. Oct. 18, 2011 (Year: 2011).*

International Search Report corresponding to International Application No. PCT/CN2020/103687 dated Oct. 27, 2020 (English translation).

Written Opinion corresponding to International Application No. PCT/CN2020/103687 dated Oct. 27, 2020 (English translation).

Eshhar Z, Gross G, Waks T, Lustgarten J, Bach N, Ratner A, Treisman J, Schindler DG, T-bodies: chimeric T-cell receptors with antibody-type specificity. Methods. Oct. 1, 1995;8(2):133-42.

Cohen CJ, Zhao Y, Zheng Z, Rosenberg SA, Morgan RA. Enhanced antitumor activity of murine-human hybrid T-cell receptor (TCR) in human lymphocytes is associated with improved pairing and TCR/CD3 stability. Cancer research. Sep. 1, 2006;66(17):887-86.

Abken H, Hombach A, Heuser C, Sircar R, Pohl C, Reinhold U. Chimeric T-cell receptors: highly specific tools to target cytotoxic T-lymphocytes to tumour cells. Cancer treatment reviews. Mar. 1, 1997;23(2):97-112.

Liu Y, Liu G, Wang J, Zheng ZY, Jia L, Rui W, Huang D, Zhou ZX, Zhou L, Wu X, Lin S. Chimeric STAR receptors using TCR machinery mediate robust responses against solid tumors. Science translational medicine. Mar. 24, 2021;13(586):eabb5191 (16 pages).

Chen L, Tian Y, Zhan K, Chen A, Weng Z, Huang J, Li Y. A humanized TCR retaining authentic specificity and affinity conferred potent anti-tumour cytotoxicity. Immunology. Sep. 2018;155(1):123-36.

Chaundhary P.M., "Cancer treatment related SIR encoded polypeptide, SEQ ID 9500," WO 2018/102795 A2 (published Jun. 7, 2018; international filing Dec. 2, 2017; priority Dec. 2, 2016).

Chaudhary, P.M., "Cancer treatment related Ig CL, SEQ ID 3010," WO 2018/102795 A2 (published Jun. 7, 2018; international filing Dec. 2, 2017; priority Dec. 2, 2016).

Chaudhary, P.M., "Cancer treatment related Ig CL, SEQ ID 3015," WO 2018/102795 A2 (published Jun. 7, 2018; international filing Dec. 2, 2017; priority Dec. 2, 2016).

* cited by examiner

```
UserSeq1    1 DIQNPDPAVYQLRDSKSS  SEQ ID NO 51
UserSeq2    1 DIQNPEPAVYQLKDPRSQ  SEQ ID NO 3
              ***** ****** *   *
```

*FIG. 3*

```
1 DLKNVFPPEVAVFEPSEAEISHTQK  SEQ ID NO 50
1 DLRNVTPPKVSLFEPSKAEIANKQK  SEQ ID NO 16
  ** ** ** *   **** ***   **
```

*FIG. 4*

| Name of the mutation | Modification of TCRα chain constant region | Modification of TCRβchain constant region |
|---|---|---|
| N.Rec-1 | 4 aa truncated at N terminal, humanized | 6 aa truncated at N terminal, humanized |
| N.Rec-2 | 8 aa truncated at N terminal, humanized | 12 aa truncated at N terminal, humanized |
| N.Rec-3 | 12 aa truncated at N terminal, humanized | 18 aa truncated at N terminal, humanized |
| N.Rec-4 | aa 1-14 at N terminal humanized, aa 15-18 deleted | aa 1-16 humanized, aa 17, 21-26 deleted |
| N.DLT | 18 aa at N terminal truncated | 25 aa at N terminal truncated |
| C.DLT | 15 aa at C terminal truncated | 15aa at C terminal truncated |
| N.rRec | 18 aa at N terminal randomly rearranged | 25 aa at N terminal randomly rearranged |
| TM9 | aa 111-119 in α chain transmembrane region | - |
| Cys | threonine at position 48 of α chain was mutated to cysteine | serine at position 56 of **β** chain was mutated to cysteine |

*FIG. 5A*

| no | mutation | C.DLT | N.DLT | N.Rec -1 | N.Rec -2 | N.Rec -3 | N.Rec -4 | N.rRec | Cys | TM9 |
|---|---|---|---|---|---|---|---|---|---|---|
| 1 | WT | | | | | | | | | |
| 2 | C.DLT | + | | | | | | | | |
| 3 | N.DLT | | + | | | | | | | |
| 4 | N.Rec-1 | | | + | | | | | | |
| 5 | N.Rec-2 | | | | + | | | | | |
| 6 | N.Rec-3 | | | | | + | | | | |
| 7 | N.Rec-4 | | | | | | + | | | |
| 8 | N.rRec | | | | | | | + | | |
| 9 | Cys | | | | | | | | + | |
| 10 | TM9 | | | | | | | | | + |
| 11 | Cys-N.Rec-1 | | | + | | | | | + | |
| 12 | TM9-N.Rec-1 | | | + | | | | | | + |
| 13 | Cys-TM9 | | | | | | | | + | + |
| 14 | Cys-TM9-N.Rec-1 | | | + | | | | | + | + |

↓

Various mutants of TCRα/β, 13 each

↓

Further combinations of TCRα and TCRβ chains

ENHANCED T-CELL RECEPTOR STAR AND APPLICATION THEREOF

CROSS-REFERENCE TO RELATED APPLICATIONS

This application is a U.S. Nat'l Phase of Int'l Appl. No. PCT/CN2020/103687, filed Jul. 23, 2020, which claims priority to Int'l application No. 201911389706.0, filed Dec. 30, 2019, each of which is incorporated herein in its entirety and for all purposes.

SEQUENCE LISTING DISCLOSURE

The contents of the electronic sequence listing (11584980064001.txt; Size: 55,782 bytes; and Date of Creation: May 26, 2026) is herein incorporated by reference in its entirety.

TECHNICAL FIELD

The present invention relates to the field of biomedicine, and particularly relates to an enhanced T-cell receptor STAR and an application thereof. Specifically, disclosed are an improved Synthetic T-cell receptor and Antigen Receptor (STAR), T cells containing the STAR and uses thereof.

BACKGROUND

The elimination of tumor cells by immune cells in human bodies is realized in the mode that dendritic cells recognize mutant genes of the tumor cells and display mutant information to T cells. The T cells then search for and kill the tumor cells carrying the mutation. Sometimes, the tumor cells down-regulate MHC molecules that can display mutated peptide fragments, thus escaping from killing by the T cells and gradually developing into uncontrollable cancers.

The chimeric antigen receptor T cell (CAR-T) therapy is an anti-cancer immunization therapy with good efficacy in recent years. Unlike the way of natural T cells to recognize the tumor cells, CAR-T cells do not rely on the MHC molecules for tumor cell recognition. A CAR molecule comprises three major parts which includes an extracellular region which is an antigen recognition structural domain derived from an antibody and is responsible for recognizing a target antigen, a transmembrane region, and an intracellular region which is a signaling molecule and a costimulatory signaling molecule which are derived from T-cell receptors and is responsible for transducing T cell activation signals upon receiving stimulation. Its working principle is as follows: when the CAR molecule binds to its corresponding antigen, the CAR molecule aggregates, thereby increasing the local phosphorylation level, activating downstream signals and finally initiating the effector function of the T cells to kill target tumor cells.

The CD19-protein-targeted chimeric antigen receptor T cell (CD19-CAR-T) therapy has been approved for two clinical applications in the United States for the treatment of relapsed refractory B-cell lymphoma. However, the CAR-T therapy encountered difficulties in the treatment of solid tumors. There are multiple factors that make the T cell therapy fail to achieve good efficacy in the treatment of solid tumors, one of the important reasons is that the function of CAR-T cells is inhibited in the tumor microenvironment, and the T cells are prone to depletion and apoptosis. Recent studies suggest that disability of the T cells may be related to signaling pathway properties of the chimeric antigen receptors.

A T-cell receptor (TCR) complex molecule contains multiple chains, the TCR α chain and the TCR β chain are responsible for recognizing MHC-polypeptide molecules, and the other 6 CD3 subunits bind to the TCR α/β chains and have the function of signal transduction. The natural TCR complex contains a total of 10 ITAM signal sequences, and transduction of signals stronger than CAR can be theoretically realized. Previous studies have shown that although transduction of TCR signals is slower than that of CAR signals, the TCR signals are more persistent. Therefore, by using the natural TCR signal transduction function, it would be possible to construct a novel receptor to alleviate T cell dysfunction and enable it to exert better anti-solid tumor effects.

An extracellular region of a TCR is very similar to an Fab domain of the antibody, thus a TCR variable region sequence can be substituted with an antibody variable region sequence to obtain the synthetic TCR and antigen receptor (STAR), which has both the specificity of the antibody and the superior signal transduction function of the natural TCR, and can mediate complete T cell activation.

However, the STAR derived from the natural TCR still suffer from poor membrane stability, low a/β chain pairing ability, mismatch with an endogenous TCR, difficulty in introduction into the T cells and the like. Therefore, there remains a need in the field for an improved STAR.

BRIEF DESCRIPTION OF THE DRAWINGS

FIG. 3 shows sequence alignment results of 18 amino acids of the N-terminals of human and mouse TCR α chain constant regions. UserSeq1 is a human sequence, and UserSeq2 is a mouse sequence.

FIG. 4 shows sequence alignment results of 25 amino acids of the N-terminals of human and mouse TCR β chain constant regions. UserSeq1 is a human sequence, and UserSeq2 is a mouse sequence.

SUMMARY OF THE INVENTION

Figure 1A:
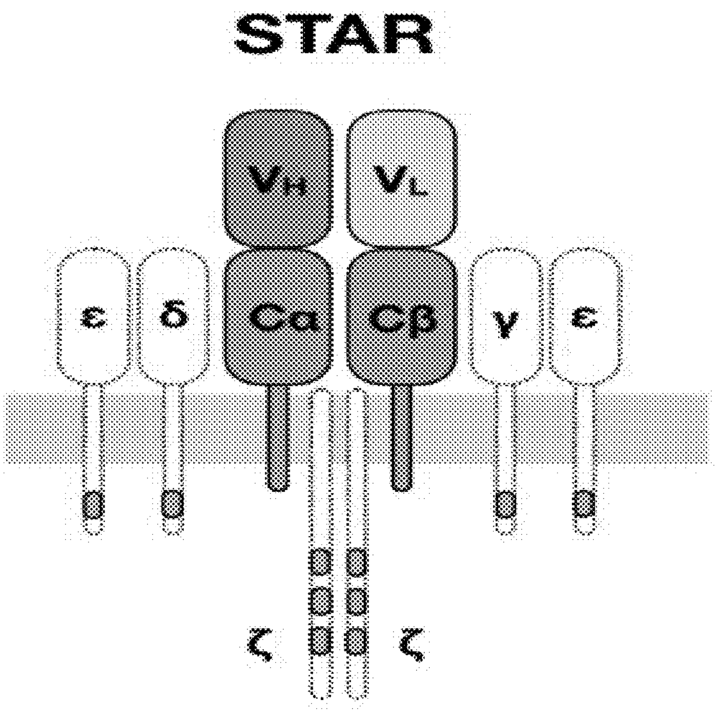
FIG. 1 shows the structure of an STAR. A, the structure diagram of a prototype of the STAR; B, the structure diagram of an improved STAR; and C, the structure diagram of dual-STARs targeting different target antigens.

Unless otherwise indicated or defined, all terms used have their ordinary meanings in the art, which will be understood by those skilled in the art. Reference is also made, for example, to standard manuals such as Sambrook et al. "Molecular Cloning: A Laboratory Manual"; Lewin, "Genes VIII"; and Roitt et al. "Immunology" (8th Edition) as well as the general prior art cited herein. Moreover, unless otherwise indicated, all methods, steps, techniques and operations not specifically described may be, and have been carried out in manners known per se, and the manners will be known by those skilled in the art. Reference is also made, for example, to standard manuals, the above general prior art and other references cited therein.

As used herein, the term "and/or" covers all combinations of items linked by the term, and it should be considered that each combination has been individually listed herein. For example, "A and/or B" covers "A", "A and B" and "B". For example, "A, B and/or C" covers "A", "B", "C", "A and B", "A and C", "B and C" and "A and B and C".

When the term of "comprise" is used herein to describe a sequence of a protein or nucleic acid, the protein or nucleic acid may consist of the sequence, or one or both ends of the protein or nucleic acid may have additional amino acids or nucleotides, but the activity described in the present invention still exists. Furthermore, it is clear to those skilled in the art that methionine encoded by an initiation codon at the N-terminal of a polypeptide will be retained under certain practical circumstances (for example, when expressed in a particular expression system), but the function of the polypeptide is not substantially affected. Therefore, when a particular polypeptide amino acid sequence is described in the specification and claims of the present invention, although the methionine encoded by the initiation codon at the N-terminal may not be contained, a sequence comprising the methionine is also covered in this regard, and accordingly, an encoding nucleotide sequence may also comprise the initiation codon; and vice versa.

In one aspect, the invention provides a synthetic T-cell receptor and antigen receptor (STAR) comprising an α chain and a β chain, wherein the α chain comprises a first antigen-binding region and a first constant region, and the β chain comprises a second antigen-binding region and a second constant region,

- wherein the first constant region is a variant of a constant region of an α chain of a natural T-cell receptor, which comprises i) an N-terminal modification; ii) a cysteine substitution; and/or iii) a hydrophobic amino acid substitution as compared with the constant region of the α chain of the natural T-cell receptor; and/or
- wherein the second constant region is a variant of a constant region of a β chain of a natural T-cell receptor, which comprises i) an N-terminal modification; and ii) a cysteine substitution as compared with the constant region of the β chain of the natural T-cell receptor.

In some embodiments, the antigen-binding region is fused to the N-terminal of the constant region.

In some embodiments, the α and β chains are capable of forming a functional TCR complex upon expression in T cells. For example, the α and β chains are capable of binding to endogenous CD3 molecules (CD3εδ, CD3γε, CD3ζζ) of the cells to form an 8-subunit TCR complex after expression in the T cells, the TCR complex is displayed on the cell surfaces and activates the T cells upon binding to target antigen. The functional TCR complex is capable of activating the T cells upon specific binding to the target antigen.

As used herein, the "N-terminal modification" means that the N-terminal of the referred amino acid sequence (polypeptide or protein) comprises substitution, deletion and/or addition of one or more amino acids, and the term may also include the deletion of one or more continuous amino acids from the N-terminal of the referred amino acid sequence (polypeptide or protein).

As used herein, the "cysteine substitution" or "hydrophobic amino acid substitution" refers to the substitution of an original amino acid in the referred amino acid sequence (polypeptide or protein) with a cysteine or hydrophobic amino acid, wherein the hydrophobic amino acid substitution can be that a hydrophilic amino acid is substituted by a hydrophobic amino acid, and can also be that an amino acid with low hydrophobicity is substituted by an amino acid with high hydrophobicity.

In some embodiments, the first constant region is derived from a constant region of an α chain of a human T-cell receptor, a constant region of an α chain of a non-human primate T-cell receptor, a constant region of an α chain of a rodent, e.g., mouse, T-cell receptor. The exemplary constant region of the α chain of the human T-cell receptor comprises an amino acid sequence set forth in SEQ ID NO: 1. The exemplary constant region of the α chain of the mouse T-cell receptor comprises an amino acid sequence set forth in SEQ ID NO: 2. In some preferred embodiments, the first constant region is derived from the constant region of the α chain of the mouse T-cell receptor. In some embodiments, the first constant region comprises modifications within 18 amino acids at the N terminal as compared with the native T-cell receptor α chain constant region. In some embodiments, the first constant region is derived from the constant region of the α chain of the mouse T-cell receptor, and an amino acid sequence set forth in SEQ ID NO: 3 (DIQNPEPAVYQLKDPRSQ) is deleted as compared with the constant region of the α chain of the native mouse T-cell receptor. In some particular embodiments, the first constant region comprising the N-terminal modification comprises an amino acid sequence set forth in SEQ ID NO: 4. (Corresponding to TCRaC-N.DLT)

In some embodiments, the first constant region comprises modifications at the N terminal as compared with the native T-cell receptor α chain constant region, wherein one or more or all of amino acids at positions 15-18 at the N-terminal are deleted, and the amino acid number refers to SEQ ID NO: 2. In some embodiments, the first constant region is derived from the mouse T-cell receptor α chain constant region, one or more or all of the amino acids at positions 15-18 at the N-terminal are deleted as compared with the constant region of the α chain of the native mouse T-cell receptor, and the amino acid number refers to SEQ ID NO: 2. In some embodiments, the first constant region is derived from the mouse T-cell receptor α chain constant region, one or more or all of the amino acids at positions 15-18 at the N-terminal are deleted as compared with the constant region of the α chain of the native mouse T-cell receptor, wherein the amino acids at positions 1-14 at the N-terminal are substituted by corresponding amino acids of the constant region of the α chain of the native human T-cell receptor, and the amino acid number refer to SEQ ID NO: 2. In some particular embodiments, the first constant region comprising N-terminal modification comprises an amino acid sequence set forth in SEQ ID NO: 5. (Corresponding to TCRaC-N.Rec-4)

In some embodiments, the first constant region is derived from the mouse T-cell receptor α chain constant region, and X continuous amino acids from the N-terminal are deleted compared with the constant region of the α chain of the native mouse T-cell receptor, and/or the amino acids from positions (X+1)-18 at the N-terminal are substituted by corresponding amino acids of the constant region of the α chain of the native human T-cell receptor, wherein X is 0, 1, 2, 3, 4, 5, 6, 7, 8, 9, 10, 11, 12, 13, 14, 15, 16, 17 or 18.

For example, in some preferred embodiments, the first constant region is derived from the mouse T-cell receptor α chain constant region, amino acids at positions 1-14 at the N-terminal are deleted compared with the constant region of the α chain of the native mouse T-cell receptor, wherein amino acids at positions 5-18 at the N-terminal are substituted by corresponding amino acids of the constant region of the α chain of the native human T-cell receptor, and the amino acid number refers to SEQ ID NO: 2. In some particular embodiments, the first constant region comprising N-terminal modification comprises the amino acid sequence set forth in SEQ ID NO: 34. (Corresponding to TCRaC-N.Rec-1)

In some embodiments, the first constant region is derived from the mouse T-cell receptor α chain constant region, the amino acids at positions 1-8 at the N-terminal are deleted compared with the constant region of the α chain of the native mouse T-cell receptor, wherein amino acids at positions 9-18 at the N-terminal are substituted by corresponding amino acids of the constant region of the α chain of the native human T-cell receptor, and the amino acid number refers to SEQ ID NO: 2. In some particular embodiments, the first constant region comprising N-terminal modification comprises an amino acid sequence set forth in SEQ ID NO: 35. (Corresponding to TCRaC-N.Rec-2)

In some embodiments, the first constant region is derived from the mouse T-cell receptor α chain constant region, amino acids at positions 1-12 at the N-terminal are deleted compared with the constant region of the α chain of the native mouse T-cell receptor, wherein amino acids at positions 13-18 at the N-terminal are substituted by corresponding amino acids of the constant region of the α chain of the native human T-cell receptor, and the amino acid number refers to SEQ ID NO: 2. In some particular embodiments, the first constant region comprising N-terminal modification comprises an amino acid sequence set forth in SEQ ID NO: 36. (Corresponding to TCRaC-N.Rec-3)

In some embodiments, the first constant region comprises a cysteine substitution at position 48 compared with the native T-cell receptor α chain constant region, and the amino acid number refers to SEQ ID NO: 2. In some embodiments, compared with the native T-cell receptor α chain constant region, threonine at position 48 of the first constant region is mutated to cysteine, and the amino acid number refers to SEQ ID NO: 2. In some particular embodiments, the first constant region comprising the cysteine substitution comprises an amino acid sequence set forth in SEQ ID NO: 6 (derived from the constant region of the α chain of the human T-cell receptor). In some particular embodiments, the first constant region comprising the cysteine substitution comprises an amino acid sequence set forth in SEQ ID NO: 7 (derived from the mouse T-cell receptor α chain constant region). (Corresponding to TCRaC-Cys)

As used herein, "the amino acid number refers to SEQ ID NO: x" (SEQ ID NO: x is a specific sequence listed herein) means that the position number of the specific amino acid described is the position number of the corresponding amino acid on SEQ ID NO: x. The correspondence of amino acids in different sequences can be determined according to sequence alignment methods well known in the art. For example, the correspondence of the amino acids can be determined by an online alignment tool from EMBL-EBI (https://www.ebi.ac.uk/Tools/psa/), wherein two sequences can be aligned by using a Needleman-Wunsch algorithm by using default parameters. For example, an amino acid at position 46 from its N-terminal of a polypeptide aligns with the amino acid at position 48 of SEQ ID NO: x in a sequence alignment, then the amino acid in the polypeptide may also be described herein as "an alanine at position 48 of the polypeptide, and the amino acid position refers to SEQ ID NO: x".

In some embodiments, the first constant region comprises a hydrophobic amino acid substitution within the transmembrane region compared with the native T-cell receptor α chain constant region, for example, the transmembrane region comprises an amino acid sequence at positions 111-119, and the amino acid number refers to SEQ ID NO: 2. In some embodiments, the first constant region comprises hydrophobic amino acid substitutions at positions 112, 114, and/or 115 compared with the native T-cell receptor α chain constant region, and the amino acid number refers to SEQ ID NO: 2. In some embodiments, compared with the native T-cell receptor α chain constant region, serine at position 112 of the first constant region is substituted with leucine, methionine at position 114 is substituted with isoleucine, and/or glycine at position 115 is substituted with valine; and the amino acid number refers to SEQ ID NO: 2. In some embodiments, compared with the native T-cell receptor α chain constant region, the serine at position 112 of the first constant region is substituted with the leucine, the methionine at position 114 is substituted with isoleucine, and/or the glycine at position 115 is substituted with the valine; and the amino acid number refers to SEQ ID NO: 2. In some embodiments, the first constant region comprising the hydrophobic amino acid substitution comprises the transmembrane region set forth in SEQ ID NO: 8 (derived from the mouse T-cell receptor α chain constant region). In some particular embodiments, the first constant region comprising the hydrophobic amino acid substitution comprises an amino acid sequence set forth in SEQ ID NO: 9 (derived from the mouse T-cell receptor α chain constant region). (Corresponding to TCRaC-TM9)

In some embodiments, the first constant region is derived from the mouse T-cell receptor α chain constant region, the amino acids at positions 1~4 at the N-terminal are deleted compared with the constant region of the α chain of the native mouse T-cell receptor, wherein amino acids at positions 5-18 at the N-terminal are substituted by corresponding amino acids of the constant region of the α chain of the native human T-cell receptor, the threonine at position 48 is mutated to the cysteine, and the amino acid number refers to SEQ ID NO: 2. In some particular embodiments, the first constant region comprises the amino acid sequence set forth in SEQ ID NO: 11. (Corresponding to TCRaC-Cys-N.Rec-1)

In some embodiments, the first constant region is derived from the mouse T-cell receptor α chain constant region, the amino acids at positions 1~4 at the N-terminal are deleted compared with the constant region of the α chain of the native mouse T-cell receptor, wherein amino acids at positions 5-18 at the N-terminal are substituted by corresponding amino acids of the constant region of the α chain of the native human T-cell receptor, the serine at position 112 is substituted with the leucine, the methionine at position 114 is substituted with the isoleucine, the glycine at position 115 is substituted with the valine, and the amino acid number refers to SEQ ID NO: 2. In some particular embodiments, the first constant region comprises an amino acid sequence set forth in SEQ ID NO: 12. (Corresponding to TCRaC-TM9-N.Rec-1)

In some embodiments, the first constant region is derived from the mouse T-cell receptor α chain constant region, compared with the constant region of the α chain of the native mouse T-cell receptor, the threonine at position 48 is mutated to the cysteine, the serine at position 112 is substituted with the leucine, the methionine at position 114 is substituted with the isoleucine, the glycine at position 115 is substituted with the valine, and the amino acid number refers to SEQ ID NO: 2. In some particular embodiments, the first constant region comprises an amino acid sequence set forth in SEQ ID NO: 10. (Corresponding to TCRaC-Cys-TM9)

In some embodiments, the first constant region is derived from the mouse T-cell receptor α chain constant region, amino acids at positions 1~4 at the N-terminal are deleted compared with the constant region of the α chain of the native mouse T-cell receptor, wherein amino acids at positions 5-18 at the N-terminal are substituted by corresponding amino acids of the constant region of the α chain of the native human T-cell receptor, the threonine at position 48 is mutated to the cysteine, the serine at position 112 is substituted with the leucine, the methionine at position 114 is substituted with the isoleucine, the glycine at position 115 is substituted with the valine, and the amino acid number refers to SEQ ID NO: 2. In some particular embodiments, the first constant region comprises an amino acid sequence set forth in SEQ ID NO: 13. (Corresponding to TCRaC-Cys-TM9-N.Rec-1)

In some embodiments, the second constant region is derived from a human T-cell receptor β chain constant region, a non-human primate T-cell receptor β chain constant region and a rodent, e.g., mouse, T-cell receptor β chain constant region. The exemplary human T-cell receptor β chain constant region comprises an amino acid sequence set forth in SEQ ID NO: 14. The exemplary mouse T-cell receptor α chain constant region comprises an amino acid sequence set forth in SEQ ID NO: 15. In some preferred embodiments, the first constant region is derived from the mouse T-cell receptor β chain constant region.

In some embodiments, the second constant region comprises modifications within the 25 amino acids at the N terminal compared with the native T-cell receptor β chain constant region. In some embodiments, the second constant region is derived from the mouse T-cell receptor β chain constant region, and the amino acid sequence set forth in SEQ ID NO: 16 (DLRNVTPPKVSLFEPSKAEIANKQK) is deleted compared with the native mouse T-cell receptor β chain constant region. In some particular embodiments, the second constant region comprising N-terminal modification comprises an amino acid sequence set forth in SEQ ID NO: 17. (Corresponding to TCRbC-N.DLT)

In some embodiments, the second constant region comprises modifications at the N terminal compared with the native T-cell receptor β chain constant region, wherein one or more or all of amino acids at positions 17 and 21-25 at the N-terminal are deleted, and the amino acid number refers to SEQ ID NO: 15. In some embodiments, the second constant region is derived from the mouse T-cell receptor β chain constant region, and one or more or all of amino acids at positions 17 and 21-25 at the N-terminal are deleted compared with the native mouse T-cell receptor β chain constant region, and the amino acid number refers to SEQ ID NO: 15. In some embodiments, the second constant region is derived from the mouse T-cell receptor β chain constant region, one or more or all of amino acids at positions 17 and 21-25 at the N-terminal are deleted compared with the native mouse T-cell receptor β chain constant region, wherein amino acids at positions 1-16 at the N-terminal are substituted with corresponding amino acids of the native human T-cell receptor β chain constant region, and the amino acid number refers to SEQ ID NO: 15. In some particular embodiments, the second constant region comprising N-terminal modification comprises an amino acid sequence set forth in SEQ ID NO: 18. (Corresponding to TCRbC-N.Rec-4)

In some embodiments, the second constant region is derived from the mouse T-cell receptor β chain constant region, and X contiguous amino acids from the N-terminal are deleted compared with the native mouse T-cell receptor β chain constant region, and/or amino acids at positions (X+1)-25 at the N-terminal are substituted by corresponding amino acids of the native human T-cell receptor β chain constant region, wherein X is 0, 1, 2, 3, 4, 5, 6, 7, 8, 9, 10, 11, 12, 13, 14, 15, 16, 17, 18, 19, 20, 21, 22, 23, 24 or 25.

In some embodiments, the second constant region is derived from the mouse T-cell receptor β chain constant region, amino acids at positions 1-6 at the N-terminal are deleted compared with the native mouse T-cell receptor β chain constant region, wherein amino acids at positions 7-25 at the N-terminal are substituted by corresponding amino acids of the native human T-cell receptor β chain constant region, and the amino acid number refers to SEQ ID NO: 15. In some particular embodiments, the second constant region comprising N-terminal modification comprises an amino acid sequence set forth in SEQ ID NO: 37. (Corresponding to TCRbC-N.Rec-1)

In some embodiments, the second constant region is derived from the mouse T-cell receptor β chain constant region, amino acids at positions 1-12 at the N-terminal are deleted compared with the native mouse T-cell receptor β chain constant region, wherein amino acids at positions 13-25 at the N-terminal are substituted by corresponding amino acids of the native human T-cell receptor β chain constant region, and the amino acid number refers to SEQ ID NO: 15. In some particular embodiments, the second constant region comprising N-terminal modification comprises the amino acid sequence set forth in SEQ ID NO: 38. (Corresponding to TCRbC-N.Rec-2)

In some embodiments, the second constant region is derived from the mouse T-cell receptor β chain constant region, amino acids at positions 1-18 at the N-terminal are deleted compared with the native mouse T-cell receptor β chain constant region, wherein amino acids at positions 19-25 at the N-terminal are substituted by corresponding amino acids of the native human T-cell receptor β chain constant region, and the amino acid number refers to SEQ ID NO: 15. In some particular embodiments, the second constant region comprising N-terminal modification comprises an amino acid sequence set forth in SEQ ID NO: 39. (Corresponding to TCRbC-N.Rec-3)

In some embodiments, compared with the native T-cell receptor β chain constant region, the second constant region comprises a cysteine substitution at position 56, and the amino acid number refers to SEQ ID NO: 15. In some embodiments, compared with a native T-cell receptor β chain constant region, the serine at position 56 of the second constant region is mutated to the cysteine, and the amino acid number refers to SEQ ID NO: 15. In some particular embodiments, the second constant region comprising the cysteine substitution comprises an amino acid sequence set forth in SEQ ID NO: 19 (derived from the human T-cell receptor β chain constant region). In some particular embodiments, the second constant region comprising the cysteine substitution comprises an amino acid sequence set forth in SEQ ID NO: 20 (derived from the mouse T-cell receptor β chain constant region). (Corresponding to TCRbC-Cys)

In some embodiments, the second constant region is derived from the mouse T-cell receptor β chain constant region, amino acids at positions 1-6 at the N-terminal are deleted compared with the native mouse T-cell receptor β chain constant region, wherein amino acids at positions 7-25 at the N-terminal are substituted by corresponding amino acids of the native human T-cell receptor β chain constant region, the serine at position 56 is mutated to the cysteine, and the amino acid number refers to SEQ ID NO: 15. In some particular embodiments, the second constant region comprises an amino acid sequence set forth in SEQ ID NO: 21. (Corresponding to TCRbC-Cys-N.Rec-1)

In some preferred embodiments, the first constant region is derived from the mouse T-cell receptor α chain constant region, amino acids at positions 1~4 at the N-terminal are deleted compared with the constant region of the α chain of the native mouse T-cell receptor, wherein amino acids at positions 5-18 at the N-terminal are substituted by corresponding amino acids of the constant region of the α chain of the native human T-cell receptor, and the amino acid number refers to SEQ ID NO: 2; and the second constant region is derived from the mouse T-cell receptor β chain constant region, amino acids at positions 1-6 at the N-terminal are deleted compared with the native mouse T-cell receptor β chain constant region, wherein amino acids at positions 7-25 at the N-terminal are substituted by corresponding amino acids of the native human T-cell receptor β chain constant region, and the amino acid number refers to SEQ ID NO: 15. In some specific embodiments, the first constant region comprises an amino acid sequence set forth in SEQ ID NO: 34, and the second constant region comprises the amino acid sequence set forth in SEQ ID NO: 37.

In some preferred embodiments, the first constant region is derived from the mouse T-cell receptor α chain constant region, compared with the constant region of the α chain of the native mouse T-cell receptor, the threonine at position 48 is mutated to the cysteine, and the amino acid number refers to SEQ ID NO: 2; and the second constant region is derived from the mouse T-cell receptor β chain constant region, compared with the native mouse T-cell receptor β chain constant region, the serine at position 56 is mutated to the cysteine, and the amino acid number refers to SEQ ID NO: 15. In some particular embodiments, the first constant region comprises an amino acid sequence set forth in SEQ ID NO: 7, and the second constant region comprises an amino acid sequence set forth in SEQ ID NO: 20.

In some preferred embodiments, the first constant region is derived from the mouse T-cell receptor α chain constant region, compared with the constant region of the α chain of the native mouse T-cell receptor, the serine at position 112 is substituted with the leucine, the methionine at position 114 is substituted with the isoleucine, the glycine at position 115 is substituted with the valine, and the amino acid number refers to SEQ ID NO: 2; and the second constant region is the native mouse T-cell receptor β chain constant region. In some specific embodiments, the first constant region comprises an amino acid sequence set forth in SEQ ID NO: 9, and the second constant region comprises an amino acid sequence set forth in SEQ ID NO: 15.

In some preferred embodiments, the first constant region is derived from the mouse T-cell receptor α chain constant region, compared with the constant region of the α chain of the native mouse T-cell receptor, the amino acids at positions 1~4 at the N-terminal are deleted, wherein amino acids at positions 5-18 at the N-terminal are substituted by corresponding amino acids of the constant region of the α chain of the native human T-cell receptor, the threonine at position 48 is mutated to the cysteine, and the amino acid number refers to SEQ ID NO: 2; and the second constant region is derived from the mouse T-cell receptor β-chain constant region, the amino acids at positions 1-6 at the N-terminal are deleted compared with the native mouse T-cell receptor β-chain constant region, wherein amino acids at positions 7-25 at the N-terminal are substituted with corresponding amino acids of the native human T-cell receptor β-chain constant region, the serine at position 56 is mutated to the cysteine, the cysteine at position 56 is mutated to the cysteine, and the amino acid number refers to SEQ ID NO: 15. In some specific embodiments, the first constant region comprises an amino acid sequence set forth in SEQ ID NO: 11, and the second constant region comprises the amino acid sequence set forth in SEQ ID NO: 21 In some preferred embodiments, the first constant region is derived from the constant region of the α chain of the mouse T-cell receptor, amino acids at positions 1~4 at the N-terminal are deleted compared with the constant region of the α chain of the native mouse T-cell receptor, wherein amino acids at positions 5-18 at the N-terminal are substituted by corresponding amino acids of the constant region of the α chain of the native human T-cell receptor, the serine at position 112 is substituted with the leucine, the methionine at position 114 is substituted with the isoleucine, the glycine at position 115 is substituted with the valine, and the amino acid number refers to SEQ ID NO: 2; and the second constant region is derived from the mouse T-cell receptor β chain constant region, amino acids at positions 1-6 at the N-terminal are deleted compared with the native mouse T-cell receptor β chain constant region, wherein amino acids at positions 7-25 at the N-terminal are substituted by corresponding amino acids of the native human T-cell receptor β chain constant region, and the amino acid number refers to SEQ ID NO: 15. In some particular embodiments, the first constant region comprises an amino acid sequence set forth in SEQ ID NO: 12, and the second constant region comprises an amino acid sequence set forth in SEQ ID NO: 37.

In some preferred embodiments, the first constant region is derived from the constant region of the α chain of the mouse T-cell receptor, compared with the constant region of the α chain of the native mouse T-cell receptor, the threonine at position 48 is mutated to the cysteine, the serine at position 112 is substituted with the leucine, the methionine at position 114 is substituted with the isoleucine, the glycine at position 115 is substituted with the valine, and the amino acid number refers to SEQ ID NO: 2; and the second constant region is derived from the mouse T-cell receptor β chain constant region, the serine at position 56 is mutated to the cysteine compared with the native mouse T-cell receptor β chain constant region, and the amino acid number refers to SEQ ID NO: 15. In some particular embodiments, the first constant region comprises the amino acid sequence set forth in SEQ ID NO: 10, and the second constant region comprises the amino acid sequence set forth in SEQ ID NO: 20.

In some preferred embodiments, the first constant region is derived from the constant region of the α chain of the mouse T-cell receptor, amino acids at positions 1~4 at the N-terminal are deleted compared with the constant region of the α chain of the native mouse T-cell receptor, wherein amino acids at positions 5-18 at the N-terminal are substituted by corresponding amino acids of the constant region of the α chain of the native human T-cell receptor, the threonine at position 48 is mutated to the cysteine, the serine at position 112 is substituted with the leucine, the methionine at position 114 is substituted with the isoleucine, the glycine at position 115 is substituted with the valine, and the amino acid number refers to SEQ ID NO: 2; and the second constant region is derived from the mouse T-cell receptor β-chain constant region, amino acids at positions 1-6 at the N-terminal are deleted compared with the native mouse T-cell receptor β-chain constant region, wherein amino acids at positions 7-25 at the N-terminal are substituted with corresponding amino acids of the native human T-cell receptor β-chain constant region, the serine at position 56 is mutated to the cysteine, the cysteine at position 56 is mutated to the cysteine, and the amino acid number refers to SEQ ID NO: 15.

In some preferred embodiments, the first constant region comprises an amino acid sequence set forth in SEQ ID NO: 13, and the second constant region comprises an amino acid sequence set forth in SEQ ID NO: 21.

As used herein, the "antigen-binding region" means that it can specifically bind to the target antigen alone or in combination with another antigen-binding region.

The "antigen" or "target antigen" as described herein may be any antigen that can be recognized and bound by the antibody, preferably a disease-associated antigen, and more preferably a cancer-associated antigen. Exemplary cancer-associated antigens include, but are not limited to, CD16, CD64, CD78, CD96, CLL1, CD116, CD117, CD71, CD45, CD71, CD123, CD138, ErbB2 (HER2/neu), carcinoembryonic antigen (CEA), epithelial cell adhesion molecule (EpCAM), epidermal growth factor receptor (EGFR), EGFR variant III (EGFRvIII), CD19, CD20, CD30, CD40, disialylganglioside GD2, ductal epithelial mucin, gp36, TAG-72, glycosphingolipid, glioma-related antigens, β-human chorionic gonadotropin, α-fetoglobulin (AFP), lectin-responsive AFP, thyroglobulin, RAGE-1, MN-CA IX, human telomerase reverse transcriptase, RU1, RU2 (AS), intestinal carboxyl esterase, mut hsp70-2, M-CSF, prostase, prostatase specific antigen (PSA), PAP, NY-ESO-1, LAGA-1a, p53, Prostein, PSMA, survival and telomerase, prostate cancer tumor antigen-1 (PCTA-1), MAGE, ELF2M, neutrophil elastase, ephrin B2, CD22, insulin growth factor (IGF1)-I, IGF-II, IGFI receptor, mesothelin, major histocompatibility complex (MHC) molecules that present tumor-specific peptide epitopes, 5T4, ROR1, Nkp30, NKG2D, tumor stromal antigen, fibronectin extra domain A (EDA) and extra domain B (EDB), tenascin-C A1 domain (TnC A1), fibroblast-associated protein (fap), CD3, CD4, CD8, CD24, CD25, CD33, CD34, CD133, CD138, Foxp3, B7-1 (CD80), B7-2 (CD86), GM-CSF, cytokine receptor, endothelial factor, BCMA (CD269, TNFRSF17), TNFRSF17 (UNIPROT Q02223), SLAMF7 (UNIPROT Q9NQ25), GPRC5D (UNIPROT Q9NZD1), FKBP11 (UNIPROT Q9NYL4), KAMP3, ITGA8 (UNIPROT P53708) and FCRL5 (UNIPROT Q68SN8).

The antigen-binding region may be derived from one or more known antibodies, including any commercially available antibody, such as FMC63, rituximab, alemtuzumab, epratuzumab, trastuzumab, bivatuzumab, cetuximab, labetuzumab, palivizumab, sevirumab, tuvirumab, basiliximab, daclizumab, infliximab, omalizumab, efatuzumab, Keliximab, siplizumab, natalizumab, clenoliximab, pemtumomab, Edrecolomab, Cantuzumab and the like. In some preferred embodiments, the antigen-binding regions are the monoclonal antibody 334 produced by a hybridoma cell 334 having the deposit number CGMCC No. 17095 (deposited at China General Microbiological Culture Collection Center, Institute of Microbiology, Chinese Academy of Sciences at No. 3, Yard 1, Beichen West Road, Chaoyang District, Beijing on Jan. 21, 2019).

In some embodiments, the first antigen-binding region comprises a heavy chain variable region of an antibody that specifically binds the target antigen, and the second antigen-binding region comprises a light chain variable region of the antibody. In some embodiments, the first antigen-binding region comprises a light chain variable region of the antibody that specifically binds the target antigen, and the second antigen-binding region comprises the heavy chain variable region of the antibody.

In some embodiments, the first antigen-binding region comprises an amino acid sequence set forth in SEQ ID NO: 22, and the second antigen-binding region comprises an amino acid sequence set forth in SEQ ID NO: 23; and alternatively, the first antigen-binding region comprises the amino acid sequence set forth in SEQ ID NO: 23 and the second antigen-binding region comprises the amino acid sequence set forth in SEQ ID NO: 22, whereby the STAR specifically binds EGFR.

In some embodiments, the first antigen-binding region comprises an amino acid sequence set forth in SEQ ID NO: 44, and the second antigen-binding region comprises an amino acid sequence set forth in SEQ ID NO: 45; and alternatively, the first antigen-binding region comprises the amino acid sequence set forth in SEQ ID NO: 45, and the second antigen-binding region comprises the amino acid sequence set forth in SEQ ID NO: 44, whereby the STAR specifically binds CD19.

In some embodiments, the first antigen-binding region comprises an amino acid sequence set forth in SEQ ID NO: 46, and the second antigen-binding region comprises an amino acid sequence set forth in SEQ ID NO: 47; and alternatively, the first antigen-binding region comprises the amino acid sequence set forth in SEQ ID NO: 47, and the second antigen-binding region comprises the amino acid sequence set forth in SEQ ID NO: 46, whereby the STAR specifically binds CD20.

In some embodiments, the first antigen-binding region comprises an amino acid sequence set forth in SEQ ID NO: 48, and the second antigen-binding region comprises an amino acid sequence set forth in SEQ ID NO: 49; and alternatively, the first antigen-binding region comprises the amino acid sequence set forth in SEQ ID NO: 49, and the second antigen-binding region comprises the amino acid sequence set forth in SEQ ID NO: 48, whereby the STAR specifically binds CD22.

In some embodiments, the first antigen-binding region comprises an amino acid sequence set forth in SEQ ID NO: 24, and the second antigen-binding region comprises an amino acid sequence set forth in SEQ ID NO: 25; and alternatively, the first antigen-binding region comprises the amino acid sequence set forth in SEQ ID NO: 25, and the second antigen-binding region comprises the amino acid sequence set forth in SEQ ID NO: 24, whereby the STAR specifically binds to GPC3.

In some embodiments, the first antigen-binding region comprises a heavy chain variable region of an antibody that specifically binds CD19, the heavy chain variable region comprises a heavy chain CDR1 set forth in SEQ ID NO: 28, a heavy chain CDR2 set forth in SEQ ID NO: 29 and a heavy chain CDR3 set forth in SEQ ID NO: 30, the second antigen-binding region comprises a light chain variable region of an antibody that specifically binds CD19, and the light chain variable region comprises a light chain CDR1 set forth in SEQ ID NO: 31, a light chain CDR2 set forth in SEQ ID NO: 32 and a light chain CDR3 set forth in SEQ ID NO: 33; or the first antigen-binding region comprises a light chain variable region of the antibody that specifically binds the CD19, the light chain variable region comprises a light chain CDR1 set forth in SEQ ID NO: 31, a light chain CDR2 set forth in SEQ ID NO: 32 and a light chain CDR3 set forth in SEQ ID NO: 33, the second antigen-binding region comprises a heavy chain variable region of the antibody that specifically binds CD19, and the second antigen-binding region comprises a heavy chain CDR1 set forth in SEQ ID NO: 28, a heavy chain CDR2 set forth in SEQ ID NO: 29 and a heavy chain CDR3 set forth in SEQ ID NO: 30, whereby the STAR specifically binds CD19.

In some embodiments, the first antigen-binding region comprises an amino acid sequence set forth in SEQ ID NO: 26, and the second antigen-binding region comprises an amino acid sequence set forth in SEQ ID NO: 27; or alternatively, the first antigen-binding region comprises the amino acid sequence set forth in SEQ ID NO: 27, and the second antigen-binding region comprises the amino acid sequence set forth in SEQ ID NO: 26, whereby the STAR specifically binds CD19.

In some embodiments, the first antigen-binding region comprises a single chain antibody (such as scFv) or a single domain antibody (such as a camel antibody) that specifically binds to the target antigen. In some embodiments, the second antigen-binding region comprises a single chain antibody (such as scFv) or a single domain antibody (such as a camel antibody) that specifically binds to the target antigen. In some embodiments, the first antigen-binding region and the second antigen-binding region bind to the same target antigen. In some embodiments, the first antigen-binding region and the second antigen-binding region bind to different regions (such as different epitopes) of the same target antigen. In some embodiments, the first antigen-binding region and the second antigen-binding region bind to different target antigens. For example, in some exemplary embodiments, the two antigen-binding regions may bind to CD19 and CD20 respectively, or CD19 and CD22 respectively, or CD38 and BCMA respectively, or PDL1 and EGFR respectively.

In some embodiments, the single chain antibody comprised in the first antigen-binding region and/or the second antigen-binding region comprises an amino acid sequence set forth in SEQ ID NO: 22 and an amino acid sequence set forth in SEQ ID NO: 23, whereby the first antigen-binding region and/or the second antigen-binding region specifically bind/binds to EGFR.

In some embodiments, the single chain antibody comprised in the first antigen-binding region and/or the second antigen-binding region comprises an amino acid sequence set forth in SEQ ID NO: 44 and an amino acid sequence set forth in SEQ ID NO: 45, whereby the first antigen-binding region and/or the second antigen-binding region specifically bind//binds to CD19.

In some embodiments, the single chain antibody comprised in the first antigen-binding region and/or the second antigen-binding region comprises an amino acid sequence set forth in SEQ ID NO: 46 and an amino acid sequence set forth in SEQ ID NO: 47, whereby the first antigen-binding region and/or the second antigen-binding region specifically bind/binds to CD20.

In some embodiments, the single chain antibody comprised in the first antigen-binding region and/or the second antigen-binding region comprises an amino acid sequence set forth in SEQ ID NO: 48 and an amino acid sequence set forth in SEQ ID NO: 49, whereby the first antigen-binding region and/or the second antigen-binding region specifically bind/binds to CD22.

In some embodiments, the single chain antibody comprised in the first antigen-binding region and/or the second antigen-binding region comprises an amino acid sequence set forth in SEQ ID NO: 24 and an amino acid sequence set forth in SEQ ID NO: 25, whereby the first antigen-binding region and/or the second antigen-binding region specifically bind/binds to GPC3.

In some embodiments, the single chain antibody comprised in the first antigen-binding region and/or the second antigen-binding region comprises a heavy chain variable region and a light chain variable region, the heavy chain variable region comprises a heavy chain CDR1 set forth in SEQ ID NO: 28, a heavy chain CDR2 set forth in SEQ ID NO: 29 and a heavy chain CDR3 set forth in SEQ ID NO: 30, and the light chain variable region comprises a light chain CDR1 set forth in SEQ ID NO: 31, a light chain CDR2 set forth in SEQ ID NO: 32 and a light chain CDR3 set forth in SEQ ID NO: 33, whereby the first antigen-binding region and/or the second antigen-binding region specifically bind/binds to CD19.

In some embodiments, the single chain antibody comprised in the first antigen-binding region and/or the second antigen-binding region comprises an amino acid sequence set forth in SEQ ID NO: 26 and an amino acid sequence set forth in SEQ ID NO: 27, whereby the first antigen-binding region and/or the second antigen-binding region specifically bind/binds to CD19.

In another aspect, the invention provides a synthetic T-cell receptor antigen receptor (STAR) comprising an α chain and a β chain, the α chain comprises a first antigen-binding region and a first constant region, and the β chain comprises a second antigen-binding region and a second constant region, wherein the first constant region is a native T-cell receptor α chain constant region or a variant of the native T-cell receptor α chain constant region as disclosed herein, wherein the second constant region is a native T-cell receptor β chain constant region or a variant of the native T-cell receptor β chain constant region as disclosed herein, and wherein the first antigen-binding region and the second antigen-binding region specifically bind to different target antigens or different regions of the same target antigen.

In some embodiments, the first antigen-binding region and/or the second antigen-binding region comprise/comprises a single chain antibody (such as scFv) or a single domain antibody (such as a camel antibody) that specifically binds to the target antigen.

In some embodiments, the single chain antibody comprised in the first antigen-binding region and/or the second antigen-binding region comprises an amino acid sequence set forth in SEQ ID NO: 22 and an amino acid sequence set forth in SEQ ID NO: 23, whereby the first antigen-binding region and/or the second antigen-binding region specifically bind/binds to EGFR.

In some embodiments, the single chain antibody comprised in the first antigen-binding region and/or the second antigen-binding region comprises an amino acid sequence set forth in SEQ ID NO: 44 and an amino acid sequence set forth in SEQ ID NO: 45, whereby the first antigen-binding region and/or the second antigen-binding region specifically bind/binds to CD19.

In some embodiments, the single chain antibody comprised in the first antigen-binding region and/or the second antigen-binding region comprises an amino acid sequence set forth in SEQ ID NO: 46 and an amino acid sequence set forth in SEQ ID NO: 47, whereby the first antigen-binding region and/or the second antigen-binding region specifically bind/binds to CD20.

In some embodiments, the single chain antibody comprised in the first antigen-binding region and/or the second antigen-binding region comprises an amino acid sequence set forth in SEQ ID NO: 48 and an amino acid sequence set forth in SEQ ID NO: 49, whereby the first antigen-binding region and/or the second antigen-binding region specifically bind/binds to CD22.

In some embodiments, the single chain antibody comprised in the first antigen-binding region and/or the second antigen-binding region comprises an amino acid sequence set forth in SEQ ID NO: 24 and an amino acid sequence set forth in SEQ ID NO: 25, whereby the first antigen-binding region and/or the second antigen-binding region specifically bind/binds to GPC3.

In some embodiments, the single chain antibody comprised in the first antigen-binding region and/or the second antigen-binding region comprises a heavy chain variable region and a light chain variable region, the heavy chain variable region comprises a heavy chain CDR1 set forth in SEQ ID NO: 28, a heavy chain CDR2 set forth in SEQ ID NO: 29 and a heavy chain CDR3 set forth in SEQ ID NO: 30, and the light chain variable region comprises a light chain CDR1 set forth in SEQ ID NO: 31, a light chain CDR2 set forth in SEQ ID NO: 32 and a light chain CDR3 set forth in SEQ ID NO: 33, whereby the first antigen-binding region and/or the second antigen-binding region specifically bind/binds to CD19.

In some embodiments, the single chain antibody comprised in the first antigen-binding region and/or the second antigen-binding region comprises an amino acid sequence set forth in SEQ ID NO: 26 and an amino acid sequence set forth in SEQ ID NO: 27, whereby the first antigen-binding region and/or the second antigen-binding region specifically bind/binds to CD19.

In some exemplary embodiments, the two antigen-binding regions may bind to CD19 and CD20 respectively, or CD19 and CD22 respectively, or CD38 and BCMA respectively, or PDL1 and EGFR respectively.

In another aspect, the invention provides an isolated polynucleotide comprising a nucleotide sequence encoding the α chain and/or the β chain of the synthetic T-cell receptor antigen receptor (STAR) of the invention.

In some embodiments, the polynucleotide comprises, in one reading frame, i) the nucleotide sequence encoding the α chain, ii) the nucleotide sequence encoding the β chain, and iii) the nucleotide sequence encoding a self-cleaving peptide located between i) and ii). The nucleotide sequence encoding the α chain may be located at the 5' terminal or the 3' terminal of the nucleotide sequence encoding the β chain.

"Self-cleaving peptide" as used herein means a peptide that can achieve self-cleavage within a cell. For example, the self-cleaving peptide may comprise a protease recognition site so as to be recognized and specifically cleaved by a protease within the cell.

Alternatively, the self-cleaving peptide may be a 2A polypeptide. 2A polypeptides are a class of short peptides from viruses whose self-cleavage occurs during translation. When the 2A polypeptide is used for connecting two different target proteins to be expressed in the same reading frame, the two target proteins are almost generated at the ratio of 1:1. Commonly used 2A polypeptides can be P2A from porcine techovirus-1, T2A from Thosea asigna virus, E2A from equine rhinitis A virus and F2A from foot-and-mouth disease virus. Among them, the cleavage efficiency of P2A is the highest, and therefore the P2A is preferred. A variety of functional variants of these 2A polypeptides are also known in the art, and such variants may also be used in the present invention.

In another aspect, the present invention provides an expression vector comprising the polynucleotide of the present invention operably linked to a regulatory sequence.

The "expression vector" of the present invention may be a linear nucleic acid segment, a circular plasmid and a viral vector, or may be an RNA (such as an mRNA) capable of being translated. In some preferred embodiments, the expression vector is viral vectors, such as a lentiviral vector.

A "regulatory sequence" and a "regulatory element" are used interchangeably to refer to nucleotide sequences located upstream (5' non-coding sequences), intermediate, or downstream (3' non-coding sequences) of a coding sequence, which influence the transcription, RNA processing or stability, or translation of the associated coding sequence. The expression regulatory element refers to nucleotide sequences capable of controlling transcription, RNA processing or stability, or translation of the nucleotide sequence of interest. The regulatory sequence may include, but is not limited to, promoters, translation leader sequences, introns, enhancers and polyadenylation recognition sequences.

As used herein, the term "operably linked" means that the regulatory element (e.g., but not limited to, a promoter sequence, a transcription termination sequence, etc.) is linked to a nucleic acid sequence (e.g., a coding sequence or an open reading frame) such that transcription of the nucleotide sequence is controlled and regulated by the transcriptional regulatory element. Techniques for operably linking the regulatory element region to the nucleic acid molecule are known in the art.

In another aspect, the invention provides a method of preparing a therapeutic T cell, which comprises the step of expressing the synthetic T-cell receptor antigen receptor (STAR) of the invention in the T cell. In some embodiments, the method comprises the step of introducing the polynucleotide of the invention or the expression vector of the invention into the T cell.

In another aspect, the invention provides a therapeutic T cell comprising the synthetic T-cell receptor antigen receptor (STAR) of the invention, or obtained by the method of the invention.

The T cell of the invention can be obtained by various non-limiting methods from a number of non-limiting sources, including peripheral blood mononuclear cells, bone marrow, lymph node tissue, cord blood, thymus tissue, ascites, pleural effusion, spleen tissue and tumors. In some embodiments, the cells may be derived from a healthy donor or from a patient diagnosed with cancer. In some embodiments, the cells may be parts of a mixed population of cells presenting different phenotypic characteristics. For example, the T cells can be obtained by isolating peripheral blood mononuclear cells (PBMC) and then conducting activation and expansion with specific antibodies.

In some embodiments of the aspects of the present invention, the T cell is derived from an autologous cell of a subject. As used herein, "autologous" refers to that cells, cell lines, or cell populations used to treat the subject are derived from the subject. In some embodiments, the T cell is derived from heterologous cells, e.g., from a donor compatible with the subject's human leukocyte antigen (HLA). Standard schemes can be used to convert cells from a donor into non-alloreactive cells and to replicate the cells as required, generating cells that can be administered to one or more patients.

In another aspect, the invention provides a pharmaceutical composition comprising the therapeutic T cell of the invention and a pharmaceutically acceptable carrier.

As used herein, the "pharmaceutically acceptable carrier" includes any and all solvents, dispersion media, coatings, antibacterial and antifungal agents, isotonic agents, absorption delaying agents and the like that are physiologically compatible. Preferably, the carrier is suitable for intravenous, intramuscular, subcutaneous, parenteral, spinal or epidermal administration (such as by injection or infusion).

In another aspect, the present invention provides use of the therapeutic T cell of the invention or the pharmaceutical composition of the invention in the manufacture of a medicament for treatment of a disease, such as cancer, in a subject.

As used herein, the "subject" refers to an organism suffering from or susceptible to suffering from the disease, such as cancer, that can be treated by the cell, method, or pharmaceutical composition of the invention. Non-limiting examples include human, cow, rat, mouse, dog, monkey, goat, sheep, deer, and other non-mammals. In a preferred embodiment, the subject is a human.

In another aspect, the present invention provides a method of treating the disease, such as cancer, in a subject, which comprises the step of administering a therapeutically effective amount of therapeutic T cell of the present invention or pharmaceutical composition of the present invention to the subject.

As used herein, "therapeutically effective amount" or "therapeutically effective dose" or "effective amount" refers to an amount of a substance, compound, material or cell that is at least sufficient to produce a therapeutic effect after administration to a subject. Thus, it is an amount necessary to prevent, cure, ameliorate, arrest or partially arrest the symptoms of a disease or condition. For example, the "effective amount" of cells or pharmaceutical composition of the invention preferably results in a decrease in the severity of the symptoms of the disease, an increase in the frequency and duration of the asymptomatic phase of the disease, or prevention of damage or disability caused by the disease. For example, for the treatment of a tumor, an "effective amount" of cells or pharmaceutical composition of the invention preferably inhibits tumor cell growth or tumor growth relative to a subject not receiving the treatment by at least about 10%, preferably at least about 20%, preferably at least about 30%, more preferably at least about 40%, more preferably at least about 50%, more preferably at least about 60%, more preferably at least about 70%, more preferably at least about 80%. The ability to inhibit tumor growth can be evaluated in animal model systems which can be used to predict the therapeutic effect on human tumors. Alternatively, it can also be evaluated by examining the ability to inhibit tumor cell growth, which can be determined in vitro by assays well known to those skilled in the art.

Actual dosage levels of the cells in the pharmaceutical compositions of the invention may be varied so as to obtain an amount of the cells which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

Administration of the therapeutic T cells or pharmaceutical composition or medicament according to the invention may be carried out in any convenient manner, including by injection, infusion, implantation, or transplantation. Administration of the cells or composition described herein can be by intravenous, intralymphatic, intradermal, intratumoral, intramedullary, intramuscular, or intraperitoneal administration. In one embodiment, the cells or composition of the invention can be preferably administered by intravenous injection.

In embodiments of various aspects of the present invention, the cancer is selected from the group consisting of lung cancer, ovarian cancer, colon cancer, rectal cancer, melanoma, kidney cancer, bladder cancer, breast cancer, liver cancer, lymphoma, hematological malignancies, head and neck cancers, glial tumor, stomach cancer, nasopharyngeal cancer, throat cancer, cervical cancer, uterine body tumor and osteosarcoma. Examples of other cancers that can be treated with the method or pharmaceutical composition of the present invention include: bone cancer, pancreatic cancer, skin cancer, prostate cancer, skin or intraocular malignant melanoma, uterine cancer, anal cancer, testicular cancer, fallopian tube cancer, endometrial cancer, vaginal cancer, vaginal cancer, Hodgkin's disease, non-Hodgkin's lymphoma, esophageal cancer, small intestine cancer, endocrine system cancer, thyroid cancer, parathyroid cancer, adrenal cancer, soft tissue sarcoma, urethral cancer, penile cancer, chronic or acute leukemia (including acute myeloid leukemia, chronic myeloid leukemia, acute lymphocytic leukemia, and chronic lymphocytic leukemia), childhood solid tumors, lymphocytic lymphoma, bladder cancer, kidney or ureteral cancer, renal pelvis cancer, central nervous system (CNS) tumor, primary CNS lymphoma, tumor angiogenesis, spinal tumor, brainstem glioma, pituitary adenoma, Kaposi's sarcoma, epidermal carcinoma, squamous cell carcinoma, T cell lymphoma, and environmentally induced cancers, including asbestos-induced cancers, and combinations of the cancers.

EXAMPLES

Figure 1B:
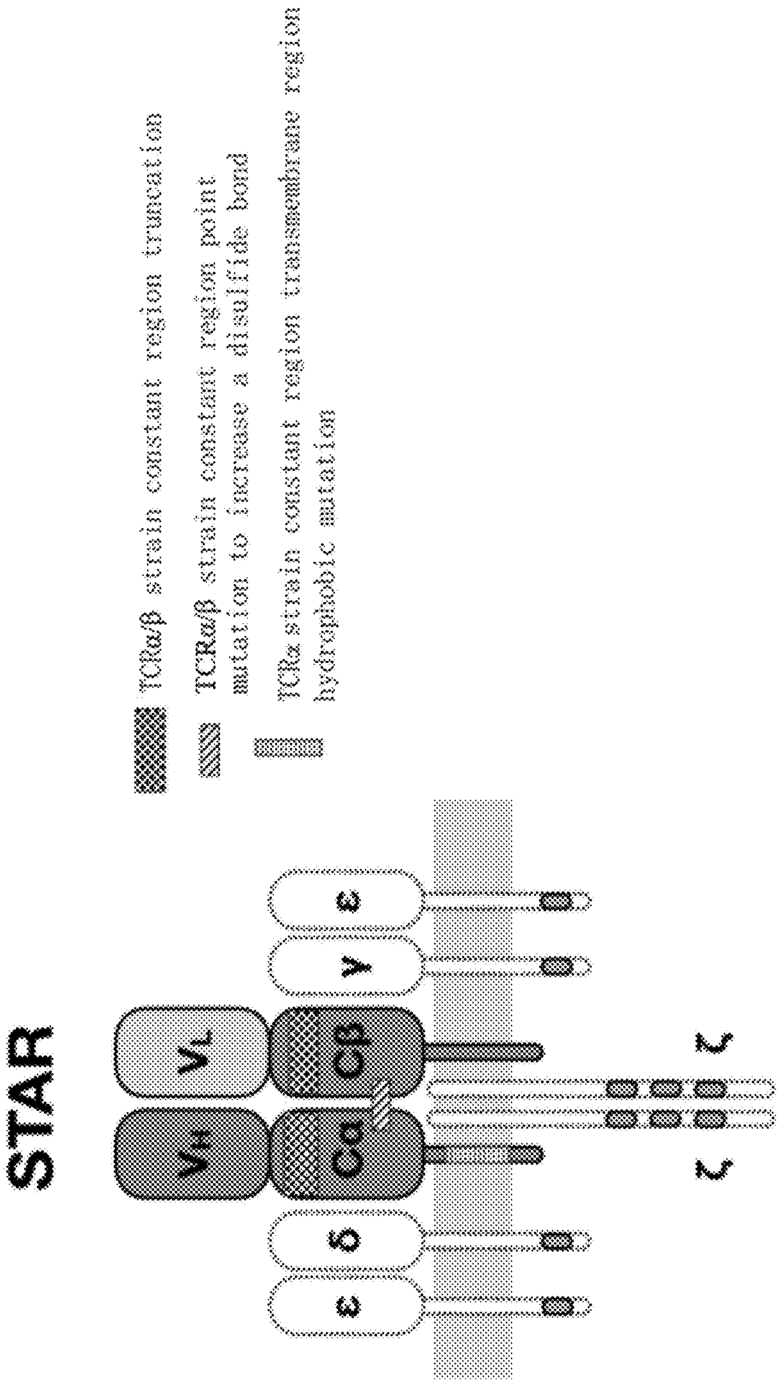
Figure 1C:
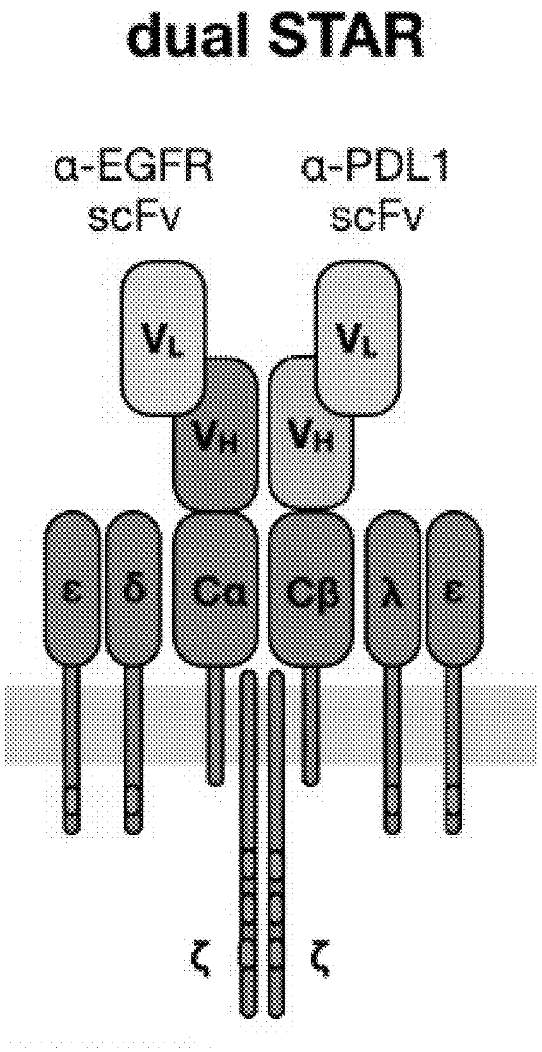

Example 1. Design of Constant Region Domains of an STAR and a Mutant Thereof 1.1 Design of a Prototype of the STAR A secreted antibody (Ab) or B cell receptor (BCR) produced by B cells shares great similarity to a T-cell receptor (TCR) in gene structure, protein structure and spatial conformation. Both the antibody and the TCR are composed of variable and constant regions, where the variable region plays a role in antigen recognition and binding, and the constant region domain play a role in structural interaction and signal transduction. By replacing the variable region of TCR $\alpha$ and $\beta$ chains (or TCR $\gamma$ and $\delta$ chains) with a heavy variable region (VH) and a light (VL) chain variable region of an antibody, a synthetic chimeric molecule called the synthetic T-cell receptor and antibody receptor (STAR) can be constructed, and the structure is shown in FIG. 1.

The STAR molecule has two chains, the first chain is obtained by fusing an antigen recognition sequence (e.g., the heavy chain variable region VH of the antibody) to the constant region of the T-cell receptor $\alpha$ chain (TCR $\alpha$) (C $\alpha$, human TCRaC-WT, SEQ ID NO: 1), and the second chain is obtained by fusing an antigen recognition sequence (e.g., the light chain variable region VL of the antibody) to the constant region of the T-cell receptor $\beta$ chain (TCR $\beta$) (O $\beta$, human TCRbC-WT, SEQ ID NO: 14). The antigen recognition domain (such as VH, VL or scFv) and the constant region domain (TCR α, β, γ and δ constant regions) in the construct can be arranged and combined to form a plurality of constructs with different configurations but similar functions.

After the first chain and the second chain of the STAR molecule are expressed in T cells, the first chain and the second chain of the STAR molecule can be combined with endogenous CD3εδ, CD3γε and CD3ζζ chains of the cells in an endoplasmic reticulum to form an 8-subunit complex, and the complex is displayed on the surface of a cell membrane in a complex mode. An immunoreceptor tyrosine-based activation motif (ITAM) is a sequence motif having the signal transduction effect in the TCR molecule, a conserved sequence of which is YxxL/V. The intracellular region of the CD3ε, δ, γ and ε chains contains one ITAM sequence, and the intracellular region of the CD3 ζ chain contains three ITAM sequences, so that the complete STAR complex contains 10 ITAM sequences in total. When the antigen recognition sequence of the STAR is combined with a specific antigen, the intracellular ITAM sequences are gradually phosphorylated, so that a downstream signal path is activated, transcription factors such as NF-κB, NFAT and AP-1 are activated, the T cells are triggered to be activated, and an effector function is generated.

1.2 Design of a Mouse-Derived STAR

The design of the prototype of the STAR uses constant region sequences of TCR α/β chains (or TCR γ and δ chains) of human origin. The constant region sequences of human, primate and mouse TCR α/β chains (mouse TCRaC-WT, SEQ ID NO: 2 and mouse TCRbC-WT (SEQ ID NO: 15) (or TCR γ and δ chains) are high in function conservatism, and key amino acid sequences are identical, so they can be substituted for each other.

Figure 2:
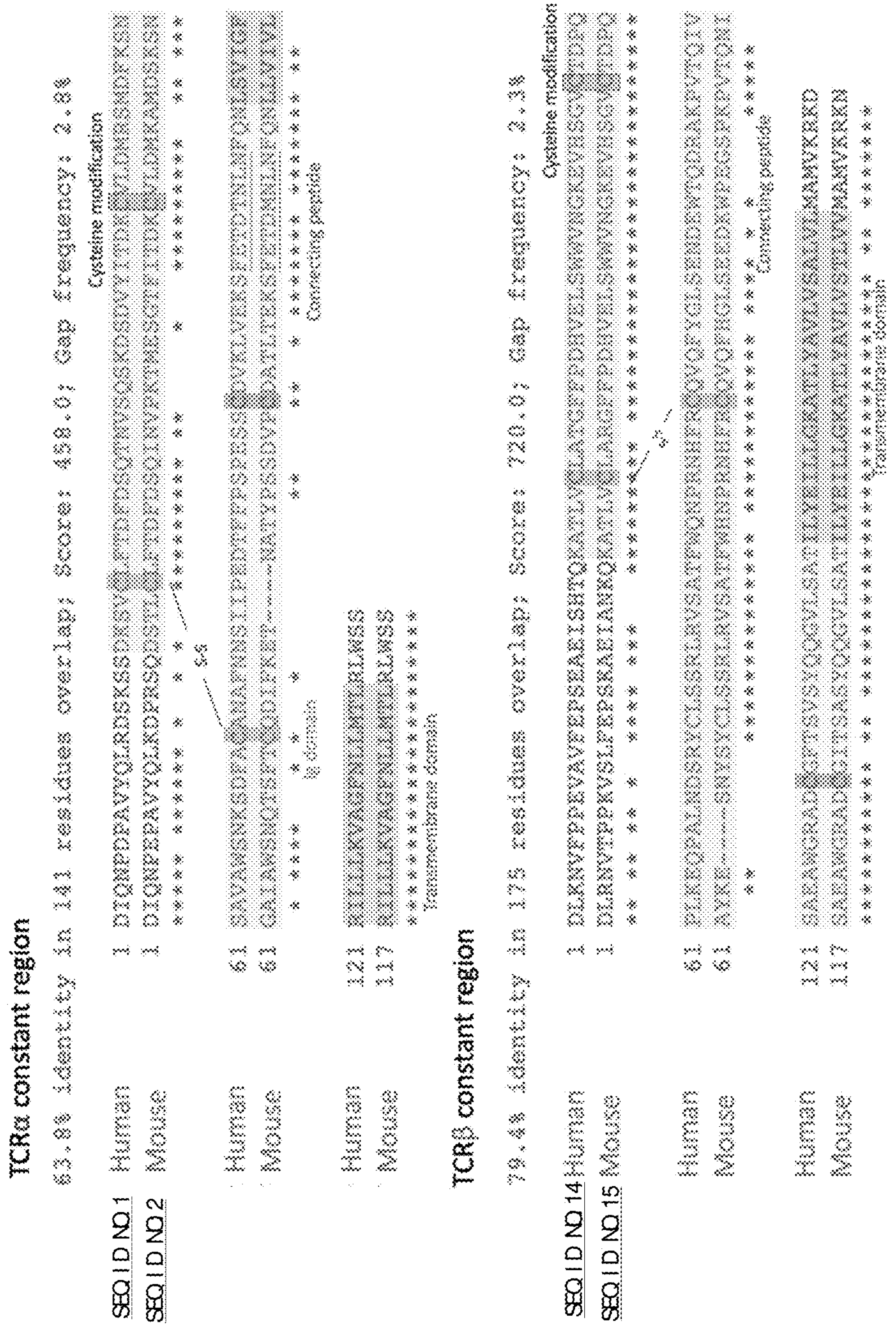
FIG. 2 shows sequence alignment results of constant regions of α chains and β chains of human and mouse T-cell receptors.
Figure 5B:
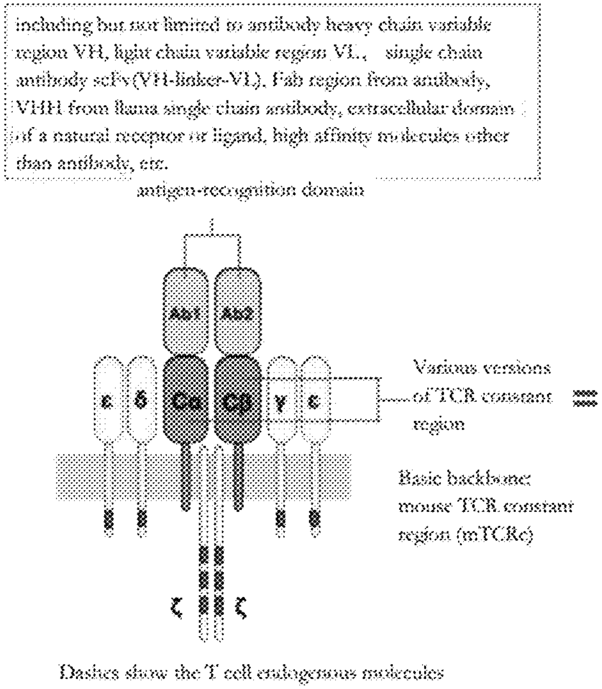
FIG. 5 shows constant region mutants combining different modifications.

Once transduced into the T cells, the STAR molecule would mis-pair with the endogenous TCR of the T cells via the constant regions. This mispairing problem reduces the efficiency with which the STAR molecule is properly paired and impairs their functions on one hand, and increases the potential for mispairing to generate unknown specificity and increases safety risks on the other hand. In order to solve the problem, the constant regions of the STAR molecule were substituted with mouse sequences, so that the function of the STAR molecule after being transferred into the human T cells is enhanced. An alignment of human and mouse sequences is shown in FIG. 2.

1.3 Design of Modifications at the N-Terminals of the Constant Regions of the STAR In order to further optimize the design of the STAR molecule, the specific sequence in the STAR molecule was modified, and one modification scheme is that the N-terminals of the constant regions of the STAR molecule were deleted. 18 amino acids at the N-terminal of the TCR α chain constant region were deleted (the mouse sequence is DIQNPEPAVYQLKDPRSQ, SEQ ID NO: 3) (a generated constant region sequence is mouse TCRaC-N.DLT, SEQ ID NO: 4); and 25 amino acids at the N-terminal of the TCR β chain constant region were deleted (the mouse sequence is DLRNVTPPKVSLFEPSKAEIANKQK, SEQ ID NO: 16) (a generated constant region sequence is mouse TCRbC-N.DLT, SEQ ID NO: 17). These two regions are located of the N-terminals of the constant regions, do not belong to an Ig-like Cl type domain, nor are they involved in intramolecular disulfide bond formation, but function primarily as a hinge, which has an impact on the function of the STAR, for which different deletion schemes are designed. According to the invention, the specific sequences of the constant regions were rearranged to obtain a better effect. Rearrangement means that partial sequences were deleted while humanized mutation was made to partial sequences. This regional modification has the following advantages: firstly, the functional optimization of a hinge region can reduce mispairing of the STAR and the endogenous TCR; and secondly, the optimized STAR molecule size is more similar to that of a native TCR, which facilitates binding of co-stimulatory molecules, formation and stabilization of immunological synapse, and subsequent effector functions of the T cells.

The significance of the humanized mutation is to minimize non-human sequences in the STAR molecule while ensuring the function of the STAR molecule to circumvent the possibility that STAR-T cells are rejected by receptors in clinical applications to the greatest extent. Specific rearrangement schemes are set forth below.

Scheme for rearrangement of 18 amino acids (the mouse sequence is DIQNPEPAVYQLKDPRSQ) at the N-terminal of the TCR α chain constant region:

FIG. 3 shows an alignment of the 18 amino acids at the N-terminal of the mouse TCR α chain constant region with the human sequence, UserSeq1 is the human sequence, and UserSeq2 is the mouse sequence. Through amino acid property analysis, it was found that the mouse-derived sequence and the human-derived sequence both belong to identical-property amino acid substitutions at E6D, K13R, R16K and Q18S sites, and belong to non-polar amino acids to be substituted into polar amino acids at the P15S site, so that the properties of proteins near the site are not conserved, and the modification can be made without affecting functions. In conclusion, amino acid sequences at positions 1-14 at the N-terminal of the mouse TCR α chain constant region were retained and humanized, and amino acids at positions 15-18 were deleted to generate mouse TCRaC-N.Rec-4, SEQ ID NO: 5.

In addition, to account for the hinge effect of this region, all truncations may have an impact on the effect, amino acids at positions 1~4 at the N-terminal of the mouse TCR α chain constant region were deleted, amino acids at positions 5-18 were humanized, the modification was called as mouse TCRaC-N.Rec-1, and a generated constant region sequence is SEQ ID NO: 34; amino acids at positions 1-8 at the N-terminal of the mouse TCR α chain constant region were deleted, amino acids at positions 9-18 were humanized, the modification was called as mouse TCRaC-N.Rec-2, and a generated constant region sequence is SEQ ID NO: 35; and amino acids at positions 1-12 at the N-terminal of the mouse TCR α chain constant region were deleted, and amino acids at positions 13-18 were humanized, and a generated constant region sequence was mouse TCRaC-N.Rec-3, SEQ ID NO: 36. As a control, random rearrangement of amino acids at positions 1-18 at the N-terminal of the mouse TCR α chain constant region was also performed, and a generated constant region sequence is mouse TCRaC-N.rRec, SEQ ID NO: 40.

Scheme for rearrangement of 25 amino acids (the mouse sequence is DLRNVTPPKVSLFEPSKAEIANKQK) at the N-terminal of the TCR β chain constant region:

FIG. 4 shows an alignment of the 25 amino acids at the N-terminal of the mouse TCR β chain constant region with the human sequence, UserSeq1 is the human sequence, and UserSeq2 is the mouse sequence. Through amino acid property analysis, it was found that mouse-derived and human-derived sequences only belong to identical-property amino acid substitutions at sites R3K and L12V, and all belong to substitutions with different amino acid properties at sites T6F, K8E, D11A, K17E, A21S, N22H and K23T, so that the properties of proteins near the sites are not conserved, and the modification can be made without affecting functions. In conclusion, amino acid sequences at positions 1-16 at the N-terminal of the mouse TCR β chain constant region were reserved and humanized, and amino acids at positions 17 and 21-25 were deleted, so that a generated constant region sequence is mouse TCRbC-N.Rec-4 (SEQ ID NO: 18).

In addition, to account for the hinge effect of this region, all truncations may have an impact on the effect, amino acids at positions 1-6 at the N-terminal of the mouse TCR β chain constant region were deleted, amino acids at positions 13-25 were humanized, and a generated constant region sequence is mouse TCRbC-N.Rec-1, SEQ ID NO: 37; amino acids at positions 1-12 at the N-terminal of the mouse TCR β chain constant region were also deleted, amino acids at positions 13-25 are humanized, and a generated constant region sequence is mouse TCRbC-N.Rec-2, SEQ ID NO: 38; and amino acids at positions 1-18 at the N-terminal of the mouse TCR β chain constant region were also deleted, amino acids at positions 19-25 were humanized, and a generated constant region sequence is mouse TCRbC-N.Rec-3, SEQ ID NO: 39. As a control, a random rearrangement of amino acids at positions 1-25 at the N-terminal of the mouse TCR β chain constant region was also performed to generate a constant region sequence of mouse TCRbC-N.rRec, SEQ ID NO: 41.

1.4 Design of Modification of C-Terminals of the Constant Regions of the STAR

In the invention, 15 amino acids at the C-terminal of the mouse TCR α chain constant region were deleted, so that the constant region sequence is mouse TCRaC-C.DLT (SEQ ID NO: 42).

In the invention, 15 amino acids at the C-terminal of the mouse TCR β chain constant region were deleted, so that the constant region sequence is mouse TCRbC-C.DLT (SEQ ID NO: 43).

1.5 Design of Cysteine Point Mutation of the STAR to Introduce Intermolecular Disulfide Bonds To further optimize the design of the STAR molecule, the specific sequences in the STAR molecule were modified, one modification scheme was to conduct cysteine point mutation to the STAR molecule to introduce the intermolecular disulfide bonds to enhance pairing between the two chains of the STAR molecule and reduce mispairing with the endogenous TCR. The specific scheme is set forth below.

In the TCR α chain constant region, threonine T at position 48 was mutated to cysteine C (generated constant region sequences are human TCRaC-Cys, SEQ ID NO:6 and mouse TCRaC-Cys, SEQ ID NO:7), in the TCR β chain constant region, serine S at position 56 was mutated to cysteine C (generated constant region sequences are human TCRbC-Cys, SEQ ID NO: 19 and mouse TCRbC-Cys, SEQ ID NO: 20). The two newly added cysteines would form the disulfide bonds between the two chains of the STAR, the mispairing between the two chains of the STAR and the endogenous TCR chain was reduced, the STAR molecule was helped to form a more stable complex, and then better functionality was obtained.

1.6 Design of Hydrophobic Amino Acid Substitutions in the Transmembrane Region of the STAR In order to further optimize the design of the STAR molecule, the present invention modifies the specific sequence in the STAR molecule. One modification scheme is to conduct hydrophobic amino acid substitutions in the transmembrane region of the STAR molecule to increase the stability of the STAR molecule and help it to play more lastingly functions. The specific scheme is described as follows.

3 amino acid sites were mutated in a 111 to 119 amino acid area of the transmembrane region of the TCR α chain constant region, serine S at position 112 was changed to leucine L, and methionine M at position 114 was changed to isoleucine I, and glycine G at position 115 was changed to pyrimidine V. The overall amino acid sequence of this region was changed from LSVMGLRIL to LLVIVLRIL, this modification was called mouse TCRaC-TM9, and a generated constant region sequence is SEQ ID NO: 9. This design increases the hydrophobicity of the transmembrane region and counteracts the instability caused by positive charges carried by the TCR transmembrane region, so that the STAR molecule can exist more stably on the cell membrane and thus obtain better functions.

1.7 Combination of N-Terminal Modification, Cysteine Modification and Transmembrane region modification The inventors combined the above-mentioned N-terminal modification, cysteine modification and transmembrane region modification, and designed mouse TCRaC-Cys-N.Rec-1 (SEQ ID NO: 11), mouse TCRaC-TM9-N. Rec-1 (SEQ ID NO: 12), mouse TCRaC-Cys-TM9 (SEQ ID NO: 10), mouse TCRaC-Cys-TM9-N.Rec-1 (SEQ ID NO: 13), and mouse TCRbC-Cys-N.Rec-1 (SEQ ID NO: 21). 1.8 Exchange arrangements and combinations of variable and constant regions of the STAR The STAR molecule can be divided into two parts: a variable region domain and a constant region domain. The variable region domain consists of an amino acid sequence with antigen recognition ability, and is generally composed of the following classes of molecules: an antibody light chain variable region, an antibody heavy chain variable region, a single-chain antibody (scFv), a ligand-receptor binding region, Nanobody, etc. The constant region domain consists of a TCR constant region or related sequences that have the ability to integrate with the CD3 subunit, typically including constant regions of TCR α, β, γ and δ chains.

The antigen recognition domain and the constant region domain in an STAR construct can be arranged and combined to form a variety of constructs with different configurations but similar functions. Some possible arrangements and combinations are shown in the table below:

| | STAR-α chain | | STAR-β chain | |
|---|---|---|---|---|
| Serial number | Antigen recognition region | Constant region | Antigen recognition region | Constant region |
| 1 | VH | Cα | VL | Cβ |
| 2 | VL | Cα | VH | Cβ |
| 3 | VH | Cγ | VL | Cδ |
| 4 | VL | Cγ | VH | Cδ |
| 5 | ScFv1 | Cα | ScFv2 | Cβ |
| 6 | ScFv2 | Cα | ScFv1 | Cβ |
| 7 | ScFv1 | Cγ | ScFv1 | Cδ |
| 8 | ScFv2 | Cγ | ScFv2 | Cδ |
| 9 | Ligand1 | Cα | Ligand2 | Cβ |
| 10 | Ligand2 | Cα | Ligand1 | Cβ |
| 11 | Ligand1 | Cγ | Ligand2 | Cδ |
| 12 | Ligand2 | Cγ | Ligand1 | Cδ |
| 13 | VH | Cα | scFvl | Cβ |
| 14 | VL | Cα | scFvl | Cβ |
| 15 | scFv1 | Cα | Ligand1 | Cβ |
| 16 | VH | Cα | Ligand1 | Cβ |
| 17 | VL | Cα | Ligand1 | Cβ |

Example 2. Design of an Antigen Recognition Domain of an STAR

1) Target Selection

STAR target selection is primarily achieved by a bank of gene expression, and in general, the expression level of suitable STAR targets generally has high expression or specific expression on diseases or associated cells compared to normal cells. After the suitable targets are determined, the antigen recognition domain for recognizing the targets is generally an antibody, SCFV, VHH or an antigen corresponding receptor, etc., A heavy chain variable region (VH), a light chain variable region (VL), an alpaca single chain antibody (VHH), and a receptor and a ligand of the antibody can be obtained by immunizing mice, alpacas, sequencing or published sequences. An obtained mouse-derived or alpaca sequence generally needs to be subjected to humanization and codon optimization so as to be more beneficial to expression and function in human cells. After a suitable sequence is obtained, the obtained sequence is connected to a lentivirus or retrovirus vector, whether vector construction is correct or not is detected through a sequencing method, then the vector is expressed in somatic cells through virus packaging and infection, and tag proteins RFP, GFP, MYC, HIS and the like are used for detecting STAR protein expression, membrane loading, antigen binding and the like. Useful targets include, but are not limited to, GPC3, EGFR VIII, CD22, CD20, MSLN, GD2, LIRB4, ROR1, Cllaudin 18.2, CD7, CD47 and CD24.

2) Table of Target Cell Lines and Tool Cell Lines

In the invention, a plurality of target cell lines were used for explaining the function of the STAR, and target cells obtained luciferase genes through a genetic engineering means, so that the in-vitro function detection was facilitated. Luciferase is a common substance for researching cell functions, the enzyme activity is judged by adding a luciferase substrate into a system, and the luciferase activity is closely related to expression of o the target genes, binding strength, cell number and the like. In the invention, the target cell lines for stably expressing the luciferase were established, and the quantity of target cells was indicated by the quantity of luciferase, so that the killing function of functional cells was indicated. Specific cells were as follows:

| Name of cell lines | Target spots | Corresponding cancers/ diseases or functions |
|---|---|---|
| A431 | EGFR | Skin cancer |
| A549 | EGFR | Lung cancer |
| B16/htEGFR | EGFR | Melanoma |
| HepG2 | GPC3 | Liver cancer |
| HUH7 | GPC3 | Liver cancer |
| RAJI | CD19 | Lymphoma/leukemia |
| RAJI-CD19KO | CD19- | Lymphoma/leukemia |
| RAJI-CD20KO | CD20- | Lymphoma |
| RAJI-CD22KO | CD22- | Lymphoma |
| Jurkat | | Function test |
| Jurkat Clone 5 (JC5) | | Function test/virus titer test |

3) Selection of the Antigen Recognition Domain (Antibody, scFv, Fab, VHH, Etc.)

The antigen recognition domain may be derived from the antibody that recognizes an antigen, a single chain variable region of the antibody, a variable region, a nanobody, a receptor for antigen recognition and the like. In the design of the STAR, viruses are the main route for T cell transformation, and lentiviral or retroviral packaging is related to the size of packaging, so smaller antibody recognition units are favored, for example, the antibody single chain variable region and the nanobody are better choices in terms of size. Aiming at the same antigen, the existing antibody is one of the ways of widely screening the antibody recognition domain as the prior art, and meanwhile, a brand-new antibody for recognizing the antigen was obtained through the technologies of constructing a fully-humanized antibody library by a phage library, affinity optimization, mouse hybridoma screening, alpaca monoclonal antibody screening, humanization and the like. In addition, the receptor of the antigen as a specific molecule capable of recognizing the antigen is one of the main choices of the antigen recognition domain.

Example 3. Plasmid Construction of an STAR and a Mutant Thereof

1) Plasmid Source

Vectors used in the invention, including lentivirus vectors, retrovirus vectors, protein expression vectors, phagemids, lentivirus packaging plasmids, retrovirus packaging plasmids and the like, are all purchased from commercial companies or synthesized by commercial companies, full-length sequences of the vectors are obtained, and clear enzyme cutting sites are known.

2) Fragment Source Gene segments adopted in the invention comprise a signal peptide, an antibody binding region, a hinge region, a TCR constant region, tag proteins and the like which were all synthesized by the commercial companies. Corresponding functional sequences were obtained by connecting one or more target fragments in a primer synthesis PCR manner.

3) Plasmid Construction and Sequencing Method

The lentiviral vector used in the method is pHAGE-EF1a-GFP, a pHAGR-EF1A-WPRE-AMP vector was obtained through restriction endonuclease Not I/Cla I, a fragment gene was obtained through synthesis and the PCR method, and a complete vector was obtained through a homologous recombination method under the action of Gibsson/NEBuilder and other recombinases. The retroviral vector RVKM-CMV-GFP obtained a vector fragment by restriction enzyme Xho I/BamH I, while an insert fragment gene was obtained by synthesis and the PCR method, and the vector and the fragment were jointed by the homologous recombination method. A prokaryotic expression vector was a pET-28a vector, used restriction endonuclease sites were XhoI and NcoI, an eukaryotic expression vector was PVRC8400, used restriction endonuclease sites were XhoI and XbaI, primers were designed according to human antigen genes, restriction endonuclease digestion sites were added to the two ends of the primers, truncated his-tags of antigen extracellular segments and C segments were amplified from target cell well genes to be used for subsequent purification. The primers were respectively designed according to a sense strand and an antisense strand of a sticky end of an enzyme digestion product by using a sticky end PCR, the primers were respectively subjected to PCR to be subjected to one-step recombination connection with the vectors after enzyme digestion, 5 μL of connection products were added into 50 μL of DH5a competent cells after connection for transformation, and inversion in a 37 DEG C incubator, cultured for 12-16 hours.

4) Plasmid Extraction Method

An alkaline lysis method was adopted for plasmid extraction, and after plasmid extraction, the plasmid concentration was detected through 260 nm light absorption. Plasmids with a correct primary sequencing result need to be transformed and selected for monoclines to be subjected to extraction, and whether the plasmids are correct or not was identified through enzyme digestion.

The plasmid pHAGE-EF1A-IRES-RFP was obtained by the above method; the constant regions are various pHAGE-EFIA-Cetux-VL-TCRaC-P2A-VH-TCRbC-IRES-RFP and pHAGE-EF1A-GC33-VL-TCRaC-P2A-VH-TCRbC-IRES-RFP plasmids of TCRa/bC-WT (including TCRaC-WT and TCRbC-WT), TCRa/bC-N.DLT (including TCRaC-N.DLT and TCRbC-N.DLT), TCRa/bC-C.DLT (including TCRaC-C.DLT and TCRbC-CDLT), TCRa/bC-N.Rec-1 (including TCRaC-N.Rec-1 and TCRbC-N.Rec-1), TCRa/bC-N.Rec-2 (including TCRaC-N.Rec-2 and TCRbC-N.Rec-2), TCRa/bC-N.Rec-3 (including TCRaC-N.Rec-3 and TCRbC-N.Rec-3), TCRa/bC-N.Rec-4 (including TCRaC-N.Rec-4 and TCRbC-N.Rec-4), TCRa/bC-N.rRec (including TCRaC-N.rRec and TCRbC-N.rRec), TCRa/bC-Cys (including TCRaC-Cys and TCRbC-Cys), TCRa/bC-TM9 (including TCRaC-TM9 and TCRbC-WT), TCRa/bC-Cys-N.Rec-1 (including TCRaC-Cys-N.Rec-1 and TCRbC-Cys-N.Rec-1), TCRa/bC-TM9-N.Rec-1 (including TCRaC-TM9-N.Rec-1 and TCRbC-N.Rec-1), TCRa/bC-Cys-TM9 (including TCRaC-Cys-TM9 and TCRbC-Cys), TCRa/bC-Cys-TM9-N.Rec-1 (including TCRaC-Cys-TM9-N. Rec-1 and TCRbC-Cys-N.Rec-1); and for different targets, the TCR constant regions are all pHAGE-EFIA-334-VL-TCRbC-P2A-VH-TCRaC-IRES-RFP, pHAGE-EFIA-2C6-VL-(G4S) 3-VH-TCRbC-P2A-FMC63-VL-(G4S) 3-VH-TCRaC-IRES-RFP, pHAGE-EF1A-M971-VL-(G4S) 3-VH-TCRbC-P2A-334-VL-(G4S) 3-VH-TCRaC-IRES-RFP and other plasmids.

Example 4. Construction of Tool Plasmids and Cell Lines

1) Construction of the Plasmid pHAGE-Luciferase-GFP

The pHAGE as a lentiviral vector can stably insert target genes into a target cell genome, and is an important way for constructing stable cell lines. Luciferase is an enzyme with catalytic activity and can catalyze a substrate to generate chemical self-luminescence, the number of the target cells can be indicated after the target cells stably express the luciferase and the substrate is added, and therefore the influence of functional cells on the target cells is reflected. A PHAGE-EF1A vector carries restriction enzyme Not I/Cla I restriction enzyme cutting sites, the vector was cut by using the two enzymes, the luciferase and GFP sequences were obtained from NCBI, fragments were synthesized by Ruibiotech which is a commercial company, luciferase genes and GFP genes were combined by using an Overlap PCR method, then a luciferase-GFP fragment was connected into the pHAGE vector by using a homologous recombination method, forward and reverse primers were respectively designed at EF1A and WPRE, and sequencing was carried out to determine whether the vector construction is successful or not.

2) Construction of Luciferase-Bearing Target Cell Lines (Cell Line Table)

After successful construction of the lentiviral vector with the luciferase and the GFP, the lentivirus was packaged by Lentix-293T, a lentivirus solution was concentrated by a PEG8000 concentration method, the viral titer was determined by using a gradient dilution method, and then the target cells were infected, which include, but are not limited to the cell lines in the following table:

| Name | Target | Corresponding cancers/diseases or functions |
|---|---|---|
| A431 | EGFR | Skin cancer |
| A549 | EGFR | Lung cancer |
| B16/htEGFR | EGFR | Melanoma |
| HepG2 | GPC3 | Liver cancer |
| HUH7 | GPC3 | Liver cancer |
| RAJI | CD19 | Lymphoma/leukemia |
| RAJI-CD19KO | CD19- | Lymphoma/leukemia |
| RAJI-CD20KO | CD20- | Lymphoma |
| RAJI-CD22KO | CD22- | Lymphoma |

Whether GFP positive cells exist or not was observed through a fluorescence microscope 72 hours after infection, then the GFP positive cells were sorted out through a flow sorter, monoclones were selected, and a library was built and stored. Meanwhile, co-incubating of the luciferase substrate and the target cells was carried out, the expression and expression level of the luciferase was detected.

3) Construction of TCRa/b-Knockout Jurkat Cell Lines

Based on the structure and sequence characteristics of TCR, guide sequences were designed in constant regions of an α chain and a β chain, and a TCR α-β-Jurkat cell line was constructed. The constant region exon sequences of the α chain and the β chain of the TCR were respectively obtained at NCBI, the exon 1 sequences of the constant regions of the α chain and the β chain were submitted to the tools.genome-engineering.org website to design a guide sequence, and an oligo sequence was synthesized according to the result. A sgRNA-LentiCRISPR lentiviral vector was then constructed, the CRISPR lentiviral vector was digested with a BsmBI restriction enzyme, a filter sequence was removed, the ligated ends were exposed, and the plasmids were treated with an alkaline phosphatase for 1 hour at 37° C. to reduce self-ligation. The system subjected to enzyme digestion was subjected to agarose gel electrophoresis for gel recovery, a plasmid skeleton of the target fragment was about 11500 bp, and meanwhile, a cut filter band existed at the position of −2000 bp; an oligo single chain of the synthesized guide sequence was treated by using a T4 ligase and T4 PNK in vitro, annealed into double chains and added with a phosphate group at the end for ligation; the annealed double-chain guide sequence was diluted with water by 200 times to be connected with LentiCRISPR subjected to BsmBI enzyme digestion so as to be transformed into Stb13 *Escherichia coli*, and the plasmids were extracted for virus coating infection. The guide sequence of the α chain was linked to LentiCRISPR-puro, and the guide sequence of the β chain was linked to LentiCRISPR-BSD. Packaging and concentrating of the sgRNA-LentiCRISPR lentivirus comprises the steps of spreading HEK-293T to a 10 cm dish in advance, preparing a transfection system when cells grow to 80%-90%, adding the transfection system into HEK-293T, putting the cells back to a 37° C. incubator for culturing, and recording the time as 0 hour; after 12 hours after transfection, changing with fresh 10% FBS-DMEM; collecting viruses after 48 hours and 72 hours of transfection; centrifuging and filtering a virus-containing culture medium, adding PEG8000 to be uniformly mixed, standing at 4 DEG C for more than 12 hours, and centrifuging at 3500 rpm for 30 minutes; discarding a supernatant, and conducting resuspended precipitation with a suitable volume of culture medium; and conducting-80 cryopreservation, or conducting direct use. Jurkat T cell infection, drug killing screening and monoclonal cell line identification comprised the steps that Jurkat T cells were inoculated in a 12-well or 24-well plate; the cell density was not allowed to be too large; sgRNA-LentiCRISPR viruses of the α chain and the β chain with appropriate volumes were simultaneously added, and polybrene (added according to the total volume of 1:1000) was added to be uniformly mixed; centrifuged infection was carried out at 1000 rpm, and 32° C. centrifugation was carried out for 90 min, the cells were taken out to be put into a 37° C. incubator, and time was recorded as 0 hour; the solution was changed after 10-12 hours; after 48 hours, Puromycin and Blasticidin were added to an appropriate final concentration, and after 48 hours of drug killing, all cells of an uninfected control group were dead. The surviving cells were sucked out, and culturing with a complete culture medium was carried out after centrifuging to obtain a TCR α-β-Jurkat cell library; single cells of the TCR α-β-Jurkat cell library were sorted into a 96-well plate by using flow type Aria, culturing was carried out for two weeks, grown single cells were sucked out, and enlarged culture was carried out; the monoclonal cell line was respectively identified by using antibodies of the TCR α chain and the TCR β chain, and the cell line of which the two chains are defective were amplified to obtain the Jurkat T cell line of which the endogenous TCR was knocked out.

Example 5. Establishment of a Viral System to Transduce T Cells

1) Lentiviral System and Packaging Method (Different Generations)

The Lentix-293T cells were inoculated into a 10 cm culture dish according to $5*10^5$/mL, cultured in a 5% CO2 incubator at 37° C., and transfected when the cell density reached about 80% (observed under a microscope). Three plasmids were mixed well with 500 μL of serum-free DMEM at a ratio of PMD2. G:PSPAX:transfer plasmid=1: 2:3.54 μL of PEI-max was mixed well with 500 μL of serum-free DMEM and allowed to stand for 5 min at room temperature (the volume-to-mass ratio of PEI-Max to the plasmids was 3:1). A PEI-max mixed solution was slowly added into a plasmid mixed solution to be slightly blown and beaten so as to be uniformly mixed, and standing at room temperature was carried out for 15 minutes. A final mixed solution was slowly added into a culture medium to be sufficiently and uniformly mixed, then the mixed solution was put back into the incubator to be continuously cultured for 12-16 hours and transferred into a 6% FBS DMEM culture medium to be continuously cultured, and 48-hour and 72-hour virus solutions were collected.

2) Viral Titer Measurement Method

The Jurkat-C5 cells were inoculated in a flat-bottom 96-well plate according $5*10^5$/mL, and 100 μL of 1640 culture medium containing 10% FBS and 0.2 μL of 1000*polybrene was added to each well. When the viruses were diluted, 10-fold dilution was carried out by using a 1640 complete culture medium, if the viruses are a virus stock solution, the virus quantity of the first well was 100 μL, and if the virus are a concentrated solution, the virus quantity of the first well was 1 μL; the diluted cells were added to virus wells at 100 μL/well to be mixed, centrifugation was carried out at 32° C. and 1500 rpm for 90 min, and cultivation was carried out at 37° C. in a 5% C02 incubator for 72 h. Cells on a 96-well flat bottom plate were sucked onto a round-bottom 96-well plate and centrifuged at 4° C. and 1800 rpm for 5 min, and a supernatant was discarded. After addition of 200 μL of 1*PBS, centrifugation was carried out at 1800 rpm for 5 min at 4° C., and a supernatant was discarded. 200 μL of 4% tissue fixing liquid was added, preservation in a dark place was carried out, and loading on a flow cytometer was carried out. The infection efficiency was measured by using the flow cytometer, wells with an infection rate of 2%-30% were selected when the titer was calculated, and the calculation formula was that the titer (TU/mL)=$1.5*10^4$*positive rate/virus volume (uL) *1000.

The viruses pHAGE-EF1A-IRES-RFP of the following plasmids were packaged by the above method; the constant regions were various pHAGE-EFIA-Cetux-VL-TCRaC-P2A-VH-TCRbC-IRES-RFP and pHAGE-EFIA-GC33-VL-TCRaC-P2A-VH-TCRbC-IRES-RFP plasmids of TCRa/bC-WT (comprising TCRaC-WT and TCRbC-WT), TCRa/bC-N.DLT (comprising TCRaC-N.DLT and TCRbC-N.DLT), TCRa/bC-C.DLT (comprising TCRaC-C.DLT and TCRbC-CDLT), TCRa/bC-N.Rec-1 (comprising TCRaC-N.Rec-1 and TCRbC-N.Rec-1), TCRa/bC-N.Rec-2 (comprising TCRaC-N.Rec-2 and TCRbC-N.Rec-2), TCRa/bC-N.Rec-3 (comprising TCRaC-N.Rec-3 and TCRbC-N.Rec-3), TCRa/bC-N.Rec-4 (comprising TCRaC-N.Rec-4 and TCRbC-N.Rec-4), TCRa/bC-N.rRec (comprising TCRaC-N.rRec and TCRbC-N.rRec), TCRa/bC-Cys (comprising TCRaC-Cys and TCRbC-Cys), TCRa/bC-TM9 (comprising TCRaC-TM9 and TCRbC-WT), TCRa/bC-Cys-N.Rec-1 (comprising TCRaC-Cys-N.Rec-1 and TCRbC-Cys-N.Rec-1), TCRa/bC-TM9-N.Rec-1 (comprising TCRaC-TM9-N.Rec-1 and TCRbC-N.Rec-1), TCRa/bC-Cys-TM9 (comprising TCRaC-Cys-TM9 and TCRbC-Cys) and TCRa/bC-Cys-TM9-N.Rec-1 (comprising TCRaC-Cys-TM9-N.Rec-1 and TCRbC-Cys-N.Rec-1); and for different targets, the TCR constant regions were all pHAGE-EF1A-334-VL-TCRbC-P2A-VH-TCRaC-IRES-RFP, pHAGE-EF1A-2C6-VL-(G4S) 3-VH-TCRbC-P2A-FMC63-VL-(G4S) 3-VH-TCRaC-IRES-RFP and pHAGE-EF1A-M971-VL-(G4S) 3-VH-TCRbC-P2A-334-VL-(G4S) 3-VH-TCRaC-IRES-RFPpHAGE-EF1A-334-VL-TCRbC-P2A of TCRa/bC-Cys-TM9-N.Rec-1 and other plasmids.

Example 6. Establishment of T Cell Culture and Infection Methods

1) Culture Method of Jurkat T Cell Lines

The Jurkat T cell lines were cultured with a RPMI 1640 medium containing 10% FBS. The culture density was $3*10^5$/ml and does not exceed $3*10^6$/ml at most, passage was carried out every 1-2 days, the cells were counted, the required amount of cells was taken, the culture medium was supplemented to adjust the density, and the cells were put in a CO2 culture box for culture.

2) Infection Method of Jurkat T Cell Lines

The method comprises the following steps of counting the cells, taking $1*10^6$/ml of cells for centrifuging and liquid changing, resuspending by using 1 ml of RPMI 1640 culture medium containing 10% FBS, adding into a 24-well plate, adding a proper amount of virus liquid, centrifuging at 1500 rpm for 90 minutes, and culturing in a CO2 incubator. After 12 hours of infection, the liquid was thoroughly changed with a fresh RPMI 1640 culture medium containing 10% FBS, and the positive rate was detected after 72 hours.

3) Culture Method of Human Primary T Cells

Primary T cells were obtained by a Ficoll separation method and cultured in an X-VIVO medium with 10% FBS and 100 IU/ml IL-2, and adding into CD3 and RetroNectin r-Fibronectin (final concentration of 5 μg/ml) pre-coated plates at an initial culture density of $1*10^6$/ml. The later culture density was $5*10^5$/ml and does not exceed $3*10^6$/ml at most, and passage was carried out every 1-2 days.

4) Infection Method of Human Primary T Cells

After the primary T cells were cultured for 48 hours, the virus liquid was added, MOI was equal to 20, centrifugation was conducted at 1500 rpm for 90 min, and the cells were placed in a CO2 incubator to be cultured. After 24 hours of infection, an X-VIVO culture medium containing 10% FBS and 100 IU/ml IL-2 was supplemented, well transferring was performed, and the infection efficiency was detected through tag proteins or antibodies after 72 hours.

5) Infection Efficiency Detection Method

Cells were blown evenly and counted 72 h after infection, $5*10^5$/ml was taken for centrifugation, the supernatant was discarded, a staining solution was PBS+2% FBS+2 mM EDTA, a corresponding antibody was added for incubation, incubation was conducted for 30 min, then PBS was added for washing twice, and loading was carried out for detection.

Example 7. Expression Detection Method of an STAR and a Mutant Thereof in T Cells In the T cell transformation process by means of gene transformation, the expression, membrane loading and distribution of target genes on the cell surface influence the functions of the T cells, so that the virus infection efficiency was detected through fluorescent proteins, and the membrane loading efficiency of the STAR was detected through a flow antibody by connecting a myc antibody to the N-terminal of the STAR. Because the structure of the STAR originates from the TCR, whether the STAR was mispaired with the endogenous TCR affects the expression abundance of the intact STAR, and the mispairing efficiency was evaluated by comparing the RFP positive ratio with the STAR myc positive ratio.

1) STAR Membrane Loading Efficiency Detection

The constructed pHAGE-EF1A-myc-STAR-IRES-RFP plasmids were subjected to virus packaging by Lentix-293T, virus concentration and titer detection were carried out, then Jurkat C5 and primary T cells were infected, after 72 h of infection, infected cells were collected, staining was carried out with FITC-anti-myc antibodies and APC-anti-mTCR-β antibodies, and a flow RFP/FITC/APC fluorescence channel was detected by using a flow cytometer (BD Fortessa). If the FITC or APC has an obvious positive cell population, it was indicated that STAR membrane loading expression can be carried out, and if both the FITC and APC were not expressed, the STAR does not realize membrane loading.

2) Assessment of Probability of Mispairing of the STAR with the Endogenous TCR

The constructed pHAGE-EFIA-myc-STAR-IRES-RFP plasmids were subjected to virus packaging by Lentix-293T, virus concentration and titer detection were carried out, then Jurkat and primary T cells were infected, infected cells were collected 72 h after infection, staining was carried out by using the FITC-anti-myc antibodies and the APC-anti-mTCR-antibodies, and the flow RFP/FITC/APC fluorescence channel was detected by using the flow cytometer (BD Fortessa f4). The difference between the RFP positive rate and the FITC or APC positive rate was detected.

Example 8. Functional Detection Method of the In-Vitro Level of an STAR and a Mutant thereof in T Cells 1) In Vitro Co-Culture Method of T Cells with Target Cells The T cells comprise T cell line Jurkat C5, Jurkat and a primary cell line are suspension cells, the target cells can be divided into suspension cells and adherent cells according to different antigens and cell lines, the suspension target cells such as RAJI and the like were co-incubated with the T cells, if the suspension target cells such as RAJI and the T cells were co-cultured, the corresponding number of cells were taken at the same time, and the cells were uniformly mixed with a target cell culture medium for centrifugal culture; and if the cells are adherent target cells, the target cells need to be inoculated one day in advance, and then a certain number of T cells were added, wherein the method comprises the following specific steps of infecting a T cell line or a primary T cell by using packaged and purified STAR viruses, conducting flow-type detection on the infection efficiency one day before co-culturing, determining the ratio of functional cells to the target cells, generally using the ratio of 10:1, 5:1 and 1:1, and calculating the total number of T cells according to the infection efficiency, wherein the using amount of the target cells was generally 4E5/well (24-well plate).

2) Method for Stimulation of T Cells by Target Antigens

The target of the application is generally a cell surface protein, and the antigen can be directly used for activation of T cells to detect the function of the T cells, typically 300 microliters of 5 μg/ml antigen (1*coating buffer dilution, taking a 24-well plate as an example) was used for coating the well plate overnight, then the antigen was discarded, 1E6/well of positive T cells were added, and the T cells were collected after 6, 12 and 24 hours of centrifugal activation for detecting the function of the T cells.

3) Analysis of Secreted Cytokines of T Cells: ELISA

The T cell could release a large number of cytokines (common examples include TNF-α, IFN-γ and IL-2) in the activation process to help the T cell kill the target cell or promote proliferation of the T cell self. After being simulated by the target cell or the antigen, the T cell was collected and centrifuged, and a supernatant was taken. TNF-α, IFN-γ and IL-2 ELISA kits employed Human IL-2 Uncoated ELISA, Human TNF-α Uncoated ELISA and Human IFN-γ Uncoated ELISA (with Art. No. 88-7025, 88-7346, 88-7316) respectively. The specific steps are as follows: 10× Coating Buffer was diluted by $ddH_2O$ to 1×, a coating antibody (250×) was added for uniform mixing, and then a mixture was added to a 96-well plate (special for ELISA) with 100 μl per well. After being sealed with a preservative film for still standing overnight at 4° C., the 96-well plate was washed with 1×PBST (also called Wash Buffer, 0.05% Tween 20 was added in 1×PBS) for 3 times with 260 μl per well each time; 5× ELISA/ELISPOT Diluent was diluted by $ddH_2O$ to 1×; a product was added to the 96-well plate with 200 μl per well; and the 96-well plate was left for still standing for 1 h at a room temperature. The 96-well plate was washed with the PBST for 1 time and diluted to obtain standard curves (ranges of which were 2-250, 4-500 and 4-500 respectively); and a sample was diluted with 1× Diluent by 20-50 times. The sample and the standard curves were added with 100 μl per well and two multiple pores; after incubation at a normal temperature for 2 h, the 96-well plate was washed by the PBST for 3 times; Detection antibody which had been diluted by 1× Diluent was added for incubation for 1 h, and then the 96-well plate was washed by the PBST for 3 times; then HRP which had been diluted by 1× Diluent was added for incubation for 30 min, and then the 96-well plate was washed for 6 time; TMB was added for developing with a developing time not exceeding 15 min; 2N $H_2SO_4$ was added for ending developing; and light absorption was detected by conducting light absorption at 450 nm.

4) Verification on Killing Function of T Cell: Luciferase Detection

After co-culture for 24 h, a cell suspension was slightly blown uniformly, 150 μL of cell suspension was taken from each well and added to a white 96-well plate; 2 multiple pores were selected from each well; and a luciferase substrate (Promega) was added. Oscillation (at a low speed) was conducted for co-incubation for 10 min; and then a multimode reader was used for detecting a chemiluminescence value with a gain fixed at 100. Cell killing calculation: killing efficiency=100%-(effector cell-targeting cell well value/control cell-targeting cell well value).

Example 9. Method of Detecting Functions of STAR Receptor and Mutant Thereof in T Cell at Level of Animal Tumor Model 1) Experimental Animal Model This experiment employed NSG immunodeficient mice as a model. The mice have a genotype of NOD-Prkdc$^{em26}$Il2rg$^{em26}$/Nju and are deficient in T cells, B cells and NK cells; and macrophages and dendritic cells of the mice also have defects. NSG mice belongs to a mouse strain with most complete immunodeficiencies and are widely applied to preclinical research on T-cell therapy without having rejection reaction to transplantation tumors and the T cells. In this experiment, 6-8-week-old female NSG mice were used; a weight difference between the mice in the experiment in each batch was controlled within 2 g. The mice were fed in individually ventilated cages in a specific pathogen free (SPF) clean-grade barrier and fed with normal diets and drinking water with slightly acid pH, so as to prevent pathogen pollution.

2) Establishment of Tumor Model

The present invention employed various tumor models to verify functions of STAR-T cells, so that the universality of the effects of the STAR-T cells were verified. In construction of a hematological tumor model, this experiment used Raji cells in human Burkitt's lymphoma cell line for xenotransplantation. The Raji cells are cell strains for expressing a luciferase gene through a lentiviral vector and monitor development and changes of Raji tumors in real time in the mice in modes of chemiluminescence of luciferin and living imaging. In the model, different doses (about 1-3×10$^6$ cells in general) of Raji-luciferase cells were inoculated to the 6-8-week-old female NSG mice through tail vein reinfusion. After 3 days, the mice were injected intraperitoneally with a luciferin potassium salt solution, and fluorescence signals in tumor cells in bodies were detected in the living imaging mode. The Raji cells rapidly grew in the mice and were distributed throughout the bodies through blood, so as to have a certain probability of infecting organs, form solid tumors and causes symptoms of reducing weights and the like of the mice; in the case without therapeutic treatment, Raji tumor burdens would cause death of the mice after about 30-40 d.

In construction of a solid tumor xenotransplantation model, this experiment selected various tumor types, including a human epidermoid carcinoma A431 cell line, a human non-small cell lung cancer A549 cell line, a human liver cancer Huh-7 and HepG2, human glioma U87 and U251 cell lines and a human breast cancer MDA-MB-231 cell line. These cells express the luciferase gene through a lentiviral vector and monitor development and changes of tumors in real time in the mice in the modes of chemiluminescence of luciferin and living imaging. In the model, after different doses (in a range from 2×10$^5$ to 3×10$^6$ according to the malignant degrees and different characteristics of the tumors) of the cells were mixed with matrigel, a mixture was inoculated to the mice subcutaneously through subcutaneous injection. After 3 days, the mice were injected intraperitoneally with the luciferin potassium salt solution, and the fluorescence signals in the tumor cells in the bodies might be detected in the living imaging mode. The solid tumors subjected to subcutaneous inoculation generally do not have the invasiveness, are difficult to transfer and usually form dense tumor masses in situ subcutaneously. A length, a width and a height of each tumor mass were measured with a vernier caliper, and tumor progression might further be monitored through the size of each tumor. In the case without therapeutic treatment, the tumor masses formed by these solid tumor cells reached specifications of standards of animal welfare ethics after about 20-40 d, that is, when maximum sizes of each tumor masses exceeded 15 mm, sizes of each tumor masses exceeded 1500 mm$^3$, fester was formed in subcutaneous tumor regions, or tumors significantly affected activities and eating of the mice, the animals should be euthanized.

3) Operation Method for Animal Experiment

An operation method for the mice as experimental animals comprises: catching, fixing, numbering, anaesthetization, unhairing, administration, blood taking, execution and dissection, wherein in this experiment, a used numbering method comprises: toe-clipping, earmarking and coat color marking method. In this experiment, the used anaesthetization method comprises: inhalation anaesthetization of isoflurane and injection anaesthetization of Avertin or pentobarbital.

The unhairing method comprises: local sites of the mice were unhaired with scissors or a razor. The administration method comprises: intraperitoneal injection, tail vein injection, subcutaneous injection, postorbital venous plexus injection, intracranial injection and the like. The blood taking method comprises: orbital blood collection, blood drawing with eyeball extraction, tail vein blood collection and the like. The execution method comprises: execution with pulling off necks, execution with carbon dioxide and the like. All operations were conducted after approval of an experimental animal research and using plan (Animal protocol).

4) Monitoring Means for Tumor Growth

This experiment mainly detects tumor growth through two means. The first is in vivo fluorescence imaging method: tumor cells having luciferase genes were injected into animals for colonization. The mice were injected intraperitoneally with the luciferin potassium salt solution, the substrate emitted light with a specific wavelength under the effect of an enzyme, and fluorescence signals in the tumor cells in the bodies were detected with CCD equipment sensitive to a living imaging instrument. Further, a professional software may be used for quantitatively analyzing the fluorescence signals and drawing thermal images, so that tumor growth may be intuitively and quantitatively reflected. A second method is to measure the sizes of subcutaneous tumors: the length, the width and the height of each tumor were measured with the vernier caliper, and each volume value was solved through a specific computational formula. Common computational formulas comprises: volume=length×width×height; volume=3×length×width×height and the like.

5) Detection Method for Viability and Proliferation of T Cells in Animals

The viability and proliferation conditions of the T cells in the bodies are directly linked to the final anti-tumor effect of the T cells. To detect the viability and proliferation conditions of the T cells in the animals, in this experiment, blood was regularly drawn from the mice, and a ratio, a cell state and cell classification of the STAR-T cells in peripheral blood were analyzed. A specific operation is as follows: about every one week, the mice were anesthetized with the isoflurane and subjected to orbital blood collection with the amount of about 100 μl. After a blood sample was subjected to operations of anticoagulation, plasma collection, red blood cell lysis and the like, the rest cells were subjected to flow staining, so as to detect a ratio of CD4 to CD8 and molecules of CCR7, CD45RA, PD-1, LAG-3, TIM-3 and the like for analysis on a T cell subset and analysis on the cell state. Meanwhile, through a method of counting with a flow cytometer and digital PCR, an absolute quantity value of the STAR-T cells in the peripheral blood of each mouse was obtained. In addition, at the end of the experiment, the mice might be dissected, and ratios of the T cells in other immune organs of the mice were detected.

6) Evaluation Method for Safety of T Cells in Animals

To evaluate the cytotoxicity and the safety of the STAR-T cells, whether the cells had caused side effect on experimental animals or not might be detected. By observing behavior states of the mice, conducting pathological analysis on the mice, slicing important organs of the mice for analysis and other modes, whether reinfused T cells had significant cytotoxicity or not might be evaluated. Meanwhile, through T cellular infiltration analysis on non-tumor tissues of the mice, whether the T cells had the off-target killing effect on the non-tumor tissues or not might further be judged. In addition, by detecting a level of cytokines (such as IL-2, IFN-γ, TNFα or IL-6) in blood of each mouse, whether the T cells would cause a systematic cytokine storm or not might be judged.

7) Evaluation Method for Tumor Infiltration Ability of T Cells

The ability of the T cells infiltrating the tumors is a core ability for challenging the solid tumors. To detect the infiltration ability of the T cells, tumor tissues might be separated, digested and ground firstly to obtain single cells, and a proportion of the T cells in the tumor tissues might be detected through flow staining. Meanwhile, tumor cells, tumor stroma cells and immune cells might be further separated from a tumor suspension through a method of density gradient centrifugation (such as Percoll gradient and Ficoll gradient), so that purified tumor infiltrating T cells were obtained; and the characteristics (including chemokine receptor expression and a T cell exhaustion degree) of the purified tumor infiltrating T cells were analyzed in detail by using methods of sequencing and the like.

Example 10. Construction of Anti-EGFR STAR Receptor and Identification on Modification of Constant Region 10.1. Construction of Anti-EGFR STAR Receptor (1) Determination on Sequence of Antibody Targeting EGFR An antibody heavy chain variable region (anti-EGFR Cetux-VH, SEQ ID NO: 22) and an antibody light chain variable region (anti-EGFR Cetux-VL, SEQ ID NO: 23) selected Centuximab (Cetux for short). A sequence was synthesized by optimizing a codon.

(2) Design of STAR Targeting EGFR

The STAR contained two polypeptide chains; the anti-EGFR Cetux-VL was fused to a mouse TCRbC-WT chain to form a first polypeptide segment; and the anti-EGFR Cetux-VH was fused to a mouse TCRaC-WT chain to form a second polypeptide segment. The two chains both used GM-CSF signal peptides. Gene sequences of the STAR were linked through polypeptide segments at a Furin-SGSG-p2A protease cleavage site; two polypeptide chains would be transcribed, translated and expressed as a protein together; and then, the protein was cleaved by proteases corresponding to furin and p2A to form two independent protein chains. The two protein chains and endogenous CD3 subunits (ε, δ, γ, ζ) of the T cells formed a complex; and under the guidance of a GM-CSF signal peptide, the complex was transferred and presented onto a cell membrane (as shown in FIG. 1).

(3) Cloning and Assembly of Gene Fragment

Through modes of gene synthesis and cloning, four fragments "anti-EGFR Cetux-VL", "mouse TCRbC-WT", "anti-EGFR Cetux-VH" and "mouse TCRaC-WT" were obtained. Each pair of primers had 25 bp bases homologous to front and next bases; the four fragments were further recombined through a Gibson Assembly method and then linked to a lentiviral vector pHAGE; and therefore, STAR was obtained.

(4) Vector Transformation and Sequencing

A product of Gibson Assembly was transformed to a DH5a strain and grew on an LB plate containing ampicillin overnight. Monoclonal bacteria were selected for sequencing, and sequencing primers selected primers seq-pHAGE-F and seq-pHAGE-R on a pHAGE vector.

(5) Plasmid Extraction

The bacteria sequenced to be correct were inoculated to an LB liquid medium for culture overnight. A kit with an endotoxin removing function was used for extracting plasmids. A concentration of the plasmids was measured with Nanodrop, a final concentration of the plasmids was about 1000 ng/ul, and a A260/A280 value was larger than 1.8. Thus, STAR plasmids pHAGE-EF1A-Cetux-VL-TCRaC-P2A-VH-TCRbC-IRES-RFP having a constant region of mouse TCRa/bC-WT and targeting the EGFR were obtained.

Similarly, various plasmids pHAGE-EFIA-Cetux-VL-TCRaC-P2A-VH-TCRbC-IRES-RFP having constant regions which are TCRa/bC-N.DLT (containing TCRaC-N.DLT and TCRbC-N.DLT), TCRa/bC-C.DLT (containing TCRaC-C.DLT and TCRbC-CDLT), TCRa/bC-N.Rec-1 (containing TCRaC-N.Rec-1 and TCRbC-N.Rec-1), TCRa/bC-N.Rec-2 (containing TCRaC-N.Rec-2 and TCRbC-N.Rec-2), TCRa/bC-N.Rec-3 (containing TCRaC-N.Rec-3 and TCRbC-N.Rec-3), TCRa/bC-N.Rec-4 (containing TCRaC-N.Rec-4 and TCRbC-N.Rec-4), TCRa/bC-N.rRec (containing TCRaC-N.rRec and TCRbC-N.rRec), TCRa/bC-Cys (containing TCRaC-Cys and TCRbC-Cys), TCRa/bC-TM9 (containing TCRaC-TM9 and TCRbC-WT), TCRa/bC-Cys-N.Rec-1 (containing TCRaC-Cys-N.Rec-1 and TCRbC-Cys-N.Rec-1), TCRa/bC-TM9-N.Rec-1 (containing TCRaC-TM9-N.Rec-1 and TCRbC-N.Rec-1), TCRa/bC-Cys-TM9 (containing TCRaC-Cys-TM9 and TCRbC-Cys), TCRa/bC-Cys-TM9-N.Rec-1 (containing TCRaC-Cys-TM9-N.Rec-1 and TCRbC-Cys-N.Rec-1) were constructed.

Figure 6A:
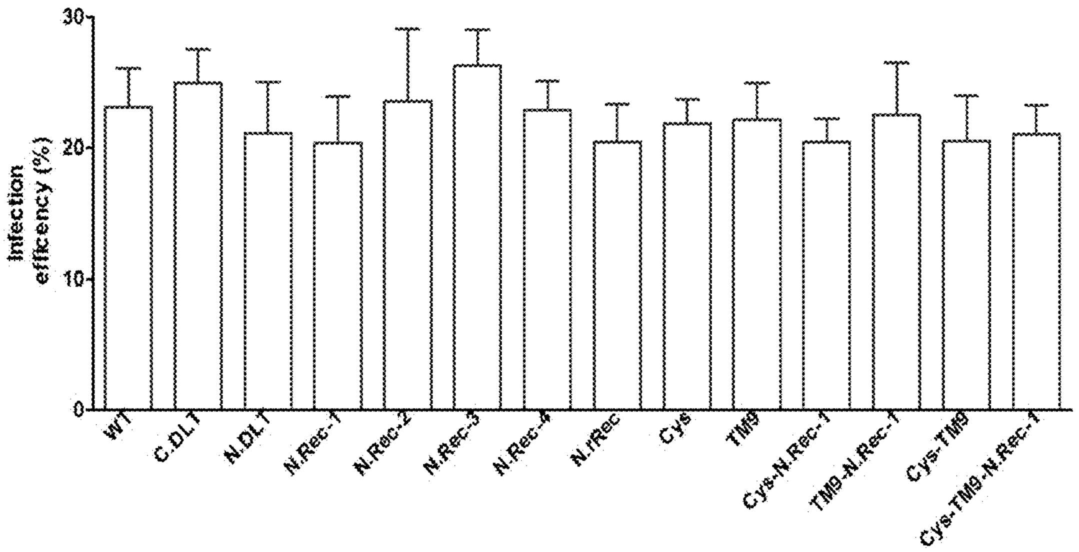
FIG. 6 shows function of various mutant of Cetux STAR targeting EGFR.
Figure 6B:
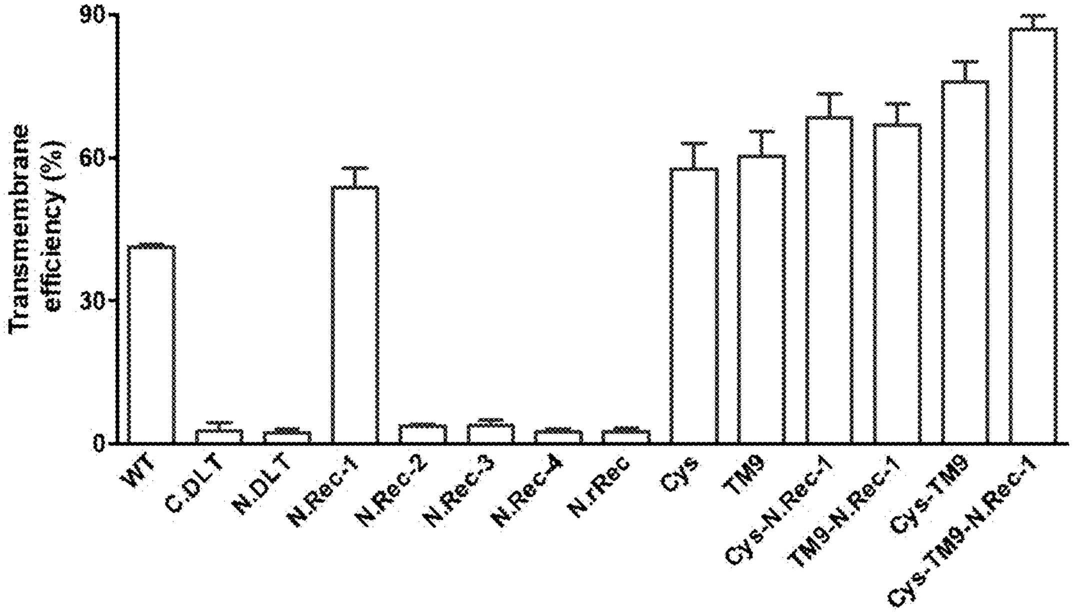
Figure 6C:
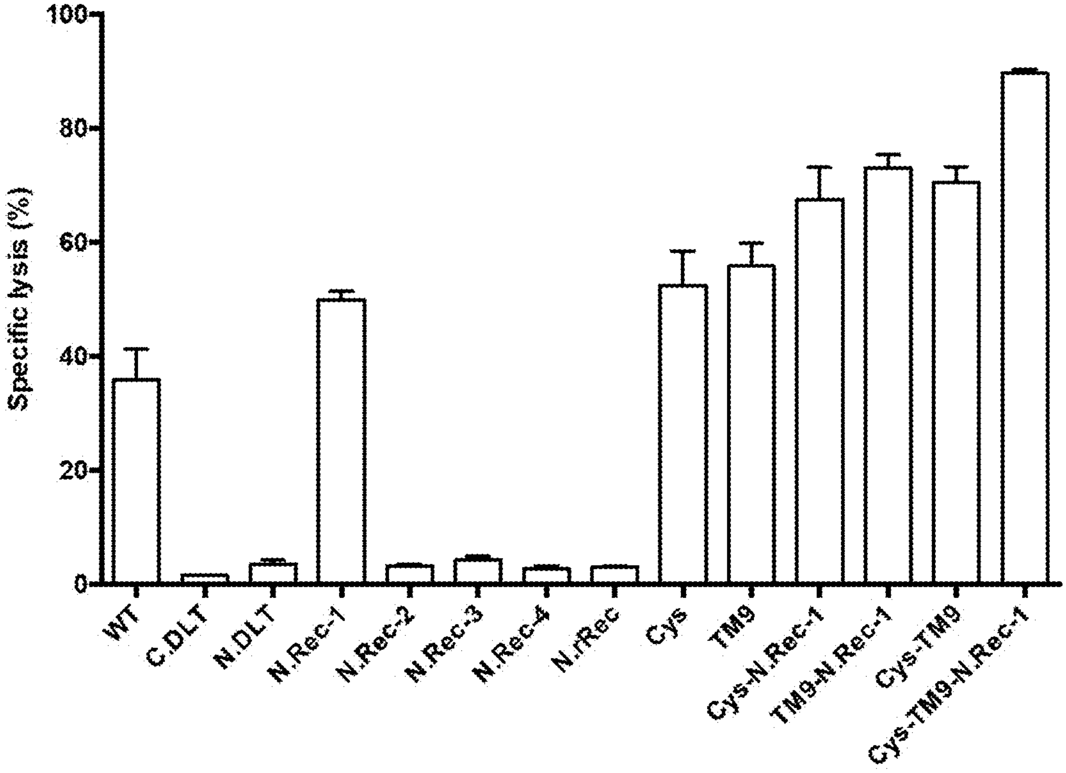
Figure 7A:
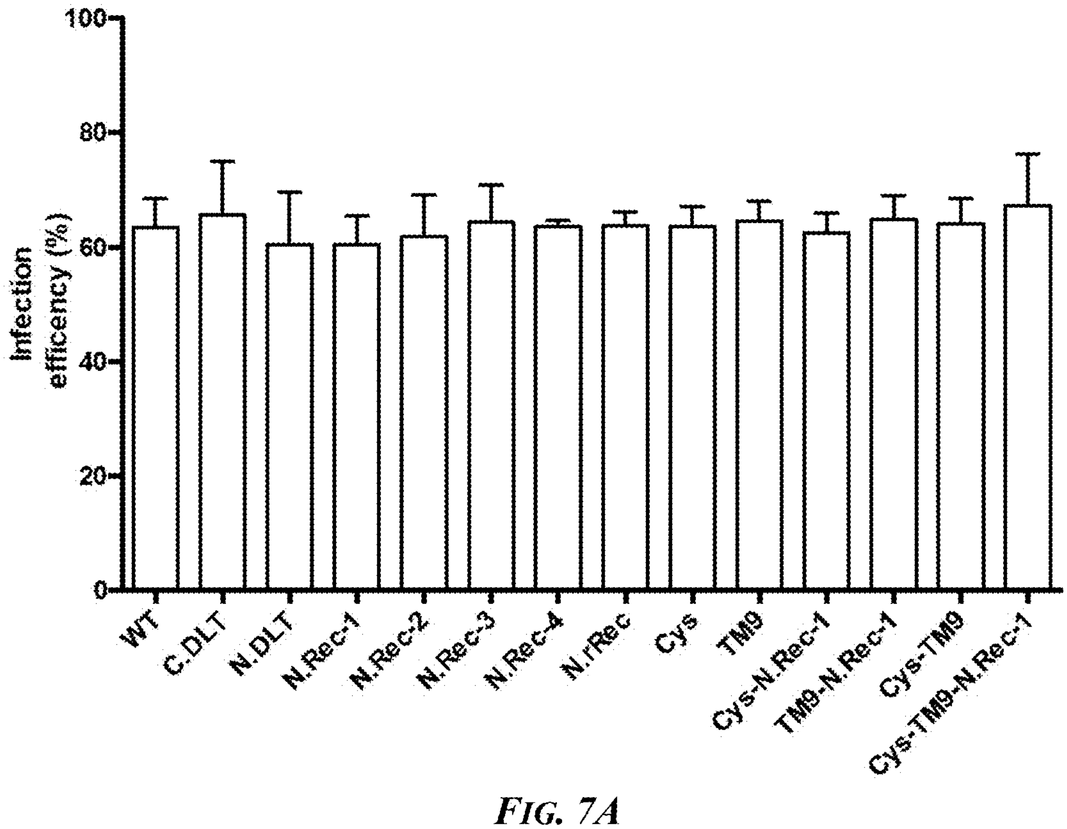
FIG. 7 shows function of various mutant of GC33 STAR targeting GPC3.
Figure 7B:
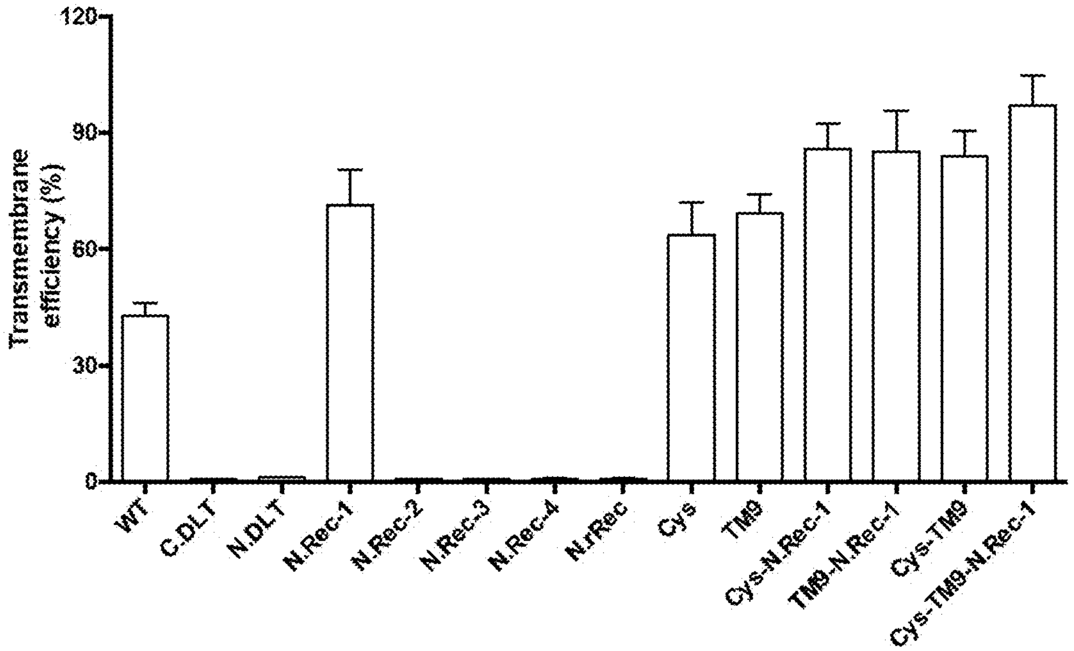
Figure 7C:
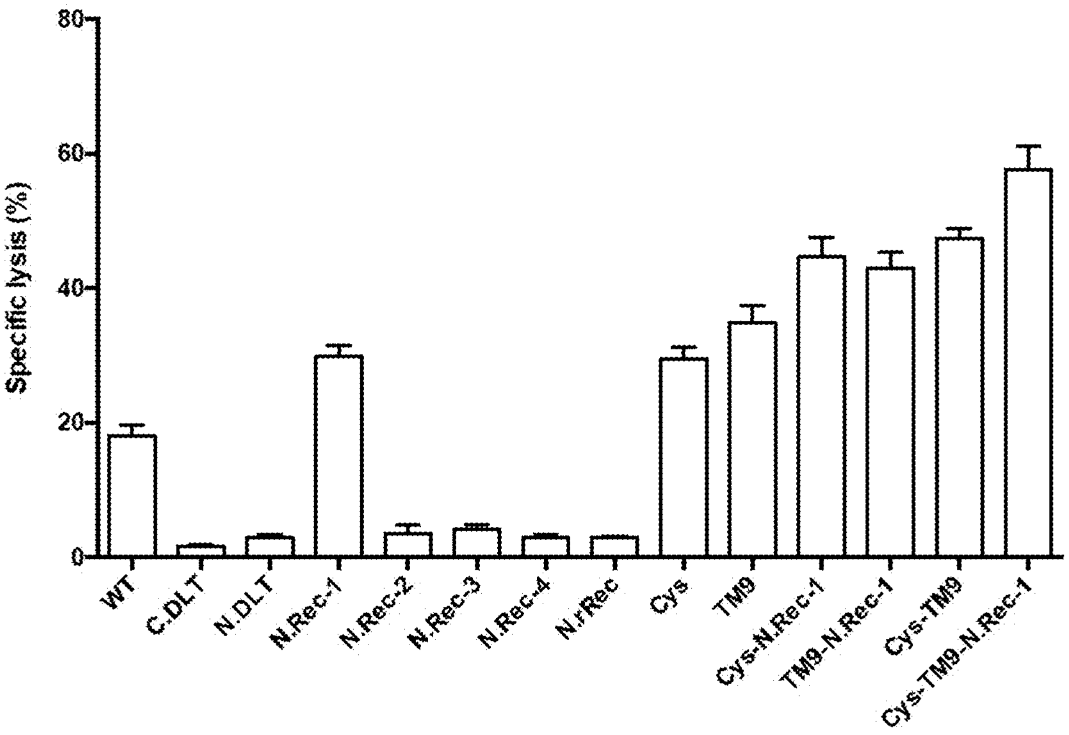
Figure 7D:
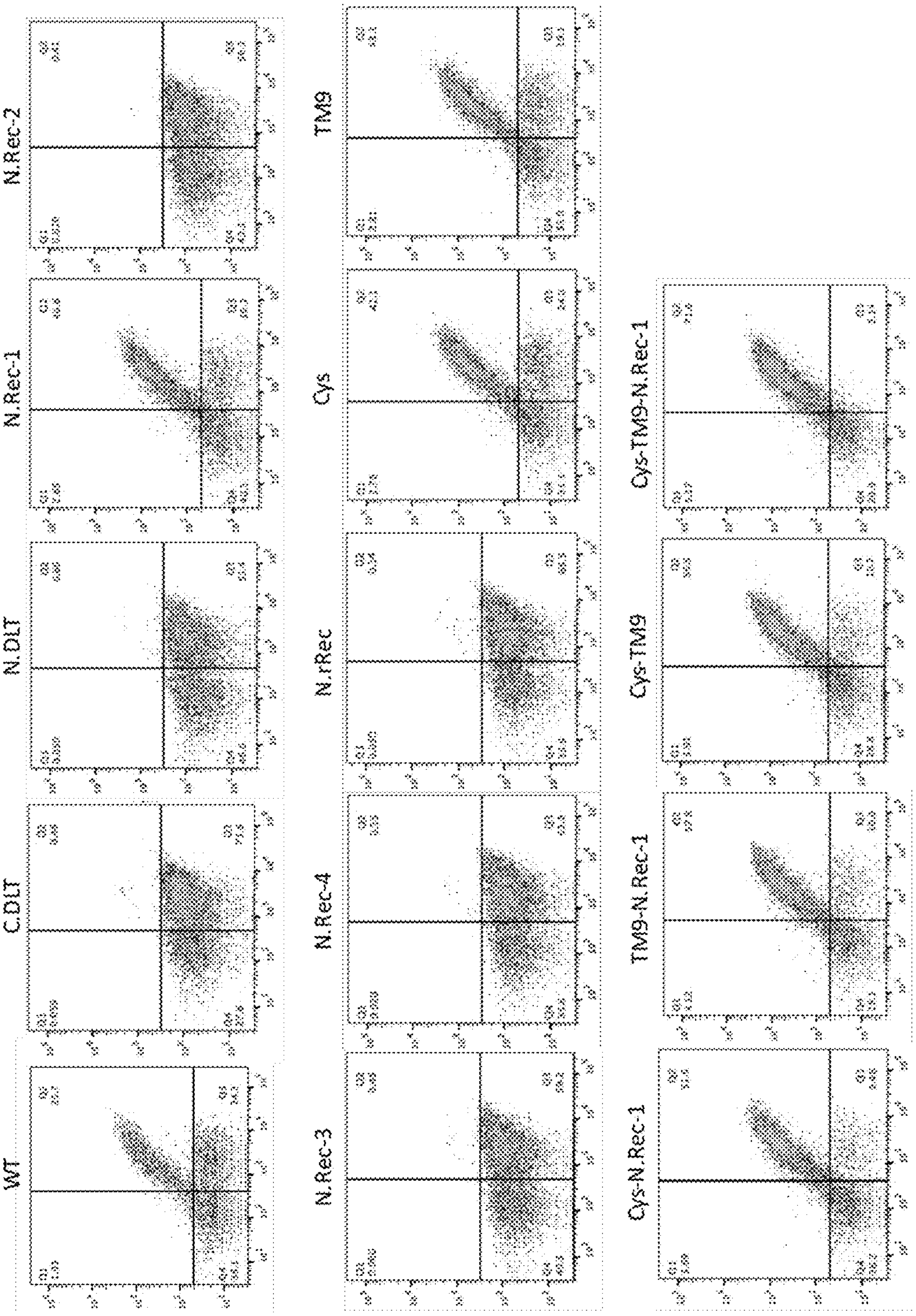

The above plasmids were packaged into viruses, cells were infected by the viruses, and the membrane forming efficiency of the STAR was detected. Results are shown in FIG. 6.

10.2. N-Terminal Modification on Constant Region of Anti-EGFR STAR Receptor and Functions of Rearranged Mutant 1) a Specific Sequence at an N Terminal of the Constant Region of the STAR was Deleted to Make the STAR Lose Functions.

By using a phge-EFIA-IRES-RFP vector, Mouse TCRa/bC-N.DLT STAR and Mouse TCRa/bC-WT STAR vectors were recombined and constructed through Gibbson Assembly; viruses were packaged by using Lentix-293T cells, and packaging plasmids were pSPAX and PMD2.G, wherein a ratio of Transfer plasmid to pSPAX to PMD2.G was 3:2:1; totally 18 μg of plasmids existed in each of 10 cm culture dishes, and a ratio of the plasmids in each culture dish to PEI-MAX was 1:3, i.e. 54 μL of PEI was used; the culture medium was changed 12 h after transfection, and virus solutions at 48 h and 72 h were harvested; after centrifugation for 2 h at 20000 rpm and 4°, a serum-free medium was used for resuspension; the viruses were concentrated by 100 times; and virus titers were detected. Results show that the virus packaging efficiency of Mouse TCRa/bC-N.DLT STAR is superior to that of Mouse TCRa/bC-WT STAR. Jurkat C5 and primary T cells were subjected to same MOI (multiplicity of infection), and it was discovered that there was no significant difference in infection efficiency. Discovered from RFP and EGFR-his-APC staining in the primary T cells, a membrane of Mouse TCRa/bC-N.DLT cannot be formed.

Discovered from co-culture with target cells A431, B16-tEGFR and A549, Mouse TCRa/bC-N.DLT does not have the killing ability and did not secrete cytokines IL-2, TNFα and IFNγ after being stimulated by EGFR antigen.

2) Rearrangement of a C Terminal of the Constant Region of the STAR Made the STAR Lose Functions.

By using the phge-EF1A-IRES-RFP vector, a Mouse TCRa/bC-C.DLT STAR vector was recombined and constructed through Gibbson Assembly; viruses were packaged by using Lentix-293T cells, and packaging plasmids were pSPAX and PMD2.G, wherein a packaging ratio of Transfer plasmid to pSPAX to PMD2.G was 3:2:1; totally 18 μg of plasmids existed in each of 10 cm culture dishes, and a ratio of the plasmids in each culture dish to PEI-MAX was 1:3, i.e. 54 μL of PEI was used; the culture medium was changed 12 h after transfection, and virus solutions at 48 h and 72 h were harvested; after centrifugation for 2 h at 20000 rpm and 4°, a serum-free medium was used for resuspension; the viruses were concentrated by 100 times; and virus titers were detected. The Jurkat C5 and the primary T cells were infected; discovered from western blotting, RFP and EGFR-his-APC staining in the primary T cells, Mouse TCRa/bC-C.DLT has protein expression but cannot be subjected to membrane formation; and it states that the sequence deleted from Mouse TCRa/bC-C.DLT is a key to the functions of the STAR and rearrangement of the STAR is not random.

3) Rearrangement of the N-Terminal of the Constant Region of the STAR Played a Vital Role.

By using the phge-EF1A-IRES-RFP vector, Mouse TCRa/bC-N.Rec-1 STAR, Mouse TCRa/bC-N.Rec-2 STAR, Mouse TCRa/bC-N.Rec-3 STAR, Mouse TCRa/bC-N.Rec-4 STAR and Mouse TCRa/bC-WT STAR vectors were recombined and constructed through Gibbson Assembly; viruses were packaged by using the Lentix-293T cells, and packaging plasmids were pSPAX and PMD2.G, wherein a packaging ratio of Transfer plasmid to pSPAX to PMD2.G was 3:2:1; totally 18 μg of plasmids existed in each of 10 cm culture dishes, and a ratio of the plasmids in each culture dish to PEI-MAX was 1:3, i.e. 54 μL of PEI was used; the culture medium was changed 12 h after transfection, and virus solutions at 48 h and 72 h were harvested; after centrifugation for 2 h at 20000 rpm and 4°, a serum-free medium was used for resuspension; the viruses were concentrated by 100 times; and virus titer were detected. A results shows that there was no obvious difference in virus titer. Discovered from infection of the Jurkat C5 and the primary T cells, there was no significant difference in infection efficiency. Discovered from RFP and EGFR-his-APC staining in the primary T cells, compared with Mouse TCRa/bC-WT STAR, Mouse TCRa/bC-N.Rec-1 was lower in mismatching ratio in the aspect of mismatching with endogenous TCR. Discovered from co-culture with target cells A431, B16-tEGFR and A549, Mouse TCRa/bC-N.Rec-1 has stronger target cell killing ability than Mouse TCRa/bC-WT STAR. Sequence analysis shows that Mouse TCRa/bC-N.Rec-1 is higher in sequence human origin than Mouse TCRa/bC-WT STAR. Immunogenicity prediction analysis shows that Mouse TCRa/bC-N.Rec is lower in immunogenicity than Mouse TCRa/bC-WT STAR. Meanwhile, deletions of Mouse TCRa/bC-N.Rec-2 STAR, Mouse TCRa/bC-N.Rec-3 STAR and Mouse TCRa/bC-N.Rec-4 STAR made the STAR lose the functions.

4) Rearrangement of the N Terminal of the Constant Region of the STAR has the Sequence Specificity, and Other Rearrangement Modes are Invalid.

By using the phge-EF1A-IRES-RFP vector, Mouse TCRa/bC-N.Rec-1 STAR and Mouse TCRa/bC-N.rRec STAR vectors were recombined and constructed through Gibbson Assembly; viruses were packaged by using the Lentix-293T cells, and packaging plasmids were pSPAX and PMD2.G, wherein a packaging ratio of Transfer plasmid to pSPAX to PMD2.G was 3:2:1; totally 18 μg of plasmids existed in each of 10 cm culture dishes, and a ratio of the plasmids in each culture dish to PEI-MAX was 1:3, i.e. 54 μL of PEI was used; the culture medium was changed 12 h after transfection, and virus solutions at 48 h and 72 h were harvested; after centrifugation for 2 h at 20000 rpm and 4°, a serum-free medium was used for resuspension; the viruses were concentrated by 100 times; and virus titers were detected. A results shows that there was no obvious difference in virus titer. Discovered from infection of the Jurkat C5 and the primary T cells, there was no significant difference in infection efficiency. Discovered from RFP and EGFR-his-APC staining in the primary T cells, compared with Mouse TCRa/bC-N.Rec-1, Mouse TCRa/bC-N.rRec has a significantly increased mismatching ratio. Discovered from co-culture with the target cells A431, B16-tEGFR and A549, the killing function of Mouse TCRa/bC-N.rRec was nearly lost and was greatly poorer than the function of Mouse TCRa/bC-N.Rec START.

10.3. Function of Mutant of Cysteine Point Mutation of Anti-EGFR STAR Receptor

With cysteine point mutation of the STAR receptor, an additional disulfide bond can be added to exert the effects of enhancing matching and stabilizing the complex. By using the phge-EF1A-IRES-RFP vector, the Mouse TCRa/bC-Cys STAR and Mouse TCRa/bC-WT STAR vectors were recombined and constructed through Gibbson Assembly; viruses were packaged by using the Lentix-293T cells, and packaging plasmids were pSPAX and PMD2.G, wherein a packaging ratio of Transfer plasmid to pSPAX to PMD2.G was 3:2:1; totally 18 μg of plasmids existed in each of 10 cm culture dishes, and a ratio of the plasmids in each culture dish to PEI-MAX was 1:3, i.e. 54 μL of PEI was used; the culture medium was changed 12 h after transfection, and virus solutions at 48 h and 72 h were harvested; after centrifugation for 2 h at 20000 rpm and 4°, a serum-free medium was used for resuspension; the viruses were concentrated by 100 times; and virus titers were detected. A results shows that there was no obvious difference in virus titer. Discovered from infection of the Jurkat C5 and the primary T cells, there was no significant difference in infection efficiency. Discovered from RFP and EGFR-his-APC staining in the primary T cells, compared with Mouse TCRa/bC-WT, Mouse TCRa/bC-Cys was significantly lowered in mismatching ratio in the aspect of mismatching with the endogenous TCR. Discovered from co-culture with target cells A431, B16-tEGFR and A549, Mouse TCRa/bC-Cys has stronger target cell killing ability than Mouse TCRa/bC-WT. Mouse TCRa/bC-Cys was higher in secretion level of the cytokines IL-2, TNFα and IFNγ after being stimulated by the EGFR antigen.

10.4. Function of Conducting Hydrophobic Amino Acid Substitution at Specific Site of Transmembrane Region of Anti-EGFR STAR Receptor Hydrophobic amino acid substitution on a transmembrane region of the STAR receptor at a specific site plays a key role. With cysteine point mutation of the STAR receptor, an additional disulfide bond can be added to exert the effects of enhancing matching and stabilizing the complex. By using the phge-EF1A-IRES-RFP vector, Mouse TCRa/bC-TM9 STAR and Mouse TCRa/bC-WT STAR vectors were recombined and constructed through Gibsson Assembly; viruses were packaged by using the Lentix-293T cells, and packaging plasmids were pSPAX and PMD2.G, wherein a packaging ratio of Transfer plasmid to pSPAX to PMD2.G was 3:2:1; totally 18 μg of plasmids existed in each of 10 cm culture dishes, and a ratio of the plasmids in each culture dish to PEI-MAX was 1:3, i.e. 54 μL of PEI was used; the culture medium was changed 12 h after transfection, and virus solutions at 48 h and 72 h were harvested; after centrifugation for 2 h at 20000 rpm and 4°, a serum-free medium was used for resuspension; the viruses were concentrated by 100 times; and virus titers were detected. A results shows that there was no obvious difference in virus titer. Discovered from infection of the Jurkat C5 and the primary T cells, there was no significant difference in infection efficiency. Discovered from RFP and EGFR-his-APC staining in the primary T cells, compared with Mouse TCRa/bC-WT, Mouse TCRa/bC-TM9 was significantly lowered in mismatching ratio in the aspect of mismatching with the endogenous TCR. Discovered from co-culture with target cells A431, B16-tEGFR and A549, Mouse TCRa/bC-TM9 has stronger target cell killing ability than Mouse TCRa/bC-WT. Mouse TCRa/bC-Cys was higher in secretion level of the cytokines IL-2, TNFα and IFNγ after being stimulated by the EGFR antigen.

10.5. Function of Comprehensive Mutant of Anti-EGFR STAR

To compare the effects of triple combination, pair combination and single modification of modification strategies (N-terminal modification, Cys substitution and transmembrane region hydrophobic modification) of the constant region, by using the phge-EF1A-IRES-RFP vector, all STAR vectors in a following table were recombined and constructed through Gibsson Assembly; viruses were packaged by using Lentix-293T cells, and packaging plasmids were pSPAX and PMD2.G, wherein a packaging ratio of Transfer plasmid to pSPAX to PMD2.G was 3:2:1; totally 18 μg of plasmids existed in each of 10 cm culture dishes, and a ratio of the plasmids in each culture dish to PEI-MAX was 1:3, i.e. 54 μL of PEI was used; the culture medium was changed 12 h after transfection, and virus solutions at 48 h and 72 h were harvested; after centrifugation for 2 h at 20000 rpm and 4°, a serum-free medium was used for resuspension; the viruses were concentrated by 100 times; and virus titers were detected. Discovered from infection of the Jurkat C5 and the primary T cells, after the T cells were infected with same MOI, there was no significant difference in the infection efficiency (i.e. RFP positive rate). Discovered from RFP and EGFR-his-APC antibody staining, the mismatching ratio of a paired mutation combination was significantly lower than that of a single mutation strategy. In the case with same RFP positive cells, the killing ability of the STAR-T cells in paired mutation to the target cells A431, B16-htEGFR and A549 was significantly higher than that of the single mutation strategy; and the secretion levels of the cytokines IL-2, TNFα and IFNγ are further higher. However, if the three mutation strategies are combined together at the same time, it shows the lowest mismatching ratio, stronger killing ability to the target cells at the same time and higher secretion levels of the cytokines. Overall results are shown in FIG. 6.

| Comparative object 1 | Comparative object 2 | Result |
|---|---|---|
| TCRa/bC-Cys-N.Rec-1 | TCRa/bC-Cys and TCRa/bC-N.Rec-1 | Paired combination of the modification strategies of the constant region has better effect than the single modification. |
| TCRa/bC-Cys-TM9 | TCRa/bC-Cys and TCRa/bC-TM9 | |
| TCRa/bC-N.Rec-1-TM9 | TCRa/bC-N.Rec-1 and TCRa/bC-TM9 | |
| TCRa/bC-Cys-N.Rec-1-TM9 | TCRa/bC-N.Rec-1, TCRa/bC-Cys, TCRa/bC-TM9, TCRa/bC-Cys-N.Rec-1, TCRa/bC-Cys-TM9 and TCRa/bC-N.Rec-1-TM9 | The triple combination of the modification strategies of the constant region has better effect that the paired combination and the single modification. |

Example 11. N-Terminal Modification on Constant Region of Anti-GPC3 STAR Receptor and Functions of Rearranged Mutant Based on the mutation strategies in embodiment 1, the present invention conducted optimization solutions such as sequence truncation, rearrangement and C-terminal rearrangement for a constant region. For GPC3, antibody sequence selected a monoclonal antibody GC33 aiming to GPC3; an antibody heavy chain variable region (anti-GPC3 GC33-VH, SEQ ID NO: 25) and an antibody light chain variable region (anti-GPC3 GC33-VL, SEQ ID NO: 24) used a phage-EF1A-IRES-RFP vector; vectors of Mouse GC33-VH TCRa-GC33-VL TCRbC-N.DLT STAR, Mouse GC33-VH TCRa-GC33-VL TCRbC-C.DLT STAR, Mouse GC33-VH TCRa-GC33-VL TCRbC-N.Rec-1 STAR, Mouse GC33-VH TCRa-GC33-VL TCRbC-N.Rec-2 STAR, Mouse GC33-VH TCRa-GC33-VL TCRbC-N.Rec-3 STAR, Mouse GC33-VH TCRa-GC33-VL TCRbC-N.Rec-4 STAR, Mouse GC33-VH TCRa-GC33-VL TCRbC-WT STAR and the like were recombined and constructed through Gibsson Assembly. Viruses were packaged by using Lentix-293T cells, and packaging plasmids were pSPAX and PMD2.G, wherein a packaging ratio of Transfer plasmid to pSPAX to PMD2.G was 3:2:1; totally 18 μg of plasmids existed in each of 10 cm culture dishes, and a ratio of the plasmids in each culture dish to PEI-MAX was 1:3, i.e. 54 μL of PEI was used; the culture medium was changed 12 h after transfection, and virus solutions at 48 h and 72 h were harvested; after centrifugation for 2 h at 20000 rpm and 4°, a serum-free medium was used for resuspension; the viruses were concentrated by 100 times; and virus titers were detected. Results are shown in FIG. 7.

1) Truncation of a Specific Sequence at an N Terminal of the Constant Region of the STAR Made the STAR Lose Functions.

Results show Mouse GC33-VH TCRa-GC33-VL TCRbC-N.DLT STAR and Mouse GC33-VH TCRa-GC33-VL TCRbC-WT STAR. Jurkat C5 and primary T cells were subjected to same MOI, and it was discovered that there was no significant difference in infection efficiency. Discovered from RFP and GPC3-FITC staining in the primary T cells, a membrane of Mouse GC33-VH TCRa-GC33-VL TCRbC-N.DLT cannot be formed. Discovered from co-culture with target cells Huh-7 and HepG2 cells, Mouse GC33-VH TCRa-GC33-VL TCRbC-N.DLT does not have the killing ability.

2) Rearrangement of a C Terminal of the Constant Region of the STAR Made the STAR Lose Functions.

The Jurkat C5 and the primary T cells were infected; discovered from western blotting, RFP and GPC3-FITC staining in the primary T cells, Mouse GC33-VH TCRa-GC33-VL TCRbC-C.DLT could not be subjected to membrane formation; and it stated that the sequence deleted from Mouse GC33-VH TCRa-GC33-VL TCRbC-C.DLT was a key to the functions of the STAR and rearrangement of the STAR was not random. Discovered from co-culture with the target cells Huh-7 and the HepG2 cells, Mouse GC33-VH TCRa-GC33-VL TCRbC-C.DLT does not have the killing function.

3) Rearrangement of the N-Terminal of the Constant Region of the STAR Played a Vital Role.

Discovered from infection of the Jurkat C5 and the primary T cells, there was no significant difference in infection efficiency. Discovered from RFP and EGFR-his-APC staining in the primary T cells, compared with Mouse GC33-VH TCRa-GC33-VL TCRbC-WT STAR, Mouse GC33-VH TCRa-GC33-VL TCRbC-N.Rec-1 was lower in mismatching ratio in the aspect of mismatching with endogenous TCR. Discovered from co-culture with the target cells Huh-7 and the HepG2 cells, MouseGC33-VH TCRa-GC33-VL TCRbC-N.Rec-1 has stronger target cell killing ability than Mouse GC33-VH TCRa-GC33-VL TCRbC-WT STAR. Sequence analysis shows that Mouse GC33-VH TCRa-GC33-VL TCRbC-N.Rec-1 was higher in sequence human origin than Mouse GC33-VH TCRa-GC33-VL TCRbC-WT STAR. Immunogenicity prediction analysis shows that Mouse GC33-VH TCRa-GC33-VL TCRbC-N.Rec was lower in immunogenicity than Mouse GC33-VH TCRa-GC33-VL TCRbC-WT STAR. Meanwhile, deletions of Mouse GC33-VH TCRa-GC33-VL TCRbC-N.Rec-2 STAR, Mouse GC33-VH TCRa-GC33-VL TCRbC-N.Rec-3 STAR and Mouse GC33-VH TCRa-GC33-VL TCRbC-N.Rec-4 STAR made the STAR lose the functions.

4) Rearrangement of the N Terminal of the Constant Region of the STAR has the Sequence Specificity, and Other Rearrangement Modes are Invalid.

Discovered from RFP and EGFR-his-APC staining in the primary T cells, compared with Mouse GC33-VH TCRa-GC33-VL TCRbC-N.Rec-1, for Mouse GC33-VH TCRa-GC33-VL TCRbC-N.rRec, GC33 scFv cannot be subjected to membrane formation. Discovered from co-culture with the target cells Huh-7 and the HepG2 cells, the killing function of Mouse GC33-VH TCRa-GC33-VL TCRbC-N.rRec was lost and was greatly poorer than the function of Mouse GC33-VH TCRa-GC33-VL TCRbC-N.Rec START.

Example 12. Function of Mutant of Cysteine Point Mutation of Anti-GPC3 STAR Receptor With cysteine point mutation of the STAR receptor, an additional disulfide bond can be added to exert the effects of enhancing matching and stabilizing the complex. By using the phage-EFIA-IRES-RFP vector, Mouse GC33-VH TCRa-GC33-VL TCRbC-Cys STAR and Mouse GC33-VH TCRa-GC33-VL TCRbC-WT STAR vectors were recombined and constructed through Gibsson Assembly; viruses were packaged by using the Lentix-293T cells, and packaging plasmids were pSPAX and PMD2.G, wherein a packaging ratio of Transfer plasmid to pSPAX to PMD2.G was 3:2:1; totally 18 μg of plasmids existed in each of 10 cm culture dishes, and a ratio of the plasmids in each culture dish to PEI-MAX was 1:3, i.e. 54 μL of PEI was used; the culture medium was changed 12 h after transfection, and virus solutions at 48 h and 72 h were harvested; after centrifugation for 2 h at 20000 rpm and 4°, a serum-free medium was used for resuspension; the viruses were concentrated by 100 times; and virus titers were detected. A results shows that there was no obvious difference in virus titer. Discovered from infection of the Jurkat C5 and the primary T cells, there was no significant difference in infection efficiency. Discovered from RFP and GPC3-FITC staining in the primary T cells, compared with Mouse GC33-VH TCRa-GC33-VL TCRbC-WT, Mouse GC33-VH TCRa-GC33-VL TCRbC-Cys was significantly lowered in mismatching ratio in the aspect of mismatching with the endogenous TCR. Discovered from co-culture with target cells Huh-7 and HepG2 cells, Mouse GC33-VH TCRa-GC33-VL TCRbC-Cys has stronger target cell killing ability than Mouse GC33-VH TCRa-GC33-VL TCRbC-WT.

Example 13. Function of Conducting Hydrophobic Amino Acid Substitution at Specific Site of Transmembrane Region of Anti-GPC3 STAR Receptor Hydrophobic amino acid substitution on a transmembrane region of the STAR receptor at a specific site plays a key role. With cysteine point mutation of the STAR receptor, an additional disulfide bond can be added to exert the effects of enhancing matching and stabilizing the complex. By using a phage-EF1A-IRES-RFP vector, Mouse GC33-VH TCRa-GC33-VL TCRbC-TM9 STAR and Mouse GC33-VH TCRa-GC33-VL TCRbC-WT STAR vectors were recombined and constructed through Gibsson Assembly; viruses were packaged by using the Lentix-293T cells, and packaging plasmids were pSPAX and PMD2.G, wherein a packaging ratio of Transfer plasmid to pSPAX to PMD2.G was 3:2:1; totally 18 μg of plasmids existed in each of 10 cm culture dishes, and a ratio of the plasmids in each culture dish to PEI-MAX was 1:3, i.e. 54 μL of PEI was used; the culture medium was changed 12 h after transfection, and virus solutions at 48 h and 72 h were harvested; after centrifugation for 2 h at 20000 rpm and 4°, a serum-free medium was used for resuspension; the viruses were concentrated by 100 times; and virus titers were detected. A results shows that there was no obvious difference in virus titer. Discovered from infection of the Jurkat C5 and the primary T cells, there was no significant difference in infection efficiency. Discovered from RFP and GPC3-FITC protein staining in the primary T cells, compared with Mouse GC33-VH TCRa-GC33-VL TCRbC-WT, Mouse GC33-VH TCRa-GC33-VL TCRbC-TM9 was significantly lowered in mismatching ratio in the aspect of mismatching with the endogenous TCR. Discovered from co-culture with target cells Huh-7 and HepG2 cells, Mouse GC33-VH TCRa-GC33-VL TCRbC-TM9 has stronger target cell killing ability than Mouse GC33-VH TCRa-GC33-VL TCRbC-WT.

Example 14. Function of Comprehensive Mutant of Anti-GPC3 STAR

To compare the effects of triple combination, pair combination and single mutation of modification strategies, by using a phage-EF1A-IRES-RFP vector, all STAR vectors in a following table were recombined and constructed through Gibsson Assembly; viruses were packaged by using Lentix-293T cells, and packaging plasmids were pSPAX and PMD2.G, wherein a packaging ratio of Transfer plasmid to pSPAX to PMD2.G was 3:2:1; totally 18 μg of plasmids existed in each of 10 cm culture dishes, and a ratio of the plasmids in each culture dish to PEI-MAX was 1:3, i.e. 54 μL of PEI was used; the culture medium was changed 12 h after transfection, and virus solutions at 48 h and 72 h were harvested; after centrifugation for 2 h at 20000 rpm and 4°, a serum-free medium was used for resuspension; the viruses were concentrated by 100 times; and virus titers were detected. Discovered from infection of the Jurkat C5 and the primary T cells, after the T cells were infected with same MOI, there was no significant difference in the infection efficiency (i.e. RFP positive rate). Discovered from RFP and GPC3-FITC protein staining, the membrane formation efficiency of a paired mutation combination was significantly higher than that of a single mutation strategy. In the case with same RFP positive cells, the killing ability of the STAR-T cells in paired mutation to target cells Huh-7 and HepG2 cells was significantly higher than that of the single mutation strategy; and However, if the three mutation strategies are combined together at the same time, it shows the lowest mismatching ratio, stronger killing ability to the target cells at the same time and higher secretion levels of the cytokines. Specific results are shown in FIG. 7.

The strategies were compared aiming to a GPC3 GC33 STAR mutant:

| Comparative object 1 | Comparative object 2 | Result |
|---|---|---|
| Cys-N.Rec-1<br>Cys-TM9<br>N.Rec-1-TM9 | Cys and N.Rec-1<br>Cys and TM9<br>N.Rec-1 and TM9 | Paired combination of the mutation strategies has better effect than the single mutation. |
| Cys-N.Rec-1-TM9 | N.Rec-1, Cys, TM9, Cys-N.Rec-1, Cys-TM9 and N.Rec-1-TM9 | Triple combination of the mutation strategies has better effect that the paired combination and the single mutation. |

Example 15. Function of Comprehensive Mutant of Anti-CD19 STAR Based on 334-scFv The inventor obtains a novel monoclonal antibody 334 targeting CD19, produced by hybridoma cells with a preservation number of CGMCC No. 17095 (preserved in China General Microbiological Culture Collection Center of Institute of Microbiology, Chinese Academy of Sciences with an address of No. 3, Courtyard No. 1, Beichen Western Road, Chaoyang district of Beijing, at Jan. 21, 2019). The antibody contains anti-CD19 334 VL (SEQ ID NO: 27) and anti-CD19 334 VH (SEQ ID NO: 26), wherein the anti-CD19 334 VH contains a heavy chain CDR1 shown as SEQ ID NO: 28, a heavy chain CDR2 shown as SEQ ID NO: 29 and a heavy chain CDR3 shown as SEQ ID NO: 30; the anti-CD19 334 VL contains a light chain CDR1 shown as SEQ ID NO: 31, a light chain CDR2 shown as SEQ ID NO: 32 and a light chain CDR3 shown as SEQ ID NO: 33.

1) Specific Recognition of CD19 with Antibody 334

Recognition ability of an antibody 334 to a target antigen CD19 and a nontarget antigen CD20 was identified by using an ELISA method; plasmids expressing the antibody 334 were transformed to 293T cells by using a transfection reagent PEI; and after 72 h, a cell supernatant was collected, and the antigen-antibody specific binding ability was detected by using the ELISA method. Experimental results show that the antibody 334 was significantly specifically bound to the target antigen CD19 and has no binding ability to the nontarget antigen CD20.

To verify that the CD19-334 antibody may specifically recognize the antigen CD19 expressed by human cells, a WB test was used to detect the recognition ability of the CD19-334 antibody to a humanized CD19 antibody.

2) Preparation of a CD19 Positive Protein Sample:

Raji cells (high positive expression for the CD19 antibody) in a human lymphoma cell line were conventionally cultured; and after 90% cells were fused, and 6 cm dish of suspension cells were taken for centrifugation, a cell precipitate was collected into a 1.5 mL centrifuge tube. 200 μL of total protein extraction lysis reagent (RIPA) was added for full beating and uniform mixing, and then lysis on ice was conducted for 15 min. The centrifuge tube was placed in a low-temperature refrigerated centrifuge precooled at 4° C. for centrifugation 15 min at 4° C. and 12000 rpm, and a supernatant was collected. 5×loading buffer was added for protein denaturation for 5 min at 100° C. A sample was precooled on ice for 20 after was subjected to centrifugation and then subjected to WB electrophoresis (with a human rectal cancer cell line M62 as cells in a CD19 negative control group).

(2) WB electrophoresis: 4% spacer gel was prepared, and a separation gel was 10% SDS-PAGE running gel. 40 μL of extracted CD19 positive protein sample and 40 μL of extracted CD19 negative protein sample were added to each well. Electrophoresis was conducted for 20 min at 80V; and then a voltage was adjusted to 120V, and electrophoresis was conducted for 40-60 min.

(3) Membrane transfer: a half-dry transferring system was used to transfer a target protein to 0.45 μm PVDF membrane. Membrane transfer conditions were 15 V and 1 h.

(4) Closure: the PVDF membrane after transferred was placed in 5% skim milk powder for closure and was shaken by a shaker for 1 h at a room temperature.

(5) Primary antibody incubation: residual milk powder on the PVDF membrane was cleanly washed with PBST, residual buffer was sucked to dryness by using filter paper, and the PVDF membrane was put in a primary antibody incubation box containing CD19 antibody hybridoma supernatant (5-8 mL). Incubation was conducted at 4° C. overnight.

(6) PBST rinsing: 5 min×3.

(7) Secondary antibody incubation: the PVDF was placed in ant-mouse (1:20000) monoclonal antibody marked by HRP Incubation was conducted for 1 h at the room temperature.

(8) PBST rinsing: 5 min×3.

(9) Developing and potograghing were conducted with a gel imager.

Experimental results show that the antibody 334 may recognize the CD19 protein (with size of a target band of 95 kD) in the Raji cells in the human lymphoma cell line.

3) Detection on Kd Value of Antibody 334

Raji cells (high positive expression for the CD19 antibody) in a human lymphoma cell line were conventionally cultured; after 90% cells were fused, and 6 cm dish of suspension cells were taken for centrifugation, a cell precipitate was collected into a 1.5 mL centrifuge tube; and the cell precipitate was resuspended with PBS, and a cell density was adjusted to $5\times10^6$ cells/mL.

$5\times10^6$ Raji cells per well were added to a 96-well plate; the antibody 334 was diluted and purified to 375 nM, 187.5 nM, 30 nM, 3 nM, 0.3 nM, 0.03 nM, 0.003 nM and 0 nM and added to the Raji cells in the 96-well plate for incubation for 30 min at 4° C.; then, centrifugation was conducted for 5 min at 2000 rpm, and a supernatant was abandoned; after the PBS was added for cleaning the cells once, a goat-anti mouse AlexaFluor 555 fluorescence second antibody was added for incubating the Raji cells for 30 min. Incubation was conducted for 30 min at 4° C., centrifugation was conducted for 5 min at 2000 rpm, and a supernatant was abandoned; after the PBS was added for cleaning the cells once, 200 μL of PBS was added for resuspending the cells; the fluorescence intensities of the Raji cells under different concentrations of the CD19-334 antibody were detected by using flow cytometry; and computation was conducted by using a GraphPad software to obtain a Kd value of the CD19-334 antibody.

Detection results show a binding curve fitted by the fluorescence intensities of the Raji cells under different concentrations; and the Kd value, computed by the GraphPad software, of the CD19-334 antibody was 1.528±0.25 nM.

4) Comprehensive Mutant of Anti-CD19 STAR Based on 334-scFv

Figure 8:
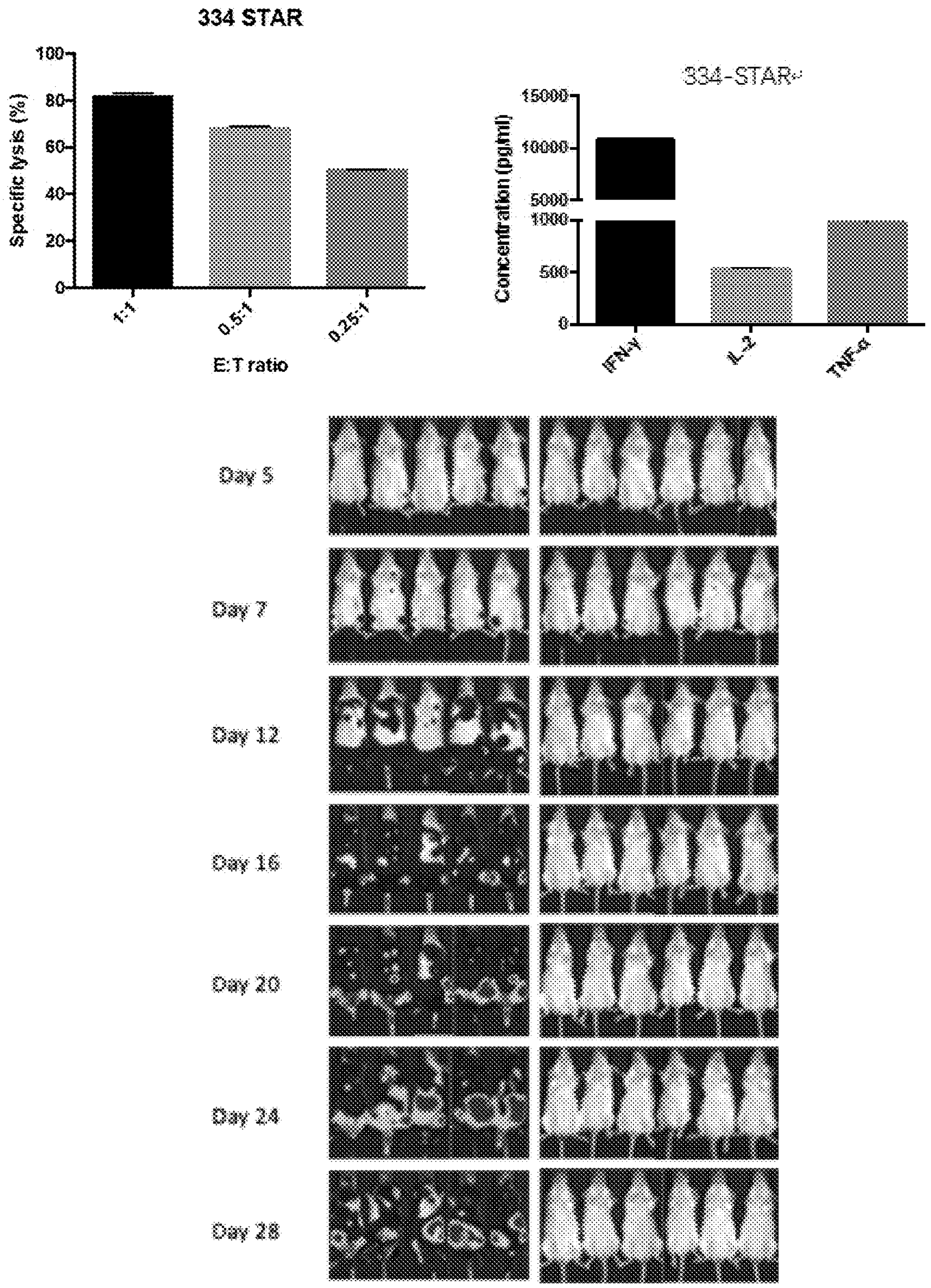
FIG. 8 shows function of an integrated mutant of 334 STAR targeting CD19.

A myc-Cys-N.Rec-1-TM9-STAR-334-anti-CD19 STAR structure was constructed on the basis of the pHAGE-IRES-RFP vector. Used antibody binding sequences are anti-CD19 334 VL (SEQ ID NO: 27) and anti-CD19 334 VH (SEQ ID NO: 26), wherein the anti-CD19 334 VH contains a heavy chain CDR1 shown as SEQ ID NO: 28, a heavy chain CDR2 shown as SEQ ID NO: 29 and a heavy chain CDR3 shown as SEQ ID NO: 30; the anti-CD19 334 VL contains a light chain CDR1 shown as SEQ ID NO: 31, a light chain CDR2 shown as SEQ ID NO: 32 and a light chain CDR3 shown as SEQ ID NO: 33. After viruses were packaged with second-generation packaging plasmids, Jurkat C5 cells were infected. Discovered from flow cytometry results, STAR may be subjected to normal membrane formation and may promote expressions of activated molecules such as CD69 and CD25 by binding to the target cells Raji and the antibody CD19 protein. After primary T cells were infected with the viruses, co-culture of the T cells with the target cells Raji, Jeko-1 and the like may obviously stimulate the T cells to secrete IL-2, TNF-α and IFNγ and induce the T cells to kill the target cells; and meanwhile, the T cells further express immunosuppressive molecules PD1, TIM3, LAG3 and the like, which further states that the T cells are activated and exert a killing function. A lymphoma model was established on NSG mice with the Raji cells; anti-CD19 STAR T cells were used to act on tumor-bearing mice; and then compared with a control group, the anti-CD19 STAR T cells might obviously have the killing effect on tumors. Results are shown in FIG. 8.

Example 16. Function of Comprehensive Mutant of FMC63-2C6 STAR for CD19-CD20

Figure 9:
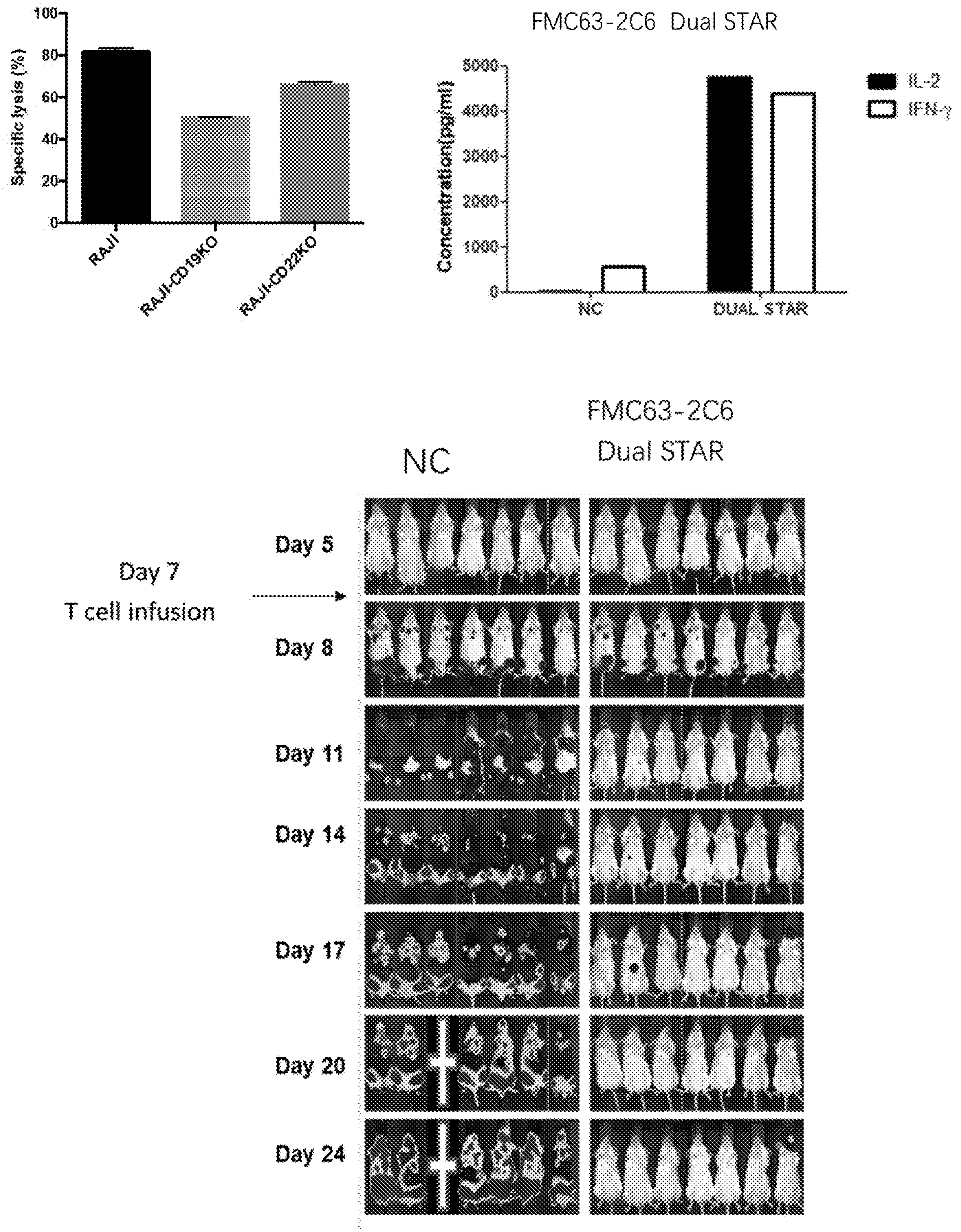
FIG. 9 shows function of an integrated mutant of FMC63-2C6 STAR targeting CD19/CD20.

In the structure of STAR, Cα and Cβ may be linked to VH and VL of scFv and may further be linked to different scFv; and therefore, it is possible in the aspect of double targets or double recognition sites at single target. A myc-Cys-N.Rec-1-TM9-STAR-anti-CD19/CD20 STAR structure was constructed on the basis of a pHAGE-IRES-RFP vector, wherein an a target selected FMC63 monoclonal antibody (FMC63 VH seq NO: 44, FMC63 VL seq NO: 45) for CD19 and a 2C6 monoclonal antibody (2C6 VH seq NO: 46, 2C6 VL seq NO: 47) for CD20. A myc-Cys-N.Rec-1-TM9-STAR-FMC63-2C6 structure was constructed; after viruses were packaged with second-generation packaging plasmids, Jurkat C5 cells were infected. Discovered from flow cytometry results, STAR may be subjected to normal membrane formation. After primary T cells were infected with the viruses, co-culture of the T cells with the target cells Raji, Raji-CD19KO and Raji-CD20KO may obviously stimulate the T cells to secrete IL-2, TNF-α and IFNγ and induce the T cells to kill the target cells, which states that FMC63-2C6 STAR have good killing ability two both targets, and tumor recurrence caused by loss of one of the two targets may be clinically avoided. A tumor-bearing model was established on the NSG mice with 90% Raji+5% Raji-CD19KO+5% Raji-CD20KO cells; and after the FMC63-2C6 STAR cells were used to act on the tumor-bearing mice, compared with the control group, the FMC63-2C6 STAR cells might obviously fully eliminated the tumors, which further proves that the FMC63-2C6 STAR cells have the killing effect on the both target. Results are shown in FIG. 9.

Example 17. Function of Comprehensive Mutant of 334-M971 STAR for CD19-CD22

Figure 10:
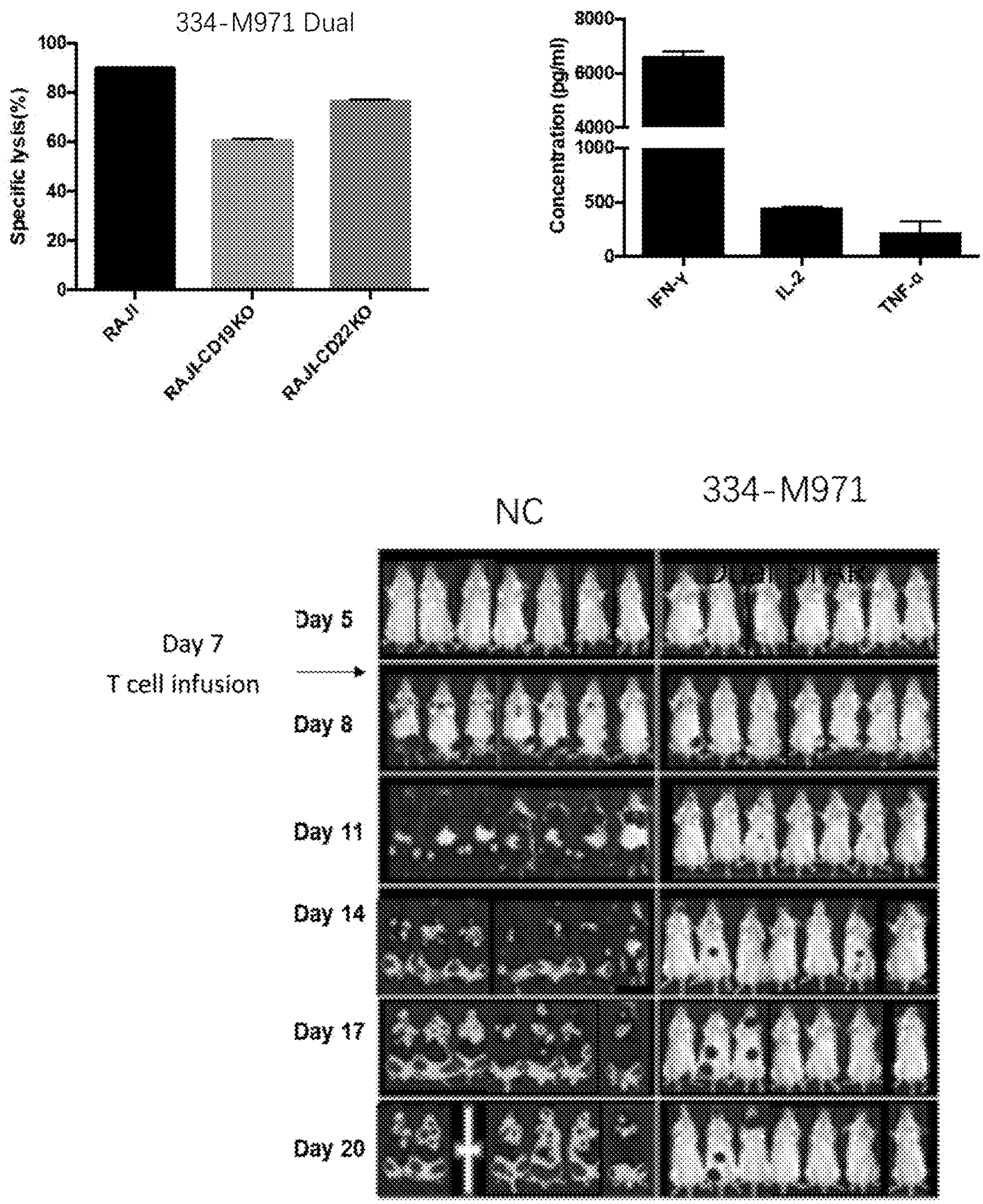
FIG. 10 shows function of an integrated mutant of FMC63-M791 STAR targeting CD19/CD22.

In the structure of STAR, Ca and CB may be linked to VH and VL of scFv and may further be linked to different scFv; and therefore, it is possible in the aspect of double targets or double recognition sites at single target. A myc-Cys-N.Rec-1-TM9-STAR-anti-CD19/CD22 STAR structure was constructed on the basis of a pHAGE-IRES-RFP vector, wherein an a target selected 334 monoclonal antibody (334 VH seq NO: 26, 334 VL seq NO: 27) for CD19 and a M971 monoclonal antibody (M971 VH seq NO: 48, 2 M971 VL seq NO: 49) for CD22. A myc-Cys-N.Rec-1-TM9-STAR-334-M971 structure was constructed; after viruses were packaged with second-generation packaging plasmids, Jurkat C5 cells were infected. Discovered from flow cytometry results, STAR may be subjected to normal membrane formation. After primary T cells were infected with the viruses, co-culture of the T cells with the target cells Raji, Raji-CD19KO and Raji-CD22KO may obviously stimulate the T cells to secrete IL-2, TNF-α and IFNγ and induce the T cells to kill the target cells, which states that 334-M971 STAR have good killing ability two both targets, and tumor recurrence caused by loss of one of the two targets may be clinically avoided. A tumor-bearing model was established on the NSG mice with 90% Raji+5% Raji-CD19KO+5% Raji-CD22KO cells; and after the 334-M971 STAR cells were used to act on the tumor-bearing mice, compared with the control group, the FMC63-2C6 STAR cells might obviously fully eliminated the tumors, which further proves that the FMC63-2C6 STAR cells have the killing effect on the both target. Results are shown in FIG. 10.

The invention claimed is:

1. A synthetic T-cell receptor and antigen receptor (STAR), containing an α chain and a β chain; the α chain containing a first antigen-binding region and a first constant region, and the β chain containing a second antigen-binding region and a second constant region, wherein the first constant region is derived from the constant region of the α chain of the mouse T-cell receptor; and compared with the constant region of the α chain of the natural mouse T-cell receptor, amino acids at positions 1~4 at the N-terminus are deleted, and amino acids from position 5 to position 18 at the N-terminus are substituted by corresponding amino acids in the constant region of the α chain of the natural human T-cell receptor; and numbers of the amino acids refer to SEQ ID NO: 2; and/or wherein the second constant region is derived from the constant region of the β chain of the mouse T-cell receptor; and compared with the constant region of the β chain of the natural mouse T-cell receptor, amino acids at positions 1-6 at the N-terminus are deleted, and amino acids from position 7 to position 25 at the N-terminus are substituted by corresponding amino acids in the constant region of the β chain of the natural human T-cell receptor; and numbers of the amino acids refer to SEQ ID NO: 15.

2. The synthetic T-cell receptor and antigen receptor according to claim 1, wherein compared with the constant region of the α chain of the natural mouse T-cell receptor, the first constant region contains a cysteine substitution at position 48; and numbers of the amino acids refer to SEQ ID NO: 2.

3. The synthetic T-cell receptor and antigen receptor according to claim 1, wherein compared with the constant region of the α chain of the natural mouse T-cell receptor, in the first constant region, threonine at position 48 is mutated to cysteine; and numbers of the amino acids refer to SEQ ID NO: 2.

4. The synthetic T-cell receptor and antigen receptor according to claim 1, wherein compared with the constant region of the α chain of the natural mouse T-cell receptor, the first constant region contains hydrophobic amino acid substitution in the transmembrane region; the transmembrane region, comprises an amino acid sequence from position 111 to position 119; and numbers of the amino acids refer to SEQ ID NO: 2.

5. The synthetic T-cell receptor and antigen receptor according to claim 1, wherein compared with the constant region of the α chain of the natural mouse T-cell receptor, the first constant region contains hydrophobic amino acid substitutions at position 112, position 114 and/or position 115; and numbers of the amino acids refer to SEQ ID NO: 2.

6. The synthetic T-cell receptor and antigen receptor according to claim 1, wherein compared with the constant region of the α chain of the natural mouse T-cell receptor, in the first constant region, serine at position 112 is substituted by leucine, methionine at position 114 is substituted by isoleucine, and/or glycine at position 115 is substituted by valine; and numbers of the amino acids refer to SEQ ID NO: 2.

7. The synthetic T-cell receptor and antigen receptor according to claim 1, wherein the first constant region contains a transmembrane region shown as SEQ ID NO: 8.

8. The synthetic T-cell receptor and antigen receptor according to claim 1, wherein the first constant region comprises an amino acid sequence selected from the amino acid sequences shown as SEQ ID NOs: 11-13 and 34.

9. The synthetic T-cell receptor and antigen receptor according to claim 1, wherein compared with the constant region of the β chain of the natural mouse T-cell receptor, in the second constant region, serine at position 56 is mutated to cysteine;

and numbers of the amino acids refer to SEQ ID NO: 15.

10. The synthetic T-cell receptor and antigen receptor according to claim 1, wherein the second constant region comprises an amino acid sequence selected from amino acid sequences shown as SEQ ID NOs: 21 and 37.

11. The synthetic T-cell receptor and antigen receptor according to claim 1, wherein:

i) the first constant region comprises the amino acid sequence shown as SEQ ID NO: 34, and the second constant region contains the amino acid sequence shown as SEQ ID NO: 37;

ii) the first constant region comprises the amino acid sequence shown as SEQ ID NO: 11, and the second constant region contains the amino acid sequence shown as SEQ ID NO: 21;

iii) the first constant region comprises the amino acid sequence shown as SEQ ID NO: 12, and the second constant region contains the amino acid sequence shown as SEQ ID NO: 37;

iv) the first constant region comprises the amino acid sequence shown as SEQ ID NO: 13, and the second constant region contains the amino acid sequence shown as SEQ ID NO: 21.

12. The synthetic T-cell receptor and antigen receptor according to claim 1, wherein the first antigen-binding region and the second antigen-binding region specifically bind to a target antigen independently or in combination.

13. The synthetic T-cell receptor and antigen receptor according to claim 12, wherein the target antigen is selected from the following antigens: CD16, CD64, CD78, CD96, CLL1, CD116, CD117, CD71, CD45, CD71, CD123, CD138, ErbB2 (HER2/neu), carcino-embryonic antigen (CEA), epithelial cell adhesion molecule (EpCAM), epidermal growth factor receptor (EGFR), EGFR variant III (EGFRvIII), CD19, CD20, CD30, CD40, disialoganglioside GD2, ductal epithelial mucin, gp36, TAG-72, glycosphingolipid, glioma-related antigen, β-human chorionic gonadotropin, α fetoprotein (AFP), lectin reactive AFP, thyroglobulin, RAGE-1, MN-CA IX, human telomerase reverse transcriptase, RU1, RU2(AS), intestinal carboxylesterase, mut hsp70-2, M-CSF, prostate specific antigen (PSA), PAP, NY-ESO-1, LAGA-1a, p53, Prostein, Prostate-Specific Membrane Antigen (PSMA), survivin, telomerase, prostate cancer tumor antigen-1 (PCTA-1), MAGE, ELF2M, a neutrophil elastase, ephrin B2, CD22, insulin-like growth factor (IGF1)-I, IGF-II, an IGFI receptor, mesothelin, a major histocompatibility complex (MHC) molecule presenting a tumor-specific peptide epitope, 5T4, ROR1, Nkp30, NKG2D, a tumor stroma antigen, extra domain A (EDA) and/or extra domain B (EDB) of fibronectin, tenascin-C A1 domain (TnC A1), fibroblast associated protein (FAP), CD3, CD4, CD8, CD24, CD25, CD33, CD34, CD133, CD138, Foxp3, B7-1 (CD80), B7-2 (CD86), GM-CSF, a cytokine receptor, an endothelial factor, a major histocompatibility complex (MHC) molecule, BCMA (CD269, or TNFRSF17), SLAMF7, GPRC5D, FKBP11, KAMP3, ITGA8 and FCRL5.

14. The synthetic T-cell receptor and antigen receptor according to claim 1, wherein the first antigen-binding region contains a heavy chain variable region of an antibody specifically binding to the target antigen, and the second antigen-binding region contains a light chain variable region of the antibody; or the first antigen-binding region contains the light chain variable region of light antibody specifically binding to the target antigen, and the second antigen-binding region contains the heavy chain variable region of the antibody.

15. The synthetic T-cell receptor and antigen receptor according to claim 1, wherein:

the first antigen-binding region comprises an amino acid sequence shown as SEQ ID NO: 22, and the second antigen-binding region comprises an amino acid sequence shown as SEQ ID NO: 23; or the first antigen-binding region comprises an amino acid sequence shown as SEQ ID NO: 23, the second antigen-binding region comprises an amino acid sequence shown as SEQ ID NO: 22, and thus the STAR specifically binds to EGFR; or the first antigen-binding region comprises an amino acid sequence shown as SEQ ID NO: 44, and the second antigen-binding region comprises an amino acid sequence shown as SEQ ID NO: 45; or the first antigen-binding region comprises an amino acid sequence shown as SEQ ID NO: 45, the second antigen-binding region comprises an amino acid sequence shown as SEQ ID NO: 44, and thus the STAR specifically binds to CD19; or the first antigen-binding region comprises an amino acid sequence shown as SEQ ID NO: 46, and the second antigen-binding region comprises an amino acid sequence shown as SEQ ID NO: 47; or the first antigen-binding region comprises an amino acid sequence shown as SEQ ID NO: 47, the second antigen-binding region comprises an amino acid sequence shown as SEQ ID NO: 46, and thus the STAR specifically binds to CD20; or the first antigen-binding region comprises an amino acid sequence shown as SEQ ID NO: 48, and the second antigen-binding region comprises an amino acid sequence shown as SEQ ID NO: 49; or the first antigen-binding region comprises an amino acid sequence shown as SEQ ID NO: 49, the second antigen-binding region comprises an amino acid sequence shown as SEQ ID NO: 48, and thus the STAR specifically binds to CD22; or the first antigen-binding region comprises an amino acid sequence shown as SEQ ID NO: 24, and the second antigen-binding region comprises an amino acid sequence shown as SEQ ID NO: 25; or the first antigen-binding region comprises an amino acid sequence shown as SEQ ID NO: 25, the second antigen-binding region comprises an amino acid sequence shown as SEQ ID NO: 24, and thus the STAR specifically binds to GPC3; or the first antigen-binding region contains a heavy chain variable region of an antibody specifically binding to the CD19, the heavy chain variable region contains a heavy chain CDR1 shown as SEQ ID NO: 28, a heavy chain CDR2 shown as SEQ ID NO: 29 and a heavy chain CDR3 shown as SEQ ID NO: 30, the second antigen-binding region contains a light chain variable region of the antibody specifically binding to the CD19, and the light chain variable region contains a light chain CDR1 shown as SEQ ID NO: 31, a light chain CDR2 shown as SEQ ID NO: 32, and a light chain CDR3 shown as SEQ ID NO: 33; or the first antigen-binding region contains the light chain variable region of an antibody specifically binding to the CD19, the light chain variable region contains the light chain CDR1 shown as SEQ ID NO: 31, the light chain CDR2 shown as SEQ ID NO: 32 and the light chain CDR3 shown as SEQ ID NO: 33, the second antigen-binding region contains the heavy chain variable region of the antibody specifically binding to the CD19, and the heavy chain variable region contains the heavy chain CDR1 shown as SEQ ID NO: 28, the heavy chain CDR2 shown as SEQ ID NO: 29, and the heavy chain CDR3 shown as SEQ ID NO: 30, and thus the STAR specifically binds to CD19; or the first antigen-binding region comprises an amino acid sequence shown as SEQ ID NO: 26, and the second antigen-binding region comprises an amino acid sequence shown as SEQ ID NO: 27; or the first antigen-binding region comprises an amino acid sequence shown as SEQ ID NO: 27, the second antigen-binding region comprises an amino acid sequence shown as SEQ ID NO: 26, and thus the STAR specifically binds to CD19.

16. The synthetic T-cell receptor and antigen receptor according to claim 1, wherein the first antigen-binding region contains a single-chain antibody or a single-domain antibody specifically binding to the target antigen, and/or the second antigen-binding region contains the single-chain antibody or the single-domain antibody specifically binding to the target antigen.

17. The synthetic T-cell receptor and antigen receptor according to claim 16, wherein the first antigen-binding region and the second antigen-binding region bind to a same target antigen.

18. The synthetic T-cell receptor and antigen receptor according to claim 16, wherein the first antigen-binding region and the second antigen-binding region bind to different regions of the same target antigen.

19. The synthetic T-cell receptor and antigen receptor according to claim 16, wherein the first antigen-binding region and the second antigen-binding region bind to different target antigens.

20. A synthetic T-cell receptor and antigen receptor (STAR), containing an α chain and a β chain; the α chain containing a first antigen-binding region and a first constant region, and the β chain containing a second antigen-binding region and a second constant region, wherein the first constant region is as defined in claim 1; and/or wherein the second constant region is as defined in claim 1; and wherein the first antigen-binding region and the second antigen-binding region specifically bind to different target antigens or different regions of a same target antigen.

21. The synthetic T-cell receptor and antigen receptor according to claim 20, wherein the first antigen-binding region and/or the second antigen-binding region contain a single-chain antibody or a single-domain antibody specifically binding to the target antigen.

22. The synthetic T-cell receptor and antigen receptor according to claim 21, wherein:

the single-chain antibody contained in the first antigen-binding region or the second antigen-binding region comprises the amino acid sequence shown as SEQ ID NO: 22 and the amino acid sequence shown as SEQ ID NO: 23, and thus the first antigen-binding region or the second antigen-binding region specifically bind to EGFR; or the single-chain antibody contained in the first antigen-binding region or the second antigen-binding region comprises the amino acid sequence shown as SEQ ID NO: 44 and the amino acid sequence shown as SEQ ID NO: 45, and thus the first antigen-binding region or the second antigen-binding region specifically bind to CD19; or the single-chain antibody contained in the first antigen-binding region or the second antigen-binding region comprises the amino acid sequence shown as SEQ ID NO: 46 and the amino acid sequence shown as SEQ ID NO: 47, and thus the first antigen-binding region or the second antigen-binding region specifically bind to CD20; or the single-chain antibody contained in the first antigen-binding region or the second antigen-binding region comprises the amino acid sequence shown as SEQ ID NO: 48 and the amino acid sequence shown as SEQ ID NO: 49, and thus the first antigen-binding region or the second antigen-binding region specifically bind to CD22; or the single-chain antibody contained in the first antigen-binding region or the second antigen-binding region comprises the amino acid sequence shown as SEQ ID NO: 24 and the amino acid sequence shown as SEQ ID NO: 25, and thus the first antigen-binding region or the second antigen-binding region specifically bind to GPC3; or the single-chain antibody contained in the first antigen-binding region or the second antigen-binding region contains a heavy chain variable region and a light chain variable region, the heavy chain variable region contains the heavy chain CDR1 shown as SEQ ID NO: 28, the heavy chain CDR2 shown as SEQ ID NO: 29 and the heavy chain CDR3 shown as SEQ ID NO: 30, the light chain variable region contains the light chain CDR1 shown as SEQ ID NO: 31, the light chain CDR2 shown as SEQ ID NO: 32 and the light chain CDR3 shown as SEQ ID NO: 33, and thus the first antigen-binding region or the second antigen-binding region specifically bind to CD19; or the single-chain antibody contained in the first antigen-binding region or the second antigen-binding region comprises the amino acid sequence shown as SEQ ID NO: 26 and the amino acid sequence shown as SEQ ID NO: 27, and thus the first antigen-binding region or the second antigen-binding region specifically bind to CD19.

23. The synthetic T-cell receptor and antigen receptor according to claim 21, wherein the two antigen-binding regions bind to CD19 and CD20 respectively, or to CD19 and CD22 respectively, or to CD38 and BCMA respectively, or to PDL1 and EGFR respectively.

24. A therapeutic T cell, comprising the synthetic T-cell receptor and antigen receptor (STAR) according to claim 1.

25. A pharmaceutical composition, comprising the therapeutic T cell according to claim 24 and a pharmaceutical acceptable carrier.

* * * * *

SEQUENCE LISTING

<160> NUMBER OF SEQ ID NOS: 51

<210> SEQ ID NO 1
<211> LENGTH: 141
<212> TYPE: PRT
<213> ORGANISM: Homo sapiens

<400> SEQUENCE: 1

Asp Ile Gln Asn Pro Asp Pro Ala Val Tyr Gln Leu Arg Asp Ser Lys
1 5 10 15

Ser Ser Asp Lys Ser Val Cys Leu Phe Thr Asp Phe Asp Ser Gln Thr
20 25 30

Asn Val Ser Gln Ser Lys Asp Ser Asp Val Tyr Ile Thr Asp Lys Thr
35 40 45

Val Leu Asp Met Arg Ser Met Asp Phe Lys Ser Asn Ser Ala Val Ala
50 55 60

Trp Ser Asn Lys Ser Asp Phe Ala Cys Ala Asn Ala Phe Asn Asn Ser
65 70 75 80

Ile Ile Pro Glu Asp Thr Phe Phe Pro Ser Pro Glu Ser Ser Cys Asp
85 90 95

Val Lys Leu Val Glu Lys Ser Phe Glu Thr Asp Thr Asn Leu Asn Phe
100 105 110

Gln Asn Leu Ser Val Ile Gly Phe Arg Ile Leu Leu Leu Lys Val Ala
115 120 125

Gly Phe Asn Leu Leu Met Thr Leu Arg Leu Trp Ser Ser
130 135 140

<210> SEQ ID NO 2
<211> LENGTH: 137
<212> TYPE: PRT
<213> ORGANISM: Mus musculus

<400> SEQUENCE: 2

Asp Ile Gln Asn Pro Glu Pro Ala Val Tyr Gln Leu Lys Asp Pro Arg
1 5 10 15

Ser Gln Asp Ser Thr Leu Cys Leu Phe Thr Asp Phe Asp Ser Gln Ile
20 25 30

Asn Val Pro Lys Thr Met Glu Ser Gly Thr Phe Ile Thr Asp Lys Thr
35 40 45

Val Leu Asp Met Lys Ala Met Asp Ser Lys Ser Asn Gly Ala Ile Ala
50 55 60

Trp Ser Asn Gln Thr Ser Phe Thr Cys Gln Asp Ile Phe Lys Glu Thr
65 70 75 80

Asn Ala Thr Tyr Pro Ser Ser Asp Val Pro Cys Asp Ala Thr Leu Thr
85 90 95

-continued

```
Glu Lys Ser Phe Glu Thr Asp Met Asn Leu Asn Phe Gln Asn Leu Ser
            100                 105                 110

Val Met Gly Leu Arg Ile Leu Leu Leu Lys Val Ala Gly Phe Asn Leu
        115                 120                 125

Leu Met Thr Leu Arg Leu Trp Ser Ser
    130                 135


<210> SEQ ID NO 3
<211> LENGTH: 18
<212> TYPE: PRT
<213> ORGANISM: Artificial Sequence
<220> FEATURE:
<223> OTHER INFORMATION: Sequence deleted from N terminal in constant
      region of chain of mouse T-cell receptor

<400> SEQUENCE: 3

Asp Ile Gln Asn Pro Glu Pro Ala Val Tyr Gln Leu Lys Asp Pro Arg
1               5                   10                  15

Ser Gln


<210> SEQ ID NO 4
<211> LENGTH: 119
<212> TYPE: PRT
<213> ORGANISM: Artificial Sequence
<220> FEATURE:
<223> OTHER INFORMATION: Constant region of  chain of mouse T-cell
      receptor containing N-terminal modification (Mouse TCRaC-N.DLT)

<400> SEQUENCE: 4

Asp Ser Thr Leu Cys Leu Phe Thr Asp Phe Asp Ser Gln Ile Asn Val
1               5                   10                  15

Pro Lys Thr Met Glu Ser Gly Thr Phe Ile Thr Asp Lys Thr Val Leu
            20                  25                  30

Asp Met Lys Ala Met Asp Ser Lys Ser Asn Gly Ala Ile Ala Trp Ser
        35                  40                  45

Asn Gln Thr Ser Phe Thr Cys Gln Asp Ile Phe Lys Glu Thr Asn Ala
    50                  55                  60

Thr Tyr Pro Ser Ser Asp Val Pro Cys Asp Ala Thr Leu Thr Glu Lys
65                  70                  75                  80

Ser Phe Glu Thr Asp Met Asn Leu Asn Phe Gln Asn Leu Ser Val Met
                85                  90                  95

Gly Leu Arg Ile Leu Leu Leu Lys Val Ala Gly Phe Asn Leu Leu Met
            100                 105                 110

Thr Leu Arg Leu Trp Ser Ser
        115


<210> SEQ ID NO 5
<211> LENGTH: 133
<212> TYPE: PRT
<213> ORGANISM: Artificial Sequence
<220> FEATURE:
<223> OTHER INFORMATION: Constant region of  chain of mouse T-cell
      receptor containing N-terminal modification (Mouse TCRaC-N.Rec-4)

<400> SEQUENCE: 5

Asp Ile Gln Asn Pro Asp Pro Ala Val Tyr Gln Leu Arg Asp Asp Ser
1               5                   10                  15

Thr Leu Cys Leu Phe Thr Asp Phe Asp Ser Gln Ile Asn Val Pro Lys
            20                  25                  30

Thr Met Glu Ser Gly Thr Phe Ile Thr Asp Lys Thr Val Leu Asp Met
        35                  40                  45
```

Lys Ala Met Asp Ser Lys Ser Asn Gly Ala Ile Ala Trp Ser Asn Gln
50 55 60

Thr Ser Phe Thr Cys Gln Asp Ile Phe Lys Glu Thr Asn Ala Thr Tyr
65 70 75 80

Pro Ser Ser Asp Val Pro Cys Asp Ala Thr Leu Thr Glu Lys Ser Phe
85 90 95

Glu Thr Asp Met Asn Leu Asn Phe Gln Asn Leu Ser Val Met Gly Leu
100 105 110

Arg Ile Leu Leu Leu Lys Val Ala Gly Phe Asn Leu Leu Met Thr Leu
115 120 125

Arg Leu Trp Ser Ser
130

<210> SEQ ID NO 6
<211> LENGTH: 141
<212> TYPE: PRT
<213> ORGANISM: Artificial Sequence
<220> FEATURE:
<223> OTHER INFORMATION: Constant region of  chain of human T-cell receptor containing cysteine substitution (Human TCRaC-Cys)

<400> SEQUENCE: 6

Asp Ile Gln Asn Pro Asp Pro Ala Val Tyr Gln Leu Arg Asp Ser Lys
1 5 10 15

Ser Ser Asp Lys Ser Val Cys Leu Phe Thr Asp Phe Asp Ser Gln Thr
20 25 30

Asn Val Ser Gln Ser Lys Asp Ser Asp Val Tyr Ile Thr Asp Lys Cys
35 40 45

Val Leu Asp Met Arg Ser Met Asp Phe Lys Ser Asn Ser Ala Val Ala
50 55 60

Trp Ser Asn Lys Ser Asp Phe Ala Cys Ala Asn Ala Phe Asn Asn Ser
65 70 75 80

Ile Ile Pro Glu Asp Thr Phe Phe Pro Ser Pro Glu Ser Ser Cys Asp
85 90 95

Val Lys Leu Val Glu Lys Ser Phe Glu Thr Asp Thr Asn Leu Asn Phe
100 105 110

Gln Asn Leu Ser Val Ile Gly Phe Arg Ile Leu Leu Leu Lys Val Ala
115 120 125

Gly Phe Asn Leu Leu Met Thr Leu Arg Leu Trp Ser Ser
130 135 140

<210> SEQ ID NO 7
<211> LENGTH: 137
<212> TYPE: PRT
<213> ORGANISM: Artificial Sequence
<220> FEATURE:
<223> OTHER INFORMATION: Constant region of  chain of mouse T-cell receptor containing cysteine substitution (Mouse TCRaC-Cys)

<400> SEQUENCE: 7

Asp Ile Gln Asn Pro Glu Pro Ala Val Tyr Gln Leu Lys Asp Pro Arg
1 5 10 15

Ser Gln Asp Ser Thr Leu Cys Leu Phe Thr Asp Phe Asp Ser Gln Ile
20 25 30

Asn Val Pro Lys Thr Met Glu Ser Gly Thr Phe Ile Thr Asp Lys Cys
35 40 45

Val Leu Asp Met Lys Ala Met Asp Ser Lys Ser Asn Gly Ala Ile Ala
50 55 60

Trp Ser Asn Gln Thr Ser Phe Thr Cys Gln Asp Ile Phe Lys Glu Thr
65 70 75 80

Asn Ala Thr Tyr Pro Ser Ser Asp Val Pro Cys Asp Ala Thr Leu Thr
85 90 95

Glu Lys Ser Phe Glu Thr Asp Met Asn Leu Asn Phe Gln Asn Leu Ser
100 105 110

Val Met Gly Leu Arg Ile Leu Leu Leu Lys Val Ala Gly Phe Asn Leu
115 120 125

Leu Met Thr Leu Arg Leu Trp Ser Ser
130 135

<210> SEQ ID NO 8
<211> LENGTH: 9
<212> TYPE: PRT
<213> ORGANISM: Artificial Sequence
<220> FEATURE:
<223> OTHER INFORMATION: Transmembrane region of constant region of chain of mouse T-cell receptor containing hydrophobic amino acid substitution

<400> SEQUENCE: 8

Leu Leu Val Ile Val Leu Arg Ile Leu
1 5

<210> SEQ ID NO 9
<211> LENGTH: 137
<212> TYPE: PRT
<213> ORGANISM: Artificial Sequence
<220> FEATURE:
<223> OTHER INFORMATION: Constant region of  chain of mouse T-cell receptor containing a hydrophobic amino acid substitution (Mouse TCRaC-TM9)

<400> SEQUENCE: 9

Asp Ile Gln Asn Pro Glu Pro Ala Val Tyr Gln Leu Lys Asp Pro Arg
1 5 10 15

Ser Gln Asp Ser Thr Leu Cys Leu Phe Thr Asp Phe Asp Ser Gln Ile
20 25 30

Asn Val Pro Lys Thr Met Glu Ser Gly Thr Phe Ile Thr Asp Lys Thr
35 40 45

Val Leu Asp Met Lys Ala Met Asp Ser Lys Ser Asn Gly Ala Ile Ala
50 55 60

Trp Ser Asn Gln Thr Ser Phe Thr Cys Gln Asp Ile Phe Lys Glu Thr
65 70 75 80

Asn Ala Thr Tyr Pro Ser Ser Asp Val Pro Cys Asp Ala Thr Leu Thr
85 90 95

Glu Lys Ser Phe Glu Thr Asp Met Asn Leu Asn Phe Gln Asn Leu Leu
100 105 110

Val Ile Val Leu Arg Ile Leu Leu Leu Lys Val Ala Gly Phe Asn Leu
115 120 125

Leu Met Thr Leu Arg Leu Trp Ser Ser
130 135

<210> SEQ ID NO 10
<211> LENGTH: 137
<212> TYPE: PRT
<213> ORGANISM: Artificial Sequence
<220> FEATURE:
<223> OTHER INFORMATION: Mouse TCRaC-Cys- M9

<400> SEQUENCE: 10

```
Asp Ile Gln Asn Pro Glu Pro Ala Val Tyr Gln Leu Lys Asp Pro Arg
1               5                   10                  15

Ser Gln Asp Ser Thr Leu Cys Leu Phe Thr Asp Phe Asp Ser Gln Ile
            20                  25                  30

Asn Val Pro Lys Thr Met Glu Ser Gly Thr Phe Ile Thr Asp Lys Cys
        35                  40                  45

Val Leu Asp Met Lys Ala Met Asp Ser Lys Ser Asn Gly Ala Ile Ala
    50                  55                  60

Trp Ser Asn Gln Thr Ser Phe Thr Cys Gln Asp Ile Phe Lys Glu Thr
65                  70                  75                  80

Asn Ala Thr Tyr Pro Ser Ser Asp Val Pro Cys Asp Ala Thr Leu Thr
                85                  90                  95

Glu Lys Ser Phe Glu Thr Asp Met Asn Leu Asn Phe Gln Asn Leu Leu
            100                 105                 110

Val Ile Val Leu Arg Ile Leu Leu Leu Lys Val Ala Gly Phe Asn Leu
        115                 120                 125

Leu Met Thr Leu Arg Leu Trp Ser Ser
    130                 135


<210> SEQ ID NO 11
<211> LENGTH: 133
<212> TYPE: PRT
<213> ORGANISM: Artificial Sequence
<220> FEATURE:
<223> OTHER INFORMATION: Mouse TCRaC-Cys-N.Rec-1

<400> SEQUENCE: 11

Pro Asp Pro Ala Val Tyr Gln Leu Arg Asp Ser Lys Ser Ser Asp Ser
1               5                   10                  15

Thr Leu Cys Leu Phe Thr Asp Phe Asp Ser Gln Ile Asn Val Pro Lys
            20                  25                  30

Thr Met Glu Ser Gly Thr Phe Ile Thr Asp Lys Cys Val Leu Asp Met
        35                  40                  45

Lys Ala Met Asp Ser Lys Ser Asn Gly Ala Ile Ala Trp Ser Asn Gln
    50                  55                  60

Thr Ser Phe Thr Cys Gln Asp Ile Phe Lys Glu Thr Asn Ala Thr Tyr
65                  70                  75                  80

Pro Ser Ser Asp Val Pro Cys Asp Ala Thr Leu Thr Glu Lys Ser Phe
                85                  90                  95

Glu Thr Asp Met Asn Leu Asn Phe Gln Asn Leu Ser Val Met Gly Leu
            100                 105                 110

Arg Ile Leu Leu Leu Lys Val Ala Gly Phe Asn Leu Leu Met Thr Leu
        115                 120                 125

Arg Leu Trp Ser Ser
    130


<210> SEQ ID NO 12
<211> LENGTH: 133
<212> TYPE: PRT
<213> ORGANISM: Artificial Sequence
<220> FEATURE:
<223> OTHER INFORMATION: Mouse TCRaC-Cys-N.Rec-1

<400> SEQUENCE: 12

Pro Asp Pro Ala Val Tyr Gln Leu Arg Asp Ser Lys Ser Ser Asp Ser
1               5                   10                  15

Thr Leu Cys Leu Phe Thr Asp Phe Asp Ser Gln Ile Asn Val Pro Lys
```

```
            20                  25                  30

Thr Met Glu Ser Gly Thr Phe Ile Thr Asp Lys Thr Val Leu Asp Met
        35                  40                  45

Lys Ala Met Asp Ser Lys Ser Asn Gly Ala Ile Ala Trp Ser Asn Gln
    50                  55                  60

Thr Ser Phe Thr Cys Gln Asp Ile Phe Lys Glu Thr Asn Ala Thr Tyr
65                  70                  75                  80

Pro Ser Ser Asp Val Pro Cys Asp Ala Thr Leu Thr Glu Lys Ser Phe
                85                  90                  95

Glu Thr Asp Met Asn Leu Asn Phe Gln Asn Leu Leu Val Ile Val Leu
            100                 105                 110

Arg Ile Leu Leu Leu Lys Val Ala Gly Phe Asn Leu Leu Met Thr Leu
        115                 120                 125

Arg Leu Trp Ser Ser
    130


<210> SEQ ID NO 13
<211> LENGTH: 133
<212> TYPE: PRT
<213> ORGANISM: Artificial Sequence
<220> FEATURE:
<223> OTHER INFORMATION: Mouse TCRaC-Cys-TM9-N.Rec-1

<400> SEQUENCE: 13

Pro Asp Pro Ala Val Tyr Gln Leu Arg Asp Ser Lys Ser Ser Asp Ser
1               5                   10                  15

Thr Leu Cys Leu Phe Thr Asp Phe Asp Ser Gln Ile Asn Val Pro Lys
            20                  25                  30

Thr Met Glu Ser Gly Thr Phe Ile Thr Asp Lys Cys Val Leu Asp Met
        35                  40                  45

Lys Ala Met Asp Ser Lys Ser Asn Gly Ala Ile Ala Trp Ser Asn Gln
    50                  55                  60

Thr Ser Phe Thr Cys Gln Asp Ile Phe Lys Glu Thr Asn Ala Thr Tyr
65                  70                  75                  80

Pro Ser Ser Asp Val Pro Cys Asp Ala Thr Leu Thr Glu Lys Ser Phe
                85                  90                  95

Glu Thr Asp Met Asn Leu Asn Phe Gln Asn Leu Leu Val Ile Val Leu
            100                 105                 110

Arg Ile Leu Leu Leu Lys Val Ala Gly Phe Asn Leu Leu Met Thr Leu
        115                 120                 125

Arg Leu Trp Ser Ser
    130


<210> SEQ ID NO 14
<211> LENGTH: 176
<212> TYPE: PRT
<213> ORGANISM: Homo sapiens

<400> SEQUENCE: 14

Asp Leu Lys Asn Val Phe Pro Pro Glu Val Ala Val Phe Glu Pro Ser
1               5                   10                  15

Glu Ala Glu Ile Ser His Thr Gln Lys Ala Thr Leu Val Cys Leu Ala
            20                  25                  30

Thr Gly Phe Phe Pro Asp His Val Glu Leu Ser Trp Trp Val Asn Gly
        35                  40                  45

Lys Glu Val His Ser Gly Val Ser Thr Asp Pro Gln Pro Leu Lys Glu
    50                  55                  60
```

Gln Pro Ala Leu Asn Asp Ser Arg Tyr Cys Leu Ser Ser Arg Leu Arg
65 70 75 80

Val Ser Ala Thr Phe Trp Gln Asn Pro Arg Asn His Phe Arg Cys Gln
85 90 95

Val Gln Phe Tyr Gly Leu Ser Glu Asn Asp Glu Trp Thr Gln Asp Arg
100 105 110

Ala Lys Pro Val Thr Gln Ile Val Ser Ala Glu Ala Trp Gly Arg Ala
115 120 125

Asp Cys Gly Phe Thr Ser Val Ser Tyr Gln Gln Gly Val Leu Ser Ala
130 135 140

Thr Ile Leu Tyr Glu Ile Leu Leu Gly Lys Ala Thr Leu Tyr Ala Val
145 150 155 160

Leu Val Ser Ala Leu Val Leu Met Ala Met Val Lys Arg Lys Asp Phe
165 170 175

<210> SEQ ID NO 15
<211> LENGTH: 172
<212> TYPE: PRT
<213> ORGANISM: Mus musculus

<400> SEQUENCE: 15

Asp Leu Arg Asn Val Thr Pro Pro Lys Val Ser Leu Phe Glu Pro Ser
1 5 10 15

Lys Ala Glu Ile Ala Asn Lys Gln Lys Ala Thr Leu Val Cys Leu Ala
20 25 30

Arg Gly Phe Phe Pro Asp His Val Glu Leu Ser Trp Trp Val Asn Gly
35 40 45

Lys Glu Val His Ser Gly Val Ser Thr Asp Pro Gln Ala Tyr Lys Glu
50 55 60

Ser Asn Tyr Ser Tyr Cys Leu Ser Ser Arg Leu Arg Val Ser Ala Thr
65 70 75 80

Phe Trp His Asn Pro Arg Asn His Phe Arg Cys Gln Val Gln Phe His
85 90 95

Gly Leu Ser Glu Glu Asp Lys Trp Pro Glu Gly Ser Pro Lys Pro Val
100 105 110

Thr Gln Asn Ile Ser Ala Glu Ala Trp Gly Arg Ala Asp Cys Gly Ile
115 120 125

Thr Ser Ala Ser Tyr Gln Gln Gly Val Leu Ser Ala Thr Ile Leu Tyr
130 135 140

Glu Ile Leu Leu Gly Lys Ala Thr Leu Tyr Ala Val Leu Val Ser Thr
145 150 155 160

Leu Val Val Met Ala Met Val Lys Arg Lys Asn Ser
165 170

<210> SEQ ID NO 16
<211> LENGTH: 25
<212> TYPE: PRT
<213> ORGANISM: Artificial Sequence
<220> FEATURE:
<223> OTHER INFORMATION: Sequence deleted from N terminal in constant region of chain of mouse T-cell receptor

<400> SEQUENCE: 16

Asp Leu Arg Asn Val Thr Pro Pro Lys Val Ser Leu Phe Glu Pro Ser
1 5 10 15

Lys Ala Glu Ile Ala Asn Lys Gln Lys
20 25

<210> SEQ ID NO 17
<211> LENGTH: 147
<212> TYPE: PRT
<213> ORGANISM: Artificial Sequence
<220> FEATURE:
<223> OTHER INFORMATION: Constant region of chain of mouse T-cell
      receptor containing N-terminal deletion (Mouse TCRbC-N.DLT)

<400> SEQUENCE: 17

```
Ala Thr Leu Val Cys Leu Ala Arg Gly Phe Phe Pro Asp His Val Glu
1               5                   10                  15

Leu Ser Trp Trp Val Asn Gly Lys Glu Val His Ser Gly Val Ser Thr
            20                  25                  30

Asp Pro Gln Ala Tyr Lys Glu Ser Asn Tyr Ser Tyr Cys Leu Ser Ser
        35                  40                  45

Arg Leu Arg Val Ser Ala Thr Phe Trp His Asn Pro Arg Asn His Phe
    50                  55                  60

Arg Cys Gln Val Gln Phe His Gly Leu Ser Glu Glu Asp Lys Trp Pro
65                  70                  75                  80

Glu Gly Ser Pro Lys Pro Val Thr Gln Asn Ile Ser Ala Glu Ala Trp
                85                  90                  95

Gly Arg Ala Asp Cys Gly Ile Thr Ser Ala Ser Tyr Gln Gln Gly Val
            100                 105                 110

Leu Ser Ala Thr Ile Leu Tyr Glu Ile Leu Leu Gly Lys Ala Thr Leu
        115                 120                 125

Tyr Ala Val Leu Val Ser Thr Leu Val Val Met Ala Met Val Lys Arg
    130                 135                 140

Lys Asn Ser
145
```

<210> SEQ ID NO 18
<211> LENGTH: 166
<212> TYPE: PRT
<213> ORGANISM: Artificial Sequence
<220> FEATURE:
<223> OTHER INFORMATION: Constant region of  chain of mouse T-cell
      receptor containing N-terminal modification (Mouse TCRbC-N.-Rec-4)

<400> SEQUENCE: 18

```
Asp Leu Lys Asn Val Phe Pro Pro Glu Val Ala Val Phe Glu Pro Ser
1               5                   10                  15

Ala Glu Ile Ala Thr Leu Val Cys Leu Ala Arg Gly Phe Phe Pro Asp
            20                  25                  30

His Val Glu Leu Ser Trp Trp Val Asn Gly Lys Glu Val His Ser Gly
        35                  40                  45

Val Ser Thr Asp Pro Gln Ala Tyr Lys Glu Ser Asn Tyr Ser Tyr Cys
    50                  55                  60

Leu Ser Ser Arg Leu Arg Val Ser Ala Thr Phe Trp His Asn Pro Arg
65                  70                  75                  80

Asn His Phe Arg Cys Gln Val Gln Phe His Gly Leu Ser Glu Glu Asp
                85                  90                  95

Lys Trp Pro Glu Gly Ser Pro Lys Pro Val Thr Gln Asn Ile Ser Ala
            100                 105                 110

Glu Ala Trp Gly Arg Ala Asp Cys Gly Ile Thr Ser Ala Ser Tyr Gln
        115                 120                 125

Gln Gly Val Leu Ser Ala Thr Ile Leu Tyr Glu Ile Leu Leu Gly Lys
    130                 135                 140
```

Ala Thr Leu Tyr Ala Val Leu Val Ser Thr Leu Val Val Met Ala Met
145 150 155 160

Val Lys Arg Lys Asn Ser
165

<210> SEQ ID NO 19
<211> LENGTH: 176
<212> TYPE: PRT
<213> ORGANISM: Artificial Sequence
<220> FEATURE:
<223> OTHER INFORMATION: Constant region of  chain of human T-cell
receptor containing cysteine substitution (Human TCRbC-Cys)

<400> SEQUENCE: 19

Asp Leu Lys Asn Val Phe Pro Pro Glu Val Ala Val Phe Glu Pro Ser
1 5 10 15

Glu Ala Glu Ile Ser His Thr Gln Lys Ala Thr Leu Val Cys Leu Ala
20 25 30

Thr Gly Phe Phe Pro Asp His Val Glu Leu Ser Trp Trp Val Asn Gly
35 40 45

Lys Glu Val His Ser Gly Val Cys Thr Asp Pro Gln Pro Leu Lys Glu
50 55 60

Gln Pro Ala Leu Asn Asp Ser Arg Tyr Cys Leu Ser Ser Arg Leu Arg
65 70 75 80

Val Ser Ala Thr Phe Trp Gln Asn Pro Arg Asn His Phe Arg Cys Gln
85 90 95

Val Gln Phe Tyr Gly Leu Ser Glu Asn Asp Glu Trp Thr Gln Asp Arg
100 105 110

Ala Lys Pro Val Thr Gln Ile Val Ser Ala Glu Ala Trp Gly Arg Ala
115 120 125

Asp Cys Gly Phe Thr Ser Val Ser Tyr Gln Gln Gly Val Leu Ser Ala
130 135 140

Thr Ile Leu Tyr Glu Ile Leu Leu Gly Lys Ala Thr Leu Tyr Ala Val
145 150 155 160

Leu Val Ser Ala Leu Val Leu Met Ala Met Val Lys Arg Lys Asp Phe
165 170 175

<210> SEQ ID NO 20
<211> LENGTH: 172
<212> TYPE: PRT
<213> ORGANISM: Artificial Sequence
<220> FEATURE:
<223> OTHER INFORMATION: Constant region of  chain of mouse T-cell
receptor containing cysteine substitution (Mouse TCRbC-Cys)

<400> SEQUENCE: 20

Asp Leu Arg Asn Val Thr Pro Pro Lys Val Ser Leu Phe Glu Pro Ser
1 5 10 15

Lys Ala Glu Ile Ala Asn Lys Gln Lys Ala Thr Leu Val Cys Leu Ala
20 25 30

Arg Gly Phe Phe Pro Asp His Val Glu Leu Ser Trp Trp Val Asn Gly
35 40 45

Lys Glu Val His Ser Gly Val Cys Thr Asp Pro Gln Ala Tyr Lys Glu
50 55 60

Ser Asn Tyr Ser Tyr Cys Leu Ser Ser Arg Leu Arg Val Ser Ala Thr
65 70 75 80

Phe Trp His Asn Pro Arg Asn His Phe Arg Cys Gln Val Gln Phe His
85 90 95

Gly Leu Ser Glu Glu Asp Lys Trp Pro Glu Gly Ser Pro Lys Pro Val
100 105 110

Thr Gln Asn Ile Ser Ala Glu Ala Trp Gly Arg Ala Asp Cys Gly Ile
115 120 125

Thr Ser Ala Ser Tyr Gln Gln Gly Val Leu Ser Ala Thr Ile Leu Tyr
130 135 140

Glu Ile Leu Leu Gly Lys Ala Thr Leu Tyr Ala Val Leu Val Ser Thr
145 150 155 160

Leu Val Val Met Ala Met Val Lys Arg Lys Asn Ser
165 170

<210> SEQ ID NO 21
<211> LENGTH: 166
<212> TYPE: PRT
<213> ORGANISM: Artificial Sequence
<220> FEATURE:
<223> OTHER INFORMATION: Constant region of  chain of mouse T-cell receptor containing N-terminal modification and cysteine substitution (Mouse TCRbC-Cys-N.Rec-1)

<400> SEQUENCE: 21

Pro Pro Glu Val Ala Val Phe Glu Pro Ser Glu Ala Glu Ile Ser His
1 5 10 15

Thr Gln Lys Ala Thr Leu Val Cys Leu Ala Arg Gly Phe Phe Pro Asp
20 25 30

His Val Glu Leu Ser Trp Trp Val Asn Gly Lys Glu Val His Ser Gly
35 40 45

Val Cys Thr Asp Pro Gln Ala Tyr Lys Glu Ser Asn Tyr Ser Tyr Cys
50 55 60

Leu Ser Ser Arg Leu Arg Val Ser Ala Thr Phe Trp His Asn Pro Arg
65 70 75 80

Asn His Phe Arg Cys Gln Val Gln Phe His Gly Leu Ser Glu Glu Asp
85 90 95

Lys Trp Pro Glu Gly Ser Pro Lys Pro Val Thr Gln Asn Ile Ser Ala
100 105 110

Glu Ala Trp Gly Arg Ala Asp Cys Gly Ile Thr Ser Ala Ser Tyr Gln
115 120 125

Gln Gly Val Leu Ser Ala Thr Ile Leu Tyr Glu Ile Leu Leu Gly Lys
130 135 140

Ala Thr Leu Tyr Ala Val Leu Val Ser Thr Leu Val Val Met Ala Met
145 150 155 160

Val Lys Arg Lys Asn Ser
165

<210> SEQ ID NO 22
<211> LENGTH: 124
<212> TYPE: PRT
<213> ORGANISM: Artificial Sequence
<220> FEATURE:
<223> OTHER INFORMATION: anti-EGFR Cetux-VH

<400> SEQUENCE: 22

Gln Val Gln Leu Lys Gln Ser Gly Pro Gly Leu Val Gln Pro Ser Gln
1 5 10 15

Ser Leu Ser Ile Thr Cys Thr Val Ser Gly Phe Ser Leu Thr Asn Tyr
20 25 30

Gly Val His Trp Val Arg Gln Ser Pro Gly Lys Gly Leu Glu Trp Leu
35 40 45

```
Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly
        115                 120


<210> SEQ ID NO 23
<211> LENGTH: 111
<212> TYPE: PRT
<213> ORGANISM: Artificial Sequence
<220> FEATURE:
<223> OTHER INFORMATION: Anti-EGFR Cetux-VL

<400> SEQUENCE: 23

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala
            100                 105                 110


<210> SEQ ID NO 24
<211> LENGTH: 113
<212> TYPE: PRT
<213> ORGANISM: Artificial Sequence
<220> FEATURE:
<223> OTHER INFORMATION: Anti-GPC3 GC33 VL

<400> SEQUENCE: 24

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Arg Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

Arg
```

<210> SEQ ID NO 25
<211> LENGTH: 115
<212> TYPE: PRT
<213> ORGANISM: Artificial Sequence
<220> FEATURE:
<223> OTHER INFORMATION: Anti-GPC3 GC33 VH

<400> SEQUENCE: 25

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asp Tyr
20 25 30

Glu Met His Trp Val Arg Gln Ala Pro Gly Gln Gly Leu Glu Trp Met
35 40 45

Gly Ala Leu Asp Pro Lys Thr Gly Asp Thr Ala Tyr Ser Gln Lys Phe
50 55 60

Lys Gly Arg Val Thr Leu Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Thr Arg Phe Tyr Ser Tyr Thr Tyr Trp Gly Gln Gly Thr Leu Val Thr
100 105 110

Val Ser Ser
115

<210> SEQ ID NO 26
<211> LENGTH: 113
<212> TYPE: PRT
<213> ORGANISM: Artificial Sequence
<220> FEATURE:
<223> OTHER INFORMATION: Anti-CD19 334 VH

<400> SEQUENCE: 26

Gln Val Gln Leu Gln Gln Ser Gly Ala Glu Leu Val Arg Pro Gly Ala
1 5 10 15

Ser Val Lys Leu Ser Cys Lys Ala Leu Gly Phe Ile Phe Thr Asp Tyr
20 25 30

Glu Ile His Trp Val Lys Gln Thr Pro Val His Gly Leu Glu Trp Ile
35 40 45

Gly Ala Phe His Pro Gly Ser Gly Gly Ser Ala Tyr Asn Gln Lys Phe
50 55 60

Lys Gly Lys Ala Thr Leu Thr Ala Asp Lys Ser Ser Ser Thr Ala Tyr
65 70 75 80

Met Glu Leu Ser Ser Leu Thr Phe Glu Asp Ser Ala Val Tyr His Cys
85 90 95

Thr Arg Gln Leu Gly Pro Asp Trp Gly Gln Gly Thr Leu Val Thr Val
100 105 110

Ser

<210> SEQ ID NO 27
<211> LENGTH: 112
<212> TYPE: PRT
<213> ORGANISM: Artificial Sequence
<220> FEATURE:
<223> OTHER INFORMATION: Anti-CD19 334 VL

<400> SEQUENCE: 27

Asp Val Val Met Thr Gln Thr Pro Leu Thr Leu Ser Val Thr Ile Gly

```
1               5                   10                  15

Gln Pro Ala Ser Ile Ser Cys Lys Ser Ser Gln Ser Leu Leu Glu Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Arg Ile
65                  70                  75                  80

Ser Arg Val Glu Ala Glu Asp Leu Gly Val Tyr Tyr Cys Trp Gln Gly
                85                  90                  95

Thr Gln Phe Pro Trp Thr Phe Gly Gly Gly Thr Lys Leu Glu Ile Lys
            100                 105                 110


<210> SEQ ID NO 28
<211> LENGTH: 8
<212> TYPE: PRT
<213> ORGANISM: Artificial Sequence
<220> FEATURE:
<223> OTHER INFORMATION: Anti-CD19 334 heavy chain CDR1

<400> SEQUENCE: 28

Gly Phe Ile Phe Thr Asp Tyr Glu
1               5


<210> SEQ ID NO 29
<211> LENGTH: 8
<212> TYPE: PRT
<213> ORGANISM: Artificial Sequence
<220> FEATURE:
<223> OTHER INFORMATION: Anti-CD19 334 heavy chain CDR2

<400> SEQUENCE: 29

Phe His Pro Gly Ser Gly Gly Ser
1               5


<210> SEQ ID NO 30
<211> LENGTH: 7
<212> TYPE: PRT
<213> ORGANISM: Artificial Sequence
<220> FEATURE:
<223> OTHER INFORMATION: Anti-CD19 334 heavy chain CDR3

<400> SEQUENCE: 30

Thr Arg Gln Leu Gly Pro Asp
1               5


<210> SEQ ID NO 31
<211> LENGTH: 11
<212> TYPE: PRT
<213> ORGANISM: Artificial Sequence
<220> FEATURE:
<223> OTHER INFORMATION: Anti-CD19 334 light chain CDR1

<400> SEQUENCE: 31

Gln Ser Leu Leu Glu Ser Asp Gly Lys Thr Tyr
1               5                   10


<210> SEQ ID NO 32
<211> LENGTH: 3
<212> TYPE: PRT
<213> ORGANISM: Artificial Sequence
<220> FEATURE:
<223> OTHER INFORMATION: Anti-CD19 334 light chain CDR2
```

<400> SEQUENCE: 32

Leu Val Ser
1

<210> SEQ ID NO 33
<211> LENGTH: 9
<212> TYPE: PRT
<213> ORGANISM: Artificial Sequence
<220> FEATURE:
<223> OTHER INFORMATION: Anti-CD19 334 light chain CDR3

<400> SEQUENCE: 33

Trp Gln Gly Thr Gln Phe Pro Trp Thr
1 5

<210> SEQ ID NO 34
<211> LENGTH: 133
<212> TYPE: PRT
<213> ORGANISM: Artificial Sequence
<220> FEATURE:
<223> OTHER INFORMATION: TCRaC-N.Rec-1

<400> SEQUENCE: 34

Pro Asp Pro Ala Val Tyr Gln Leu Arg Asp Ser Lys Ser Ser Asp Ser
1 5 10 15

Thr Leu Cys Leu Phe Thr Asp Phe Asp Ser Gln Ile Asn Val Pro Lys
20 25 30

Thr Met Glu Ser Gly Thr Phe Ile Thr Asp Lys Thr Val Leu Asp Met
35 40 45

Lys Ala Met Asp Ser Lys Ser Asn Gly Ala Ile Ala Trp Ser Asn Gln
50 55 60

Thr Ser Phe Thr Cys Gln Asp Ile Phe Lys Glu Thr Asn Ala Thr Tyr
65 70 75 80

Pro Ser Ser Asp Val Pro Cys Asp Ala Thr Leu Thr Glu Lys Ser Phe
85 90 95

Glu Thr Asp Met Asn Leu Asn Phe Gln Asn Leu Ser Val Met Gly Leu
100 105 110

Arg Ile Leu Leu Leu Lys Val Ala Gly Phe Asn Leu Leu Met Thr Leu
115 120 125

Arg Leu Trp Ser Ser
130

<210> SEQ ID NO 35
<211> LENGTH: 129
<212> TYPE: PRT
<213> ORGANISM: Artificial Sequence
<220> FEATURE:
<223> OTHER INFORMATION: TCRaC-N.Rec-2

<400> SEQUENCE: 35

Val Tyr Gln Leu Arg Asp Ser Lys Ser Ser Asp Ser Thr Leu Cys Leu
1 5 10 15

Phe Thr Asp Phe Asp Ser Gln Ile Asn Val Pro Lys Thr Met Glu Ser
20 25 30

Gly Thr Phe Ile Thr Asp Lys Thr Val Leu Asp Met Lys Ala Met Asp
35 40 45

Ser Lys Ser Asn Gly Ala Ile Ala Trp Ser Asn Gln Thr Ser Phe Thr
50 55 60

Cys Gln Asp Ile Phe Lys Glu Thr Asn Ala Thr Tyr Pro Ser Ser Asp

```
65                  70                  75                  80

Val Pro Cys Asp Ala Thr Leu Thr Glu Lys Ser Phe Glu Thr Asp Met
                85                  90                  95

Asn Leu Asn Phe Gln Asn Leu Ser Val Met Gly Leu Arg Ile Leu Leu
            100                 105                 110

Leu Lys Val Ala Gly Phe Asn Leu Leu Met Thr Leu Arg Leu Trp Ser
        115                 120                 125

Ser


<210> SEQ ID NO 36
<211> LENGTH: 125
<212> TYPE: PRT
<213> ORGANISM: Artificial Sequence
<220> FEATURE:
<223> OTHER INFORMATION: TCRaC-N.Rec-3

<400> SEQUENCE: 36

Arg Asp Ser Lys Ser Ser Asp Ser Thr Leu Cys Leu Phe Thr Asp Phe
1               5                   10                  15

Asp Ser Gln Ile Asn Val Pro Lys Thr Met Glu Ser Gly Thr Phe Ile
            20                  25                  30

Thr Asp Lys Thr Val Leu Asp Met Lys Ala Met Asp Ser Lys Ser Asn
        35                  40                  45

Gly Ala Ile Ala Trp Ser Asn Gln Thr Ser Phe Thr Cys Gln Asp Ile
    50                  55                  60

Phe Lys Glu Thr Asn Ala Thr Tyr Pro Ser Ser Asp Val Pro Cys Asp
65                  70                  75                  80

Ala Thr Leu Thr Glu Lys Ser Phe Glu Thr Asp Met Asn Leu Asn Phe
                85                  90                  95

Gln Asn Leu Ser Val Met Gly Leu Arg Ile Leu Leu Leu Lys Val Ala
            100                 105                 110

Gly Phe Asn Leu Leu Met Thr Leu Arg Leu Trp Ser Ser
        115                 120                 125


<210> SEQ ID NO 37
<211> LENGTH: 166
<212> TYPE: PRT
<213> ORGANISM: Artificial Sequence
<220> FEATURE:
<223> OTHER INFORMATION: TCRbC-N.Rec-1

<400> SEQUENCE: 37

Pro Pro Glu Val Ala Val Phe Glu Pro Ser Glu Ala Glu Ile Ser His
1               5                   10                  15

Thr Gln Lys Ala Thr Leu Val Cys Leu Ala Arg Gly Phe Phe Pro Asp
            20                  25                  30

His Val Glu Leu Ser Trp Trp Val Asn Gly Lys Glu Val His Ser Gly
        35                  40                  45

Val Ser Thr Asp Pro Gln Ala Tyr Lys Glu Ser Asn Tyr Ser Tyr Cys
    50                  55                  60

Leu Ser Ser Arg Leu Arg Val Ser Ala Thr Phe Trp His Asn Pro Arg
65                  70                  75                  80

Asn His Phe Arg Cys Gln Val Gln Phe His Gly Leu Ser Glu Glu Asp
                85                  90                  95

Lys Trp Pro Glu Gly Ser Pro Lys Pro Val Thr Gln Asn Ile Ser Ala
            100                 105                 110

Glu Ala Trp Gly Arg Ala Asp Cys Gly Ile Thr Ser Ala Ser Tyr Gln
```

```
        115                 120                 125

Gln Gly Val Leu Ser Ala Thr Ile Leu Tyr Glu Ile Leu Leu Gly Lys
    130                 135                 140

Ala Thr Leu Tyr Ala Val Leu Val Ser Thr Leu Val Val Met Ala Met
145                 150                 155                 160

Val Lys Arg Lys Asn Ser
                165


<210> SEQ ID NO 38
<211> LENGTH: 160
<212> TYPE: PRT
<213> ORGANISM: Artificial Sequence
<220> FEATURE:
<223> OTHER INFORMATION: TCRbC-N.Rec-2

<400> SEQUENCE: 38

Phe Glu Pro Ser Glu Ala Glu Ile Ser His Thr Gln Lys Ala Thr Leu
1               5                   10                  15

Val Cys Leu Ala Arg Gly Phe Phe Pro Asp His Val Glu Leu Ser Trp
            20                  25                  30

Trp Val Asn Gly Lys Glu Val His Ser Gly Val Ser Thr Asp Pro Gln
        35                  40                  45

Ala Tyr Lys Glu Ser Asn Tyr Ser Tyr Cys Leu Ser Ser Arg Leu Arg
    50                  55                  60

Val Ser Ala Thr Phe Trp His Asn Pro Arg Asn His Phe Arg Cys Gln
65                  70                  75                  80

Val Gln Phe His Gly Leu Ser Glu Glu Asp Lys Trp Pro Glu Gly Ser
                85                  90                  95

Pro Lys Pro Val Thr Gln Asn Ile Ser Ala Glu Ala Trp Gly Arg Ala
            100                 105                 110

Asp Cys Gly Ile Thr Ser Ala Ser Tyr Gln Gln Gly Val Leu Ser Ala
        115                 120                 125

Thr Ile Leu Tyr Glu Ile Leu Leu Gly Lys Ala Thr Leu Tyr Ala Val
    130                 135                 140

Leu Val Ser Thr Leu Val Val Met Ala Met Val Lys Arg Lys Asn Ser
145                 150                 155                 160


<210> SEQ ID NO 39
<211> LENGTH: 154
<212> TYPE: PRT
<213> ORGANISM: Artificial Sequence
<220> FEATURE:
<223> OTHER INFORMATION: TCRbC-N.Rec-3

<400> SEQUENCE: 39

Glu Ile Ser His Thr Gln Lys Ala Thr Leu Val Cys Leu Ala Arg Gly
1               5                   10                  15

Phe Phe Pro Asp His Val Glu Leu Ser Trp Trp Val Asn Gly Lys Glu
            20                  25                  30

Val His Ser Gly Val Ser Thr Asp Pro Gln Ala Tyr Lys Glu Ser Asn
        35                  40                  45

Tyr Ser Tyr Cys Leu Ser Ser Arg Leu Arg Val Ser Ala Thr Phe Trp
    50                  55                  60

His Asn Pro Arg Asn His Phe Arg Cys Gln Val Gln Phe His Gly Leu
65                  70                  75                  80

Ser Glu Glu Asp Lys Trp Pro Glu Gly Ser Pro Lys Pro Val Thr Gln
                85                  90                  95
```

```
Asn Ile Ser Ala Glu Ala Trp Gly Arg Ala Asp Cys Gly Ile Thr Ser
            100                 105                 110

Ala Ser Tyr Gln Gln Gly Val Leu Ser Ala Thr Ile Leu Tyr Glu Ile
        115                 120                 125

Leu Leu Gly Lys Ala Thr Leu Tyr Ala Val Leu Val Ser Thr Leu Val
    130                 135                 140

Val Met Ala Met Val Lys Arg Lys Asn Ser
145                 150


<210> SEQ ID NO 40
<211> LENGTH: 137
<212> TYPE: PRT
<213> ORGANISM: Artificial Sequence
<220> FEATURE:
<223> OTHER INFORMATION: mouse TCRaC-N.rRec with random rearrangement of
      18 amino acids at N terminal

<400> SEQUENCE: 40

Asn Gln Ser Val Asp Pro Asp Glu Gln Leu Ile Pro Tyr Arg Lys Ala
1               5                   10                  15

Gln Pro Asp Ser Thr Leu Cys Leu Phe Thr Asp Phe Asp Ser Gln Ile
            20                  25                  30

Asn Val Pro Lys Thr Met Glu Ser Gly Thr Phe Ile Thr Asp Lys Thr
        35                  40                  45

Val Leu Asp Met Lys Ala Met Asp Ser Lys Ser Asn Gly Ala Ile Ala
    50                  55                  60

Trp Ser Asn Gln Thr Ser Phe Thr Cys Gln Asp Ile Phe Lys Glu Thr
65                  70                  75                  80

Asn Ala Thr Tyr Pro Ser Ser Asp Val Pro Cys Asp Ala Thr Leu Thr
                85                  90                  95

Glu Lys Ser Phe Glu Thr Asp Met Asn Leu Asn Phe Gln Asn Leu Ser
            100                 105                 110

Val Met Gly Leu Arg Ile Leu Leu Leu Lys Val Ala Gly Phe Asn Leu
        115                 120                 125

Leu Met Thr Leu Arg Leu Trp Ser Ser
    130                 135


<210> SEQ ID NO 41
<211> LENGTH: 172
<212> TYPE: PRT
<213> ORGANISM: Artificial Sequence
<220> FEATURE:
<223> OTHER INFORMATION: mouse TCRbC-N.rRec with random rearrangement of
      25 amino acids at N terminal

<400> SEQUENCE: 41

Pro Glu Lys Arg Glu Lys Ser Val Ala Pro Ala Val Lys Lys Leu Asn
1               5                   10                  15

Leu Ile Thr Phe Gln Asp Ser Pro Asn Ala Thr Leu Val Cys Leu Ala
            20                  25                  30

Arg Gly Phe Phe Pro Asp His Val Glu Leu Ser Trp Trp Val Asn Gly
        35                  40                  45

Lys Glu Val His Ser Gly Val Ser Thr Asp Pro Gln Ala Tyr Lys Glu
    50                  55                  60

Ser Asn Tyr Ser Tyr Cys Leu Ser Ser Arg Leu Arg Val Ser Ala Thr
65                  70                  75                  80

Phe Trp His Asn Pro Arg Asn His Phe Arg Cys Gln Val Gln Phe His
                85                  90                  95
```

```
Gly Leu Ser Glu Glu Asp Lys Trp Pro Glu Gly Ser Pro Lys Pro Val
            100                 105                 110

Thr Gln Asn Ile Ser Ala Glu Ala Trp Gly Arg Ala Asp Cys Gly Ile
        115                 120                 125

Thr Ser Ala Ser Tyr Gln Gln Gly Val Leu Ser Ala Thr Ile Leu Tyr
    130                 135                 140

Glu Ile Leu Leu Gly Lys Ala Thr Leu Tyr Ala Val Leu Val Ser Thr
145                 150                 155                 160

Leu Val Val Met Ala Met Val Lys Arg Lys Asn Ser
                165                 170


<210> SEQ ID NO 42
<211> LENGTH: 122
<212> TYPE: PRT
<213> ORGANISM: Artificial Sequence
<220> FEATURE:
<223> OTHER INFORMATION: mouse TCRaC-C.DLT with deletion of 15 amino
      acids at C terminal in constant region of chain of mouse TCR

<400> SEQUENCE: 42

Asp Ile Gln Asn Pro Glu Pro Ala Val Tyr Gln Leu Lys Asp Pro Arg
1               5                   10                  15

Ser Gln Asp Ser Thr Leu Cys Leu Phe Thr Asp Phe Asp Ser Gln Ile
            20                  25                  30

Asn Val Pro Lys Thr Met Glu Ser Gly Thr Phe Ile Thr Asp Lys Thr
        35                  40                  45

Val Leu Asp Met Lys Ala Met Asp Ser Lys Ser Asn Gly Ala Ile Ala
    50                  55                  60

Trp Ser Asn Gln Thr Ser Phe Thr Cys Gln Asp Ile Phe Lys Glu Thr
65                  70                  75                  80

Asn Ala Thr Tyr Pro Ser Ser Asp Val Pro Cys Asp Ala Thr Leu Thr
                85                  90                  95

Glu Lys Ser Phe Glu Thr Asp Met Asn Leu Asn Phe Gln Asn Leu Ser
            100                 105                 110

Val Met Gly Leu Arg Ile Leu Leu Leu Lys
        115                 120


<210> SEQ ID NO 43
<211> LENGTH: 157
<212> TYPE: PRT
<213> ORGANISM: Artificial Sequence
<220> FEATURE:
<223> OTHER INFORMATION: mouse TCRbC-C.DLT with deletion of 15 amino
      acids at C terminal in constant region of chain of mouse TCR

<400> SEQUENCE: 43

Asp Leu Arg Asn Val Thr Pro Pro Lys Val Ser Leu Phe Glu Pro Ser
1               5                   10                  15

Lys Ala Glu Ile Ala Asn Lys Gln Lys Ala Thr Leu Val Cys Leu Ala
            20                  25                  30

Arg Gly Phe Phe Pro Asp His Val Glu Leu Ser Trp Trp Val Asn Gly
        35                  40                  45

Lys Glu Val His Ser Gly Val Ser Thr Asp Pro Gln Ala Tyr Lys Glu
    50                  55                  60

Ser Asn Tyr Ser Tyr Cys Leu Ser Ser Arg Leu Arg Val Ser Ala Thr
65                  70                  75                  80

Phe Trp His Asn Pro Arg Asn His Phe Arg Cys Gln Val Gln Phe His
                85                  90                  95
```

Gly Leu Ser Glu Glu Asp Lys Trp Pro Glu Gly Ser Pro Lys Pro Val
100 105 110

Thr Gln Asn Ile Ser Ala Glu Ala Trp Gly Arg Ala Asp Cys Gly Ile
115 120 125

Thr Ser Ala Ser Tyr Gln Gln Gly Val Leu Ser Ala Thr Ile Leu Tyr
130 135 140

Glu Ile Leu Leu Gly Lys Ala Thr Leu Tyr Ala Val Leu
145 150 155

<210> SEQ ID NO 44
<211> LENGTH: 123
<212> TYPE: PRT
<213> ORGANISM: Artificial Sequence
<220> FEATURE:
<223> OTHER INFORMATION: Anti-CD19 FMC63 VH

<400> SEQUENCE: 44

Ala Val Gln Leu Val Glu Ser Gly Gly Gly Leu Val Gln Pro Gly Arg
1 5 10 15

Ser Leu Arg Leu Ser Cys Ala Ala Ser Gly Phe Thr Phe Gly Asp Tyr
20 25 30

Thr Met His Trp Val Arg Gln Ala Pro Gly Lys Gly Leu Glu Trp Val
35 40 45

Ser Gly Ile Ser Trp Asn Ser Gly Ser Ile Gly Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Leu Tyr Tyr Cys
85 90 95

Thr Lys Asp Asn Gln Tyr Gly Ser Gly Ser Thr Tyr Gly Leu Gly Val
100 105 110

Trp Gly Gln Gly Thr Leu Val Thr Val Ser Ser
115 120

<210> SEQ ID NO 45
<211> LENGTH: 107
<212> TYPE: PRT
<213> ORGANISM: Artificial Sequence
<220> FEATURE:
<223> OTHER INFORMATION: Anti-CD19 FMC63 VL

<400> SEQUENCE: 45

Glu Ile Val Leu Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile
35 40 45

Tyr Asp Ala Ser Asn Arg Ala Thr Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Arg Ser Asn Trp Pro Leu
85 90 95

Thr Phe Gly Gly Gly Thr Lys Val Glu Ile Lys
100 105

<210> SEQ ID NO 46

<211> LENGTH: 123
<212> TYPE: PRT
<213> ORGANISM: Artificial Sequence
<220> FEATURE:
<223> OTHER INFORMATION: Anti-CD20 2C6 VH

<400> SEQUENCE: 46

```
Ala Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Gly Asp Tyr
            20                  25                  30

Thr Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Thr Lys Asp Asn Gln Tyr Gly Ser Gly Ser Thr Tyr Gly Leu Gly Val
            100                 105                 110

Trp Gly Gln Gly Thr Leu Val Thr Val Ser Ser
        115                 120
```

<210> SEQ ID NO 47
<211> LENGTH: 107
<212> TYPE: PRT
<213> ORGANISM: Artificial Sequence
<220> FEATURE:
<223> OTHER INFORMATION: Anti-CD20 2C6 VL

<400> SEQUENCE: 47

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105
```

<210> SEQ ID NO 48
<211> LENGTH: 124
<212> TYPE: PRT
<213> ORGANISM: Artificial Sequence
<220> FEATURE:
<223> OTHER INFORMATION: Anti-CD22 M971 VH

<400> SEQUENCE: 48

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30
```

```
Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Glu Val Thr Gly Asp Leu Glu Asp Ala Phe Asp
            100                 105                 110

Ile Trp Gly Gln Gly Thr Met Val Thr Val Ser Ser
        115                 120


<210> SEQ ID NO 49
<211> LENGTH: 107
<212> TYPE: PRT
<213> ORGANISM: Artificial Sequence
<220> FEATURE:
<223> OTHER INFORMATION: Anti-CD22 M971 VL

<400> SEQUENCE: 49

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Trp Ser Tyr
            20                  25                  30

Leu Asn Trp Tyr Gln Gln Arg Pro Gly Lys Ala Pro Asn Leu Leu Ile
        35                  40                  45

Tyr Ala Ala Ser Ser Leu Gln Ser Gly Val Pro Ser Arg Phe Ser Gly
    50                  55                  60

Arg Gly Ser Gly Thr Asp Phe Thr Leu Thr Ile Ser Ser Leu Gln Ala
65                  70                  75                  80

Glu Asp Phe Ala Thr Tyr Tyr Cys Gln Gln Ser Tyr Ser Ile Pro Gln
                85                  90                  95

Thr Phe Gly Gln Gly Thr Lys Leu Glu Ile Lys
            100                 105


<210> SEQ ID NO 50
<211> LENGTH: 25
<212> TYPE: PRT
<213> ORGANISM: Artificial Sequence
<220> FEATURE:
<223> OTHER INFORMATION: mouse TCR beta chain constant region N-terminal

<400> SEQUENCE: 50

Asp Leu Lys Asn Val Phe Pro Pro Glu Val Ala Val Phe Glu Pro Ser
1               5                   10                  15

Glu Ala Glu Ile Ser His Thr Gln Lys
            20                  25


<210> SEQ ID NO 51
<211> LENGTH: 25
<212> TYPE: PRT
<213> ORGANISM: Artificial Sequence
<220> FEATURE:
<223> OTHER INFORMATION: mouse TCR alpha chain constant region
      N-terminal
```

```
<400> SEQUENCE: 51

Asp Leu Arg Asn Val Thr Pro Pro Lys Val Ser Leu Phe Glu Pro Ser
1               5                   10                  15

Lys Ala Glu Ile Ala Asn Lys Gln Lys
            20                  25
```